US006428990B1

(12) United States Patent
Mukerji et al.

(10) Patent No.: US 6,428,990 B1
(45) Date of Patent: Aug. 6, 2002

(54) HUMAN DESATURASE GENE AND USES THEREOF

(75) Inventors: Pradip Mukerji; Amanda Eun-Yeong Leonard, both of Gahanna; Yung-Sheng Huang, Columbus; Jennifer M. Parker-Barnes, New Albany, all of OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/439,261

(22) Filed: Nov. 12, 1999

Related U.S. Application Data

(63) Continuation-in-part of application No. 09/227,613, filed on Jan. 8, 1999, which is a continuation-in-part of application No. PCT/US98/07422, filed on Apr. 10, 1998, which is a continuation-in-part of application No. 08/833,610, filed on Apr. 11, 1997, now Pat. No. 5,972,664.

(51) Int. Cl.[7] .............................. C12P 7/64; C12P 7/62; C12N 9/02; C12N 1/20; C07H 21/04

(52) U.S. Cl. ....................... 435/134; 435/135; 435/136; 435/189; 435/252.3; 435/320.1; 536/23.2; 530/350

(58) Field of Search .............................. 435/189, 252.3, 435/320.1, 134–136; 536/23.2; 530/350

(56) References Cited

U.S. PATENT DOCUMENTS

| | | | |
|---|---|---|---|
| 5,443,974 A | 8/1995 | Hitz et al. | 435/172.3 |
| 5,552,306 A | 9/1996 | Thomas et al. | 435/134 |

FOREIGN PATENT DOCUMENTS

| | | |
|---|---|---|
| WO | WO 93/11245 | 6/1993 |
| WO | WO 94/11516 | 5/1994 |
| WO | WO 96/13591 | 5/1996 |
| WO | 9846765 | 10/1998 |
| WO | 0020603 | 4/2000 |

OTHER PUBLICATIONS

Sequence Search Alignment of Applicants' SEQ ID No. : 1 and prior art sequence in Chaudhary et al. [WO9846763–A1, Oct. 22, 1998].*

Lamerdin J. E. et al.: "BC269730_2" EMBL Database Entry 060427; Accession No. 060427 Aug. 1, 1998, XP002140846.

Cho H. P. et al.: "Cloning, Expression, and Fatty Acid Regulation of the Human Delta–5 Desaturase" Journal of Biological Chemistry, vol. 274, No. 52, Dec. 24, 1999, pp. 37335–37339, XP002140847.

Michaelson L. et al.: "Isolation of a delta5–fatty acid desaturase gene from *Mortierella alpina*" Journal of Biological Chemistry, vol. 273, No. 30, Jul. 24, 1998, pp. 19055–19059, XP002076636.

*The Faseb Journal*, Abstracts, Part I, Abstract 3093, p. A532 (Experimental Biology 98, San Francisco, CA, Apr. 18–22, 1998).

Deborah S. Knutzon et al.—"Identification of 5–Desaturase from *Mortierella alpina* by Heterologous Expression in Bakers' Yeast and Canola" The Journal of Biological Chemistry (1998) vol. 273, No. 45, Issue of Nov. 6, pp. 29360–29366 (1998).

Hyekyung P. Cho, et al.,—"Cloning, Expression, and Nutritional Regulation of the Mammalian –6 Desaturase" The Journal of Biological Chemistry (1999) vol. 274, No.1, Issue of Jan. 1, pp. 471–477 (1999).

J. E. Lamerdin, et al., "Sequence Analysis of a Human BAC Containing the FEN1 DNA Repair Gene" —Accession AC004770, Jun. 12, 1998—GenBank.

* cited by examiner

*Primary Examiner*—Tekchand Saidha
(74) *Attorney, Agent, or Firm*—Cheryl L. Becker

(57) ABSTRACT

The subject invention relates to the identification of a gene involved in the desaturation of polyunsaturated fatty acids at carbon 5 (i.e., "human Δ5-desaturase") and to uses thereof. In particular, human Δ5-desaturase may be utilized, for example, in the conversion of dihomo-γ-linolenic acid (DGLA) to arachidonic acid (AA) and in the conversion of 20:4n-3 to eicosapentaenoic acid (EPA). AA or polyunsaturated fatty acids produced therefrom may be added to pharmaceutical compositions, nutritional compositions, animal feeds, as well as other products such as cosmetics.

6 Claims, 48 Drawing Sheets

| Sections of the Desaturases | Clone ID from Incyte LifeSeq Database | Keyword |
|---|---|---|
| 151-300 delta 5 | 3808675 | fatty acid desaturase |
| 301-446 delta 5 | 354535 | delta 6 |
| 151-300 delta 6 | 3448789 | delta 6 |
| 151-300 delta 6 | 1362863 | delta 6 |
| 151-300 delta 6 | 2394760 | delta 6 |
| 301-457 delta 6 | 3350263 | delta 6 |

FIG. 1

Edited Contig 2692004

GCACGCCGACCGGCGCCGGGAGATCCTGGCAAAGTATCCAGAGATAAAGTCCTTGATGAAACCTGATCCCAAT
TTGATATGGATTATAATTATGATGGTTCTCACCCAGTTGGGTGCATTTTACATAGTAAAAGACTTGGACTGGA
AATGGGTCATATTTGGGGCCTATGCGTTTGGCAGTTGCATTAACCACTCAATGACTCTGGCTATTCATGAGAT
TGCCCACAATGCTGCCTTTGGCAACTGCAAAGCAATGTGGAATCGCTGGTTTGGAATGTTTGCTAATCTTCCT
ATTGGGATTCCATATTCAATTTCCTTTAAGAGGTATCACATGGATCATCATCGGTACCTTGGAGCTGATGGCG
TCGATGTAGATATTCCTACCGATTTTGAGGGCTGGTTCTTCTGTACCGCTTTCAGAAAGTTTATATGGGTTAT
TCTTCAGCCTCTCTTTTATGCCTTTCGACCTCTGTTCATCAACCCCAAACCAATTACGTATCTGGAAGTTATC
AATACCGTGGCACAGGTCACTTTTGACATTTTAATTTATTACTTTTTGGGAATTAAATCCTTAGTCTACATGT
TGGCAGCATCTTTACTTGGCCTGGGTTTGCACCCAATTTCTGGACATTTTATAGCTGAGCATTACATGTTCTT
AAAGGGTCATGAAACTTACTCATATTATGGGCCTCTGAATTTACTTACCTTCAATGTGGGTTATCATAATGAA
CATCATGATTTCCCCAACATTCCTGGAAAAAGTCTTCCACTGGTGAGGAAAATAGCAGCTGAATACTATGACA
ACCTCCCTCACTACAATTCCTGGATAAAAGTACTGTATGATTTTGTGATGGATGATACAATAAGTCCCTACTC
AAGAATGAAGAGGCACCAAAAAGGAGAGATGGTGCTGGAGTAAATATCATTAGTGCCAAAGGGATTCTTCTCC
AAAACTTTAGATGATAAAATGGAATTTTTGCATTATTAAACTTGAGACCAGTGATGCTCAGAAGCTCCCCTGG
CACAATTTCAGAGTAAGAGCTCGGTGATACCAAGAAGTGAATCTGGCTTTTAAACAGTCAGCCTGACTCTGTA
CTGCTCAGTTTCACTCACAGGAAACTTGTGACTTGTGTATTATCGTCATTGAGGATGTTTCACTCATGTCTGT
CATTTTATAAGCATATCATTTAAAAAGCTTCTAAAAAGCTATTTCGCCAGG

FIG.2

Edited Contig 2153526

TTACCTTCTACGTCCGCTTCTTCCTCACTTATGTGCCACTATTGGGGCTGAAAGCTTCCTGGGCCTTTTCTTC
ATAGTCAGGTTCCTGGAAAGCAACTGGTTTGTGTGGGTGACACAGATGAACCATATTCCCATGCACATTGATC
ATGACCGGAACATGGACTGGGTTTCCACCCAGCTCCAGGCCACATGCAATGTCCACAAGTCTGCCTTCAATGA
CTGGTTCAGTGGACACCTCAACTTCCAGATTGAGCACCATCTTTTTCCCACGATGCCTCGACACAATTACCAC
AAAGTGGCTCCCCTGGTGCAGTCCTTGTGTGCCAAGCATGGCATAGAGTACCAGTCCAAGCCCCTGCTGTCAG
CCTTCGCCGACATCATCCACTCACTAAAGGAGTCAGGGCAGCTCTGGCTAGATGCCTATCTTCACCAATAACA
ACAGCCACCCTGCCCAGTCTGGAAGAAGAGGAGGAAGACTCTGGAGCCAAGGCAGAGGGGAGCTTGAGGGACA
ATGCCACTATAGTTTAATACTCAGAGGGGGTTGGGTTTGGGGACATAAAGCCTCTGACTCAAACTCCTCCCTT
TTATCTTCTAGCCACAGTTCTAAGACCCAAAGTGGGGGGTGGACACAGAAGTCCCTAGGAGGGAAGGAGCT

FIG.3

Edited Contig 3506132

GTCTTTTACTTTGGCAATGGCTGGATTCCTACCCTCATCACGGCCTTTGTCCTTGCTACCTCTCAGGCCCAAG
CTGGATGGCTGCAACATGATTATGGCCACCTGTCTGTCTACAGAAAACCCAAGTGGAACCACCTTGTCCACAA
ATTCGTCATTGGCCACTTAAAGGGTGCCTCTGCCAACTGGTGGAATCATCGCCACTTCCAGCACCACGCCAAG
CCTAACATCTTCCACAAGGATCCCGATGTGAACATGCTGCACGTGTTTGTTCTGGGCGAATGGCAGCCCATCG
AGTACGGCAAGA

FIG.4

Edited Contig 3854933

CAGGGACCTACCCCGCGCTACTTCACCTGGGACGAGGTGGCCCAGCGCTCAGGGTGCGAGGAGCGGTGGCTAG
TGATCGACCGTAAGGTGTACAACATCAGCGAGTTCACCCGCCGGCATCCAGGGGGCTCCCGGGTCATCAGCCA
CTACGCCGGGCAGGATGCCACGGATCCCTTTGTGGCCTTCCACATCAACAAGGGCCTTGTGAAGAAGTATATG
AACTCTCTCCTGATTGGAGAACTGTCTCCAGAGCAGCCCAGCTTTGAGCCCACCAAGAATAAAGAGCTGACAG
ATGAGTTCCGGGAGCTGCGGGCCACAGTGGAGCGGATGGGGCTCATGAAGGCCAACCATGTCTTCTTCCTGCT
GTACCTGCTGCACATCTTGCTGCTGGATGGTGCAGCCTGGCTCACCCTTTGGGTCTTTGGGACGTCCTTTTTG
CCCTTCCTCCTCTGTGCGGTGCTGCTCAGTGCAGTTCAGGCCCAGGCTGGCTGGCTGCAGCATGACTTTGGGC
ACCTGTCGGTCTTCAGCACCTCAAAGTGGAACCATCTGCTACATCATTTTGTGATTGGCCACCTGAAGGGGGC
CCCCGCCAGTTGGTGGAACCACATGCACTTCCAGCACCATGCCAAGCCCAACTGCTTCCGCAAAGACCCAGAC
ATCAACATGCATCCCTTCTTCTTTGCCTTGGGGAAGATCCTCTCTGTGGAGCTTGGGAAACAGAAGAAAAAAT
ATATGCCGTACAACCACCAGCACARATACTTCTTCCTAATTGGGCCCCCAGCCTTGCTGCCTCTCTACTTCCA
GTGGTATATTTTCTATTTTGTTATCCAGCGAAAGAAGTGGGTGGACTTGGCCTGGATCAGCAAACAGGAATAC
GATGAAGCCGGGCTTCCATTGTCCACCGCAAATGCTTCTAAA

FIG.5

Edited Contig 2511785

GCCACTTAAAGGGTGCCTCTGCCAACTGGTGGAATCATCGCCACTTCCAGCACCACGCCAAGCCTAACATCTT
CCACAAGGATCCCGATGTGAACATGCTGCACGTGTTTGTTCTGGGCGAATGGCAGCCCATCGAGTACGGCAAG
AAGAAGCTGAAATACCTGCCCTACAATCACCAGCACGAATACTTCTTCCTGATTGGGCCGCCGCTGCTCATCC
CCATGTATTTCCAGTACCAGATCATCATGACCATGATCGTCCATAAGAACTGGGTGGACCTGGCCTGGGCCGT
CAGCTACTACATCCGGTTCTTCATCACCTACATCCCTTTCTACGGCATCCTGGGAGCCCTCCTTTTCCTCAAC
TTCATCAGGTTCCTGGAGAGCCACTGGTTTGTGTGGGTCACACAGATGAATCACATCGTCATGGAGATTGACC
AGGAGGCCTACCGTGACTGGTTCAGTAGCCAGCTGACAGCCACCTGCAACGTGGAGCAGTCCTTCTTCAACGA
CTGGTTCAGTGGACACCTTAACTTCCAGATTGAGCACCACCTCTTCCCCACCATGCCCCGGCACAACTTACAC
AAGATCGCCCCGCTGGTGAAGTCTCTATGTGCCAAGCATGGCATTGAATACCAGGAGAAGCCGCTACTGAGGG
CCCTGCTGGACATCATCAGGTCCCTGAAGAAGTCTGGGAAGCTGTGGCTGGACGCCTACCTTCACAAATGAAG
CCACAGCCCCCGGGACACCGTGGGGAAGGGGTGCAGGTGGGGTGATGGCCAGAGGAATGATGGGCTTTTGTTC
TGAGGGGTGTCCGAGAGGCTGGTGTATGCACTGCTCACGGACCCCATGTTGGATCTTTCTCCCTTTCTCCTCT
CCTTTTTCTCTTCACATCTCCCCCATAGCACCCTGCCCTCATGGGACCTGCCCTCCCTCAGCCGTCAGCCATC
AGCCATGGCCCTCCCAGTGCCTCCTAGCCCCTTCTTCCAAGGAGCAGAGAGGTGGCCACCGGGGGTGGCTCTG
TCCTACCTCCACTCTCTGCCCCTAAAGATGGGAGGAGACCAGCGGTCCATGGGTCTGGCCTGTGAGTCTCCCC
TTGCAGCCTGGTCACTAGGCATCACCCCCGCTTTGGTTCTTCAGATGCTCTTGGGGTTCATAGGGGCAGGTCC
TAGTCGGGCAGGGCCCCTGACCCTCCCGGCCTGGCTTCACTCTCCCTGACGGCTGCCATTGGTCCACCCTTTC
ATAGAGAGGCCTGCTTTGTTACAAAGCTCGGGTCTCCCTCCTGCAGCTCGGTTAAGTACCCGAGGCCTCTCTT
AAGATGTCCAGGGCCCCAGGCCCGCGGGCACAGCCAGCCCAAACCTTGGGCCCTGGAAGAGTCCTCCACCCCA
TCACTAGAGTGCTCTGACCCTGGGCTTTCACGGGCCCCATTCCACCGCCTCCCCAACTTGAGCCTGTGACCTT
GGGACCAAAGGGGGAGTCCCTCGTCTCTTGTGACTCAGCAGAGGCAGTGGCCACGTTCAGGGAGGGGCCGGCT
GGCCTGGAGGCTCAGCCCACCCTCCAGCTTTTCCTCAGGGTGTCCTGAGGTCCAAGATTCTGGAGCAATCTGA
CCCTTCTCCAAAGGCTCTGTTATCAGCTGGGCAGTGCCAGCCAATCCCTGGCCATTTGGCCCCAGGGGACGTG
GGCCCTG

FIG.6

Contig 2535

GTCTTTTACTTTGGCAATGGCTGGATTCCTACCCTCATCACGGCCTTTGTCCTTGCTACCTCTCAGGCCCAAG
CTGGATGGCTGCAACATGATTATGGCCACCTGTCTGTCTACAGAAAACCCAAGTGGAACCACCTTGTCCACAA
ATTCGTCATTGGCCACTTAAAGGGTGCCTCTGCCAACTGGTGGAATCATCGCCACTTCCAGCACCACGCCAAG
CCTAACATCTTCCACAAGGATCCCGATGTGAACATGCTGCACGTGTTTGTTCTGGGCGAATGGCAGCCCATCG
AGTACGGCAAGAAGAAGCTGAAATACCTGCCCTACAATCACCAGCACGAATACTTCTTCCTGATTGGGCCGCC
GCTGCTCATCCCCATGTATTTCCAGTACCAGATCATCATGACCATGATCGTCCATAAGAACTGGGTGGACCTG
GCCTGGGCCGTCAGCTACTACATCCGGTTCTTCATCACCTACATCCCTTTCTACGGCATCCTGGGAGCCCTCC
TTTTCCTCAACTTCATCAGGTTCCTGGAGAGCCACTGGTTTGTGTGGGTCACACAGATGAATCACATCGTCAT
GGAGATTGACCAGGAGGCCTACCGTGACTGGTTCAGTAGCCAGCTGACAGCCACCTGCAACGTGGAGCAGTCC
TTCTTCAACGACTGGTTCAGTGGACACCTTAACTTCCAGATTGAGCACCACCTCTTCCCCACCATGCCCCGGC
ACAACTTACACAAGATCGCCCCGCTGGTGAAGTCTCTATGTGCCAAGCATGGCATTGAATACCAGGAGAAGCC
GCTACTGAGGGCCCTGCTGGACATCATCAGGTCCCTGAAGAAGTCTGGGAAGCTGTGGCTGGACGCCTACCTT
CACAAATGAAGCCACAGCCCCCGGGACACCGTGGGGAAGGGGTGCAGGTGGGGTGATGGCCAGAGGAATGATG
GGCTTTTGTTCTGAGGGGTGTCCGAGAGGCTGGTGTATGCACTGCTCACGGACCCCATGTTGGATCTTTCTCC
CTTTCTCCTCTCCTTTTTCTCTTCACATCTCCCCCATAGCACCCTGCCCTCATGGGACCTGCCCTCCCTCAGC
CGTCAGCCATCAGCCATGGCCCTCCCAGTGCCTCCTAGCCCCTTCTTCCAAGGAGCAGAGAGGTGGCCACCGG
GGGTGGCTCTGTCCTACCTCCACTCTCTGCCCCTAAAGATGGGAGGAGACCAGCGGTCCATGGGTCTGGCCTG
TGAGTCTCCCCTTGCAGCCTGGTCACTAGGCATCACCCCCGCTTTGGTTCTTCAGATGCTCTTGGGGTTCATA
GGGGCAGGTCCTAGTCGGGCAGGGCCCCTGACCCTCCCGGCCTGGCTTCACTCTCCCTGACGGCTGCCATTGG
TCCACCCTTTCATAGAGAGGCCTGCTTTGTTACAAAGCTCGGGTCTCCCTCCTGCAGCTCGGTTAAGTACCCG
AGGCCTCTCTTAAGATGTCCAGGGCCCCAGGCCCGCGGGCACAGCCAGCCCAAACCTTGGGCCCTGGAAGAGT
CCTCCACCCCATCACTAGAGTGCTCTGACCCTGGGCTTTCACGGGCCCCATTCCACCGCCTCCCCAACTTGAG
CCTGTGACCTTGGGACCAAAGGGGGAGTCCCTCGTCTCTTGTGACTCAGCAGAGGCAGTGGCCACGTTCAGGG
AGGGGCCGGCTGGCCTGGAGGCTCAGCCCACCCTCCAGCTTTTCCTCAGGGTGTCCTGAGGTCCAAGATTCTG
GAGCAATCTGACCCTTCTCCAAAGGCTCTGTTATCAGCTGGGCAGTGCCAGCCAATCCCTGGCCATTTGGCCC
CAGGGGACGTGGGCCCTG

FIG.7

Edited Contig 253538a

```
CAGGGACCTACCCCGCGCTACTTCACCTGGGACGAGGTGGCCCAGCGCTCAGGGTGCGAGGAGCGGTGGCTAGTGATCGA
CCGTAAGGTGTACAACATCAGCGAGTTCACCCGCCGGCATCCAGGGGGCTCCCGGGTCATCAGCCACTACGCCGGGCAGG
ATGCCACGGATCCCTTTGTGGCCTTCCACATCAACAAGGGCCTTGTGAAGAAGTATATGAACTCTCTCCTGATTGGAGAA
CTGTCTCCAGAGCAGCCCAGCTTTGAGCCCACCAAGAATAAAGAGCTGACAGATGAGTTCCGGGAGCTGCGGGCCACAGT
GGAGCGGATGGGGCTCATGAAGGCCAACCATGTCTTCTTCCTGCTGTACCTGCTGCACATCTTGCTGCTGGATGGTGCAG
CCTGGCTCACCCTTTGGGTCTTTGGGACGTCCTTTTTGCCCTTCCTCCTCTGTGCGGTGCTGCTCAGTGCAGTTCAGCAG
GCCCAAGCTGGATGGCTGCAACATGATTATGGCCACCTGTCTGTCTACAGAAAACCCAAGTGGAACCACCTTGTCCACAA
ATTCGTCATTGGCCACTTAAAGGGTGCCTCTGCCAACTGGTGGAATCATCGCCACTTCCAGCACCACGCCAAGCCTAACA
TCTTCCACAAGGATCCCGATGTGAACATGCTGCACGTGTTTGTTCTGGGCGAATGGCAGCCCATCGAGTACGGCAAGAAG
AAGCTGAAATACCTGCCCTACAATCACCAGCACGAATACTTCTTCCTGATTGGGCCGCCGCTGCTCATCCCCATGTATTT
CCAGTACCAGATCATCATGACCATGATCGTCCATAAGAACTGGGTGGACCTGGCCTGGGCCGTCAGCTACTACATCCGGT
TCTTCATCACCTACATCCCTTTCTACGGCATCCTGGGAGCCCTCCTTTTCCTCAACTTCATCAGGTTCCTGGAGAGCCAC
TGGTTTGTGTGGGTCACACAGATGAATCACATCGTCATGGAGATTGACCAGGAGGCCTACCGTGACTGGTTCAGTAGCCA
GCTGACAGCCACCTGCAACGTGGAGCAGTCCTTCTTCAACGACTGGTTCAGTGGACACCTTAACTTCCAGATTGAGCACC
ACCTCTTCCCCACCATGCCCCGGCACAACTTACACAAGATCGCCCCGCTGGTGAAGTCTCTATGTGCCAAGCATGGCATT
GAATACCAGGAGAAGCCGCTACTGAGGGCCCTGCTGGACATCATCAGGTCCCTGAAGAAGTCTGGGAAGCTGTGGCTGGA
CGCCTACCTTCACAAATGAAGCCACAGCCCCCGGGACACCGTGGGGAAGGGGTGCAGGTGGGGTGATGGCCAGAGGAATG
ATGGGCTTTTGTTCTGAGGGGTGTCCGAGAGGCTGGTGTATGCACTGCTCACGGACCCCATGTTGGATCTTTCTCCCTTT
CTCCTCTCCTTTTTCTCTTCACATCTCCCCCATAGCACCCTGCCCTCATGGGACCTGCCCTCCCTCAGCCGTCAGCCATC
AGCCATGGCCCTCCCAGTGCCTCCTAGCCCCTTCTTCCAAGGAGCAGAGAGGTGGCCACCGGGGGTGGCTCTGTCCTACC
TCCACTCTCTGCCCCTAAAGATGGGAGGAGACCAGCGGTCCATGGGTCTGGCCTGTGAGTCTCCCCTTGCAGCCTGGTCA
CTAGGCATCACCCCCGCTTTGGTTCTTCAGATGCTCTTGGGGTTCATAGGGGCAGGTCCTAGTCGGGCAGGGCCCCTGAC
CCTCCCGGCCTGGCTTCACTCTCCCTGACGGCTGCCATTGGTCCACCCTTTCATAGAGAGGCCTGCTTTGTTACAAAGCT
CGGGTCTCCCTCCTGCAGCTCGGTTAAGTACCCGAGGCCTCTCTTAAGATGTCCAGGGCCCCAGGCCCGCGGGCACAGCC
AGCCCAAACCTTGGGCCCTGGAAGAGTCCTCCACCCCATCACTAGAGTGCTCTGACCCTGGGCTTTCACGGGCCCCATTC
CACCGCCTCCCCAACTTGAGCCTGTGACCTTGGGACCAAAGGGGGAGTCCCTCGTCTCTTGTGACTCAGCAGAGGCAGTG
GCCACGTTCAGGGAGGGGCCGGCTGGCCTGGAGGCTCAGCCCACCCTCCAGCTTTTCCTCAGGGTGTCCTGAGGTCCAAG
ATTCTGGAGCAATCTGACCCTTCTCCAAAGGCTCTGTTATCAGCTGGGCAGTGCCAGCCAATCCCTGGCCATTTGGCCCC
AGGGGACGTGGGCCCTG
```

FIG.8

FastA Match of Ma29 and contig 253538a

```
SCORES      Init1:   117 Initn:   225 Opt:   256
Smith-Waterman score: 408;    27.0% identity in 441 aa overlap

                    10        20        30        40        50
Ma29.pep    MGTDQGKT---FTWEELAAHNTKDDLLLAIRGRVYDVTKFLSRHPGGVDTLLLGAGRDVT
                ||  |   |||:|:|  ::  ::  |:|  :||::::|  |||||  ::   ||:|:|
253538a         QGPTPRYFTWDEVAQRSGCEERWLVIDRKVYNISEFTRRHPGGSRVISHYAGQDAT
                       10        20        30        40        50

             60        70        80        90       100       110
Ma29.pep    PVFEMYHAF-GAADAIMKKYYVGTLVSNELPIFPEPTVFHKTIKTRVEGYFTDRNIDPKN
              |  :|   | :   |::  :| | | | | | |||  ::        |   | : :   :
253538a     DPFVAFHINKGLVKKYMNSLLIGEL-SPEQPSF-EPTKNKELTDEFRELRATVERMGLMK
             60        70        80          90       100       110

            120       130       140       150         160       170
Ma29.pep    RPEIWGRYALIFGSLIASYYAQLFVPFVVERTWLQVVF-AIIMGFACAQVGLNPLHDASH
              :::  : | :  ::     |  :: :|   ::|  :: |:::: : ||:|     || :|
253538a     ANHVF--FLLYLLHILLLDGAAWLTLWVFGTSFLPFLLCAVLLSAVQAQAGWLQ-HDYGH
                 120       130       140       150       160        170

             180       190           200       210       220
Ma29.pep    FSVTHNPTVWKILGATHDF----FNGASYLVWMYQHMLGHHPYTNIAGADPDVSTSE---
            :|| ::|  |: |  :| |     ::|||  | ::| : ||   ||   ||||:  :
253538a     LSVYRKPK-WNHL--VHKFVIGHLKGASANWWNHRH-FQHHAKPNIFHKDPDVNMLHVFV
                   180         190       200         210       220

              230       240         250         260       270       280
Ma29.pep    ----PDVRRIKPNQKWF-VNHINQHMFV--PFLYGLLAFKVRIQDINILYFVKTNDAIRV
                 ::  | : |::  || ::::|:  | |    : |: :|    |: ::  :: : :
253538a     LGEWQPIEYGKKKLKYLPYNHQHEYFFLIGPPLLIPMYFQYQI----IMTMIVHKNWVDL
            230       240       250       260       270           280

                  290       300       310       320       330       340
Ma29.pep    NPISTWHTVMFWGGKAFFVWYRLIVPLQYLPLGKVLLLFTVADMVSSYWLALTFQANHVV
                :| : ::      ||: |    :|: |  || :||:::   :: |:|:: : | ||:|
253538a     ----AWAVSYYI---RFFITY---IPF-YGILG-ALLFLNFIRFLESHWFVWVTQMNHIV
                  290                 300        310        320       330

                  350       360                370       380       390
Ma29.pep    EEVQWPLPDENGIIQKDWAAMQVETT----QDYAHDSHLWTSITGSLNYQAVHHLFPNVS
             |:     |:::   :|| : |: :|     |:: :|    | |   | ||:|   |||||::
253538a     MEI-----DQEAY--RDWFSSQLTATCNVEQSFFND---WFS--GHLNFQIEHHLFPTMP
                          340       350       360             370
```

FIG.9A

```
                   400           410           420           430           440
Ma29.pep           QHHYPDILAIIKNTCSEYKVPYLVKDTFWQAFASHLEHLRVLGLRPKEEX
                   :|:     |   ::|:  |::: :  |   |
253538a            RHNLHKIAPLVKSLCAKHGIEYQEKPLLRALLDIIRSLKKSGKLWLDAYLHKX
                380           390           400           410           420           430
```

FIG.9B

FastA Match of Ma524 and contig 253538a

```
SCORES      Init1:   231 Initn:   499 Opt:   401
Smith-Waterman score: 620;    27.3% identity in 455 aa overlap

                      10        20        30        40        50       59
Ma524.pep     MAAAPSVRTFTRAEVLNAEALNEGKKDAEAPFLMIIDNKVYDVREFVPDHPGGSVILTH-
                  |: | ||  ||        :::::     ::|| |||:: ||:  ||||| :::|
253538a         QGPTPRYFTWDEV--------AQRSGCEERWLVIDRKVYNISEFTRRHPGGSRVISHY
                        10                 20        30        40        50

             60        70        80        90          100       110
Ma524.pep     VGKDGTDVFDTFHPEAAW--ETLANFYVGDIDE---SDRDIKNDDFAAEVRKLRTLFQSL
              :|:|:|| | :|| : :   : : :: :|:::     | :  || ::: | |:||:  : :
253538a       AGQDATDPFVAFHINKGLVKKYMNSLLIGELSPEQPSFEPTKNKELTDEFRELRATVERM
                      60        70        80        90        100       110

                 120       130       140       150       160       170
Ma524.pep     GYYDSSKAYYAFKVSFNLCIWGLSTVIVAKWGQTSTLANVLSAALLGLFWQQCGWLAHDF
              | : :::::: : :    | : | : : :  :| || |   :| |:||:     | ||| ||:
253538a       GLMKANHVFFLLYLLHILLLDGAAWLTLWVFG-TSFLPFLLCAVLLSAVQAQAGWLQHDY
                  120       130       140        150       160

                 180       190       200       210        220       230
Ma524.pep     LHHQVFQDRFWGDLFGAFLGGVCQGFSSSWWKDKHNTHHAAPNVHGEDPDIDTHPLLTWS
               | :|::     |: |    |: |   :| |::||: :|  ||| ||:  :|||::    :|
253538a       GHLSVYRKPKWNHLVHKFVIGHLKGASANWWNHRHFQHHAKPNIFHKDPDVN---ML---
            170       180       190       200       210       220

                 240       250       260       270          280       290
Ma524.pep     EHALEMFSDVPDEELTRMWSRFMVLNQTWFYFPILS---FARLSWCLQSILFVLPNGQAH
               |:: ::::      |  :    :::  |:   || :::    :  :  :  | |: ::    :|
253538a       -HVF-VLGEWQPIEYGKKKLKYLPYNHQHEYFFLIGPPLLIPMYFQYQIIMTMI----VH
                 230       240       250       260       270

                    300       310       320         330       340       349
Ma524.pep     KPSGARVPISLVEQLSLAMHWTWYLATMFLFIK--DPVNMLVYFLVSQAVCGNLLAIVFS
              |           : ::||   ::|:  :: :|      :: |:::    : : :: :: | :
253538a       K-----------NWVDLAWAVSYYIRFFITYIPFYGILGALLFLNFIRFLESHWFVWVTQ
                         280       290       300       310       320

            350       360       370       380       390       400      409
Ma524.pep     LNHNGMPVISKEEAVDMDFFTKQIITGRDVHPGLFANWFTGGLNYQIEHHLFPSMPRHNF
              :||  | :    :||    |:|::|: :  :|: ::| :||:| ||:||||||||:|||||:
253538a       MNHIVMEI--DQEAYR-DWFSSQLTATCNVEQSFFNDWFSGHLNFQIEHHLFPTMPRHNL
                330       340       350       360       370       380
```

FIG.10A

```
              410       420       430       440       450
Ma524.pep    SKIQPAVETLCKKYNVRYHTTGMIEGTAEVFSRLNEVSKAASKMGKAQX
               || |  |::|| |::::|:   ::::  :::  |:: :|
253538a      HKIAPLVKSLCAKHGIEYQEKPLLRALLDIIRSLKKSGKLWLDAYLHKX
                    390       400       410       420       430
```

FIG.10B

Human D5-desaturase

ATGGCCCCCGACCCGGTGGCCGCCGAGACCGCGGCTCAGGGACCTACCCCGCGCTACTTCACCTGGGACGAGG
TGGCCCAGCGCTCAGGGTGCGAGGAGCGGTGGCTAGTGATCGACCGTAAGGTGTACAACATCAGCGAGTTCAC
CCGCCGGCATCCAGGGGGCTCCCGGGTCATCAGCCACTACGCCGGGCAGGATGCCAC<u>GGATCC</u>CTTTGTGGCC
TTCCACATCAACAAGGGCCTTGTGAAGAAGTATATGAACTCTCTCCTGATTGGAGAACTGTCTCCAGAGCAGC
CCAGCTTTGAGCCCACCAAGAATAAAGAGCTGACAGATGAGTTCCGGGAGCTGCGGGCCACAGTGGAGCGGAT
GGGGCTCATGAAGGCCAACCATGTCTTCTTCCTGCTGTACCTGCTGCACATCTTGCTGCTGGATGGTGCAGCC
TGGCTCACCCTTTGGGTCTTTGGGACGTCCTTTTTGCCCTTCCTCCTCTGTGCGGTGCTGCTCAGTGCAGTTC
AGGCCCAGGCTGGCTGGCTGCAGCATGACTTTGGGCACCTGTCGGTCTTCAGCACCTCAAAGTGGAACCATCT
GCTACATCATTTTGTGATTGGCCACCTGAAGGGGGCCCCCGCCAGTTGGTGGAACCACATGCACTTCCAGCAC
CATGCCAAGCCCAACTGCTTCCGCAAAGACCCAGACATCAACATGCATCCCTTCTTCTTTGCCTTGGGGAAGA
TCCTCTCTGTGGAGCTTGGGAAACAGAAGAAAAAATATATGCCGTACAACCACCAGCACAAATACTTCTTCCT
AATTGGGCCCCCAGCCTTGCTGCCTCTCTACTTCCAGTGGTATATTTTCTATTTTGTTATCCAGCGAAAGAAG
TGGGTGGACTTGGCCTGGATGATTACCTTCTACGTCCGCTTCTTCCTCACTTATGTGCCACTATTGGGGCTGA
AAGCCTTCCTGGGCCTTTTCTTCATAGTCAGGTTCCTGGAAAGCAACTGGTTTGTGTGGGTGACACAGATGAA
CCATATTCCCATGCACATTGATCATGACCGGAACATGGACTGGGTTTCCACCCAGCTCCTGGCCACATGCAAT
GTCCACAAGTCTGCCTTCAATGACTGGTTCAGTGGACACCTCAACTTCCAGATTGAGCACCATCTTTTTCCCA
CGATGCCTCGACACAATTACCACAAAGTGGCTCCCCTGGTGCAGTCCTTGTGTGCCAAGCGTGGCATAGAGTA
CCAGTCCAAGCCCCTGCTGTCAGCCTTCGCCGACATCATCCACTCACTAAAGGAGTCAGGGCAGCTCTGGCTA
GATGCCTATCTTCACCAATAA

FIG.12

Human D5-desaturase

1 MAPDPVAAET AAQGPTPRYF TWDEVAQRSG CEERWLVIDR KVYNISEFTR

51 RHPGGSRVIS HYAGQDATDP FVAFHINKGL VKKYMNSLLI GELSPEQPSF

101 EPTKNKELTD EFRELRATVE RMGLMKANHV FFLLYLLHIL LLDGAAWLTL

151 WVFGTSFLPF LLCAVLLSAV QAQAGWLQHD FGHLSVFSTS KWNHLLHHFV

201 IGHLKGAPAS WWNHMHFQHH AKPNCFRKDP DINMHPFFFA LGKILSVELG

251 KQKKKYMPYN HQHKYFFLIG PPALLPLYFQ WYIFYFVIQR KKWVDLAWMI

301 TFYVRFFLTY VPLLGLKAFL GLFFIVRFLE SNWFVWVTQM NHIPMHIDHD

351 RNMDWVSTQL LATCNVHKSA FNDWFSGHLN FQIEHHLFPT MPRHNYHKVA

401 PLVQSLCAKR GIEYQSKPLL SAFADIIHSL KESGQLWLDA YLHQ*

FIG.13 pRAE-7 Complete Sequence

```
         10          20          30          40
  *     *     *     *     *     *     *     *     *
CTC CTG GAG CCC GTC AGT ATC GGC GGA ATT CCG GCA GTT CAG GCC CAG
Leu Leu Glu Pro Val Ser Ile Gly Gly Ile Pro Ala Val Gln Ala Gln>
___a___a___a___a_TRANSLATION OF PRAE-7 MV [A]__a___a___a___a___>

50          60          70          80          90
 *     *     *     *     *     *     *     *     *     *
GCT GGC TGG CTG CAG CAT GAC TTT GGG CAC CTG TCG GTC TTC AGC ACC
Ala Gly Trp Leu Gln His Asp Phe Gly His Leu Ser Val Phe Ser Thr>
___a___a___a___a_TRANSLATION OF PRAE-7 MV [A]__a___a___a___a___>

  100         110         120         130         140
    *     *     *     *     *     *     *     *     *
TCA AAG TGG AAC CAT CTG CTA CAT CAT TTT GTG ATT GGC CAC CTG AAG
Ser Lys Trp Asn His Leu Leu His His Phe Val Ile Gly His Leu Lys>
___a___a___a___a_TRANSLATION OF PRAE-7 MV [A]__a___a___a___a___>

    150         160         170         180         190
*     *     *     *     *     *     *     *     *     *
GGG GCC CCC GCC AGT TGG TGG AAC CAC ATG CAC TTC CAG CAC CAT GCC
Gly Ala Pro Ala Ser Trp Trp Asn His Met His Phe Gln His His Ala>
___a___a___a___a_TRANSLATION OF PRAE-7 MV [A]__a___a___a___a___>

       200         210         220         230         240
  *     *     *     *     *     *     *     *     *     *
AAG CCC AAC TGC TTC CGC AAA GAC CCA GAC ATC AAC ATG CAT CCC TTC
Lys Pro Asn Cys Phe Arg Lys Asp Pro Asp Ile Asn Met His Pro Phe>
___a___a___a___a_TRANSLATION OF PRAE-7 MV [A]__a___a___a___a___>

          250         260         270         280
  *     *     *     *     *     *     *     *     *
TTC TTT GCC TTG GGG AAG ATC CTC TCT GTG GAG CTT GGG AAA CAG AAG
Phe Phe Ala Leu Gly Lys Ile Leu Ser Val Glu Leu Gly Lys Gln Lys>
___a___a___a___a_TRANSLATION OF PRAE-7 MV [A]__a___a___a___a___>

290         300         310         320         330
 *     *     *     *     *     *     *     *     *     *
AAA AAA TAT ATG CCG TAC AAC CAC CAG CAC AAA TAC TTC TTC CTA ATT
Lys Lys Tyr Met Pro Tyr Asn His Gln His Lys Tyr Phe Phe Leu Ile>
___a___a___a___a_TRANSLATION OF PRAE-7 MV [A]__a___a___a___a___>
```

FIG.15A

```
  340        350        360         370        380
    *    *     *     *    *     *     *    *     *
GGG CCC CCA GCC TTG CTG CCT CTC TAC TTC CAG TGG TAT ATT TTC TAT
Gly Pro Pro Ala Leu Leu Pro Leu Tyr Phe Gln Trp Tyr Ile Phe Tyr>
___a___a___a___a_TRANSLATION OF PRAE-7 MV [A]__a___a___a___a___>

    390         400        410        420         430
*    *     *     *    *     *     *    *     *     *
TTT GTT ATC CAG CGA AAG AAG TGG GTG GAC TTG GCC TGG ATG ATT ACC
Phe Val Ile Gln Arg Lys Lys Trp Val Asp Leu Ala Trp Met Ile Thr>
___a___a___a___a_TRANSLATION OF PRAE-7 MV [A]__a___a___a___a___>

      440        450         460        470        480
  *     *     *     *    *     *     *    *     *     *
TTC TAC GTC CGC TTC TTC CTC ACT TAT GTG CCA CTA TTG GGG CTG AAA
Phe Tyr Val Arg Phe Phe Leu Thr Tyr Val Pro Leu Leu Gly Leu Lys>
___a___a___a___a_TRANSLATION OF PRAE-7 MV [A]__a___a___a___a___>

         490        500        510        520
     *     *     *     *     *    *     *     *     *
GCC TTC CTG GGC CTT TTC TTC ATA GTC AGG TTC CTG GAA AGC AAC TGG
Ala Phe Leu Gly Leu Phe Phe Ile Val Arg Phe Leu Glu Ser Asn Trp>
___a___a___a___a_TRANSLATION OF PRAE-7 MV [A]__a___a___a___a___>

530        540         550        560        570
 *     *     *     *     *    *     *     *     *     *
TTT GTG TGG GTG ACA CAG ATG AAC CAT ATT CCC ATG CAC ATT GAT CAT
Phe Val Trp Val Thr Gln Met Asn His Ile Pro Met His Ile Asp His>
___a___a___a___a_TRANSLATION OF PRAE-7 MV [A]__a___a___a___a___>

  580        590        600         610        620
    *    *     *     *    *     *     *    *     *
GAC CGG AAC ATG GAC TGG GTT TCC ACC CAG CTC CAG GCC ACA TGC AAT
Asp Arg Asn Met Asp Trp Val Ser Thr Gln Leu Gln Ala Thr Cys Asn>
___a___a___a___a_TRANSLATION OF PRAE-7 MV [A]__a___a___a___a___>

    630         640        650        660         670
*    *     *     *    *     *     *    *     *     *
GTC CAC AAG TCT GCC TTC AAT GAC TGG TTC AGT GGA CAC CTC AAC TTC
Val His Lys Ser Ala Phe Asn Asp Trp Phe Ser Gly His Leu Asn Phe>
___a___a___a___a_TRANSLATION OF PRAE-7 MV [A]__a___a___a___a___>

      680        690         700        710        720
  *     *     *     *    *     *     *    *     *     *
CAG ATT GAG CAC CAT CTT TTT CCC ACG ATG CCT CGA CAC AAT TAC CAC
Gln Ile Glu His His Leu Phe Pro Thr Met Pro Arg His Asn Tyr His>
___a___a___a___a_TRANSLATION OF PRAE-7 MV [A]__a___a___a___a___>
```

FIG.15B

```
          730         740         750         760
     *     *     *     *     *     *     *     *     *
AAA GTG GCT CCC CTG GTG CAG TCC TTG TGT GCC AAG CAT GGC ATA GAG
Lys Val Ala Pro Leu Val Gln Ser Leu Cys Ala Lys His Gly Ile Glu>
___a___a___a___a_TRANSLATION OF PRAE-7 MV [A]__a___a___a___a___>

770         780         790         800         810
 *     *     *     *     *     *     *     *     *     *
TAC CAG TCC AAG CCC CTG CTG TCA GCC TTC GCC GAC ATC ATC CAC TCA
Tyr Gln Ser Lys Pro Leu Leu Ser Ala Phe Ala Asp Ile Ile His Ser>
___a___a___a___a_TRANSLATION OF PRAE-7 MV [A]__a___a___a___a___>

   820         830         840         850         860
     *     *     *     *     *     *     *     *     *
CTA AAG GAG TCA GGG CAG CTC TGG CTA GAT GCC TAT CTT CAC CAA TAA
Leu Lys Glu Ser Gly Gln Leu Trp Leu Asp Ala Tyr Leu His Gln ***>
___a___a___a___a_TRANSLATION OF PRAE-7 MV [A]__a___a___a___a___>
```

FIG.15C

FastA Match of the Gene in pRAE-7 and the M. alpina
D5-desaturase (Ma29) Translated Sequences

```
SCORES      Init1:    62 Initn:   105 Opt:   245
Smith-Waterman score: 271;    28.4% identity in 292 aa overlap

                              10        20        30        40
pRAE-7.pep            LLEPVSIGGIPAVQAQAGWLQ-HDFGHLSV-FSTSKWNHL--LH
                                        ||:|   || :|:||  : : |: |   |
Ma29.pep     ASYYAQLFVPFVVERTWLQVVFAIIMGFACAQVGLNPLHDASHFSVTHNPTVWKILGATH
                   140       150       160       170       180       190

                   50        60        70        80        90
pRAE-7.pep   HFVIGHLKGAPASWWNHMH-FQHHAKPNCFRKDPDINM-HPFFFALGKILSVELGKQKKK
              |     ::||    | ::| : ||    |     |||::  :|           :|:  | ::|
Ma29.pep     DF----FNGASYLVWMYQHMLGHHPYTNIAGADPDVSTSEP---------DVRRIKPNQK
                    200       210       220                 230

        100         110       120       130            140       149
pRAE-7.pep   YMPYNH--QHKYF-FLIGPPALLPLYFQWYIFYFVIQ----RKKWVDLAWMITFY--VRF
             ::  ||  || :   || |   |:      :   |:|||       | : ::     : |:    |
Ma29.pep     WF-VNHINQHMFVPFLYGLLAFKVRIQDINILYFVKTNDAIRVNPISTWHTVMFWGGKAF
           240       250       260       270       280       290

           150       160       170       180       190
pRAE-7.pep   FLTY---VPL--LGLKAFLGLFFIVRFLESNWFVWVTQMNHIPMHID---HDRN----MD
             |: |    |||  | |   | || :: :: | |:: : | ||:  :::    |:|      |
Ma29.pep     FVWYRLIVPLQYLPLGKVLLLFTVADMVSSYWLALTFQANHVVEEVQWPLPDENGIIQKD
             300       310       320       330       340       350

              200       210       220       230       240       250
pRAE-7.pep   WVSTQLQATCN-VHKSAFNDWFSGHLNFQIEHHLFPTMPRHNYHKVAPLVQSLCAKHGIE
             |:: |:::| : :| | :    ::| ||:|  |||||:: :|:|  :  :::: |::: :
Ma29.pep     WAAMQVETTQDYAHDSHLWTSITGSLNYQAVHHLFPNVSQHHYPDILAIIKNTCSEYKVP
             360       370       380       390       400       410

              260       270       280
pRAE-7.pep   YQSKPLL-SAFADIIHSLKESGQLWLDAYLHQX
             |  |  : :|||: :: |:  |
Ma29.pep     YLVKDTFWQAFASHLEHLRVLGLRPKEEX
             420       430       440
```

FIG. 16

FastA Match of the Gene in pRAE-7 and M. alpina
D6-desaturase (Ma524) Translated Sequences

```
SCORES      Init1:   278 Initn:   483 Opt:   301
Smith-Waterman score: 498;    31.9% identity in 285 aa overlap

                                   10        20        30        40
pRAE-7.pep              LLEPVSIGGIPAVQAQAGWLQHDFGHLSVFSTSKWNHLLHHFVIG
                                          | ||| ||| | :||:   |: |:  |: |
Ma524.pep     GLSTVIVAKWGQTSTLANVLSAALLGLFWQQCGWLAHDFLHHQVFQDRFWGDLFGAFLGG
                  140       150       160       170       180       190

                  50        60        70        80            90
pRAE-7.pep    HLKGAPASWWNHMHFQHHAKPNCFRKDPDINMHPFF----FALGKILSV---ELGKQKKK
                :|  :|||:  |  ||| ||   :||||: ||::     ||  : :|   || :: ::
Ma524.pep     VCQGFSSSWWKDKHNTHHAAPNVHGEDPDIDTHPLLTWSEHALEMFSDVPDEELTRMWSR
                  200       210       220       230       240       250

             100       110       120       130                     140
pRAE-7.pep    YMPYNHQHKYFFLIGPPALLPLYFQWYIFYFV------------IQRKKWVDLAWMITF
              :|  |  |  ::| |    |  |   :|  :| :            |:  : ::||    |:
Ma524.pep     FMVLN-QTWFYFPILSFARLSWCLQSILFVLPNGQAHKPSGARVPISLVEQLSLAMHWTW
                  260        270       280       290       300       310

                  150         160       170       180       190       200
pRAE-7.pep    YVRFFLTYV--PLLGLKAFLGLFFIVRFLESNWFVWVTQMNHIPMHI---DHDRNMDWVS
              |:  :: ::  |:       :|  |:: : : :| :: | ::||  | :   :: :||: :
Ma524.pep     YLATMFLFIKDPV----NMLVYFLVSQAVCGNLLAIVFSLNHNGMPVISKEEAVDMDFFT
                   320            330       340       350       360       370

                      210       220       230       240       250       260
pRAE-7.pep    TQLQATCNVHKSAFNDWFSGHLNFQIEHHLFPTMPRHNYHKVAPLVQSLCAKHGIEYQSK
               |: :   :|| : | :||:| ||:||||||||:|||||: |: | | |::|| |::::|::
Ma524.pep     KQIITGRDVHPGLFANWFTGGLNYQIEHHLFPSMPRHNFSKIQPAVETLCKKYNVRYHTT
                      380       390       400       410       420       430

                      270       280
pRAE-7.pep    PLLSAFADIIHSLKESGQLWLDAYLHQX
               :: :  |:::   |:|
Ma524.pep     GMIEGTAEVFSRLNEVSKAASKMGKAQX
                      440       450
```

FIG.17

FastA Match of the Gene in pRAE-7 and contig 2535

```
SCORES       Init1:  1028 Initn:  1424 Opt:  1430
Smith-Waterman score: 1430;    71.0% identity in 276 aa overlap

                           10        20        30        40        50
pRAE-7.pep         LLEPVSIGGIPAVQAQAGWLQHDFGHLSVFSTSKWNHLLHHFVIGHLKGAPA
                               ||||||||||:|||||:   |||||:|:||||||||| |
2535           VFYFGNGWIPTLITAFVLATSQAQAGWLQHDYGHLSVYRKPKWNHLVHKFVIGHLKGASA
                       10        20        30        40        50        60

                       60        70        80        90       100       110
pRAE-7.pep     SWWNHMHFQHHAKPNCFRKDPDINM-HPFFFALGKILSVELGKQKKKYMPYNHQHKYFFL
               :|||| ||||||||| |:||||:|| |   |:||:   :| ||:| ||:||||||:||||
2535           NWWNHRHFQHHAKPNIFHKDPDVNMLH--VFVLGEWQPIEYGKKKLKYLPYNHQHEYFFL
                       70        80        90       100       110

                      120       130       140       150        160       170
pRAE-7.pep     IGPPALLPLYFQWYIFYFVIQRKKWVDLAWMITFYVRFFLTYVPLLG-LKAFLGLFFIVR
               |||| |:|:|||: |:: :| :|:|||||| :::|:|||:||:|: | | |:| | || |
2535           IGPPLLIPMYFQYQIIMTMIVHKNWVDLAWAVSYYIRFFITYIPFYGILGALLFLNFI-R
               120       130       140       150       160       170

                       180       190       200       210       220       230
pRAE-7.pep     FLESNWFVWVTQMNHIPMHIDHDRNMDWVSTQLQATCNVHKSAFNDWFSGHLNFQIEHHL
               ||||:||||||||||| |:||::   || |:|| ||||||::| ||||||||||||||||
2535           FLESHWFVWVTQMNHIVMEIDQEAYRDWFSSQLTATCNVEQSFFNDWFSGHLNFQIEHHL
               180       190       200       210       220       230

                       240       250       260       270       280
pRAE-7.pep     FPTMPRHNYHKVAPLVQSLCAKHGIEYQSKPLLSAFADIIHSLKESGQLWLDAYLHQX
               |||||||| ||:||||:|||||||||||| |||| |:  |||:|||:||:||||||||:|
2535           FPTMPRHNLHKIAPLVKSLCAKHGIEYQEKPLLRALLDIIRSLKKSGKLWLDAYLHKXSH
               240       250       260       270       280       290

2535           SPRDTVGKGCRWGDGQRNDGLLFXGVSERLVYALLTDPMLDLSPFLLSFFSSHLPHSTLP
               300       310       320       330       340       350
```

FIG.18

FastA Match of the Gene in pRAE-7 and contig 38

```
SCORES       Init1:   965 Initn:   965 Opt:   968
Smith-Waterman score: 968;    97.0% identity in 133 aa overlap

                                        10        20        30       39
pRAE-7.pep                      LLEPVSIGGIPAVQAQAGWLQHDFGHLSVFSTSKWNHLL
                                             : ||||||||||||||||||||||||||||
38          LHILLLDGAAWLTLWVFGTSFLPFLLCAVLLSAVQAQAGWLQHDFGHLSVFSTSKWNHLL
               130       140       150       160       170       180

           40        50        60        70        80        90       99
pRAE-7.pep  HHFVIGHLKGAPASWWNHMHFQHHAKPNCFRKDPDINMHPFFFALGKILSVELGKQKKKY
            ||||||||||||||||||||||||||||||||||||||||||||||||||||||||||||
38          HHFVIGHLKGAPASWWNHMHFQHHAKPNCFRKDPDINMHPFFFALGKILSVELGKQKKKY
               190       200       210       220       230       240

          100       110       120       130       140       150      159
pRAE-7.pep  MPYNHQHKYFFLIGPPALLPLYFQWYIFYFVIQRKKWVDLAWMITFYVRFFLTYVPLLGL
            ||||||| |||||||||||||||||||||||||||||||||:
38          MPYNHQHXYFFLIGPPALLPLYFQWYIFYFVIQRKKWVDLAWISKQEYDEAGLPLSTANA
               250       260       270       280       290       300

          160       170       180       190       200       210      219
pRAE-7.pep  KAFLGLFFIVRFLESNWFVWVTQMNHIPMHIDHDRNMDWVSTQLQATCNVHKSAFNDWFS

38          SK
```

FastA Match of the N-terminus of Clone A-1 and
Human Cytochrome b5

```
A-1.pdt
SW:CYB5_HUMAN

ID   CYB5_HUMAN     STANDARD;      PRT;   133 AA.
AC   P00167;
DT   21-JUL-1986 (REL. 01, CREATED)
DT   01-NOV-1988 (REL. 09, LAST SEQUENCE UPDATE)
DT   01-FEB-1996 (REL. 33, LAST ANNOTATION UPDATE)
DE   CYTOCHROME B5. . . .

SCORES      Init1:   127  Initn:   127  Opt:   183 z-score: 226.9 E():
5.4e-06
Smith-Waterman score: 183;    32.2% identity in 90 aa overlap

                   530       540       550       560       570       580
A-1.pdt       XLDLPTNMMEXRKAAAELXAAETAAQGPTPRYFTWDEVAQRSGCEERWLVIDRKVYNISE
                                            :|:| :|: :::  :  ||:: :|||::::
CYB5_HUMAN                          AEQSDEAVKYYTLEEIQKHNHSKSTWLILHHKVYDLTK
                                            10        20        30

                   590       600       610       620       630       640
A-1.pdt       FTRRHPGGSRVISHYAGQDATDPFVAFHINKGLVKKYMN-SLLIGELSPEQPSFEPTKNK
              | ::|||| :|: : || |||: |    ::::   : |: :::|||| |::   :|  ||
CYB5_HUMAN    FLEEHPGGEEVLREQAGGDATENFE--DVGHSTDAREMSKTFIIGELHPDD---RPKLNK
              40        50        60          70        80           90

                    650       660       670       680       690       700
A-1.pdt       ELTDEFRELRATVEQRFPVXFLTCTGAHGFFSLEVPGLPDSNKXFSWTSRPIXWNKGKRP

CYB5_HUMAN    PPETLITTIDSSSSWWTNWVIPAISAVAVALMYRLYMAED
                  100       110       120       130
```

FIG.20

FastA Match of 5' Sequence of Clone A-1 and ac004228

```
LOCUS       AC004228   170743 bp   DNA              HTG       26-FEB-1998
DEFINITION  *** SEQUENCING IN PROGRESS *** Homo sapiens Chromosome 11q12 pac
            pDJ519o3; HTGS phase 1, 18 unordered pieces.
ACCESSION   AC004228
NID         g2911733
KEYWORDS    HTG; HTGS_PHASE1. . . .

SCORES      Init1:   913 Initn:  1123 Opt:   916
   94.6% identity in 203 bp overlap

              389       379       369       359       349       339       330
A-1       CCCGACCAATATGATGGAATAAAGGAAAGCGGCCGCTGAATTATAGGCCGCCGAGACCGC
                 ||||  |  ||              ||||||||||||||||||||
ac004228  CCCGGCGCGCGGCGTCGCCAGGCCAGCTATGGCCCCCGACCCGGTGGCCGCCGAGACCGC
             60090     60100     60110     60120     60130     60140

              329       319       309       299       289       279       270
A-1       GGCTCAGGGACCTACCCCGCGTTACTTCACATGGGACGAGGTGGCCCAGCGCTCAGGGTG
          ||||||||||||||||||||||| ||||||||| ||||||||||||||||||||||||||
ac004228  GGCTCAGGGACCTACCCCGCGCTACTTCACCTGGGACGAGGTGGCCCAGCGCTCAGGGTG
             60150     60160     60170     60180     60190     60200

              269       259       249       239       229       219       210
A-1       CGAGGAGCGGTGGCTTGTGATCGACCGTAAGGTGTACAACATCAGCGAGTTCACCCGCCG
          ||||||||||||||| ||||||||||||||||||||||||||||||||||||||||||||
ac004228  CGAGGAGCGGTGGCTAGTGATCGACCGTAAGGTGTACAACATCAGCGAGTTCACCCGCCG
             60210     60220     60230     60240     60250     60260

              209       199       189       179       169       159       150
A-1       GCATCCAGGGGGCTCCCGGGTCATCAGCCACTACGCCGGGCAGGATGCCACGGATCCCTT
          ||||||||||||||||||||||||||||||||||||||||||||||||||||||
ac004228  GCATCCAGGGGGCTCCCGGGTCATCAGCCACTACGCCGGGCAGGATGCCACGGTGAGCGC
             60270     60280     60290     60300     60310     60320

              149       139       129       119       109        99        90
A-1       CGTGGCCTTCCACATCAACAAGGGCCTTGTGAAGAAGTATATGAACTCTCTCCTGATTGG

ac004228  AGCCAGGCGGGGGCACAGGAGAGGGCGGGACCGGAGGCTGAGTGCAGGGGAGACAGAGTT
             60330     60340     60350     60360     60370     60380
```

FIG. 21

FastA Match of 5' Sequence of Clone 3-5 and ac004228

```
SCORES       Init1:  1365 Initn:  2510 Opt:  1377
  98.6% identity in 285 bp overlap

                 20        30        40        50        60        70
3-5         AATACGACTCACTATAGGGCTCGAGCGGCCGCCCGGGCAGGTCCGGACCTGCCAACGTGA
                                              |||||||   | |||||||||||||||||
ac004228    CCCCGCCCCACACGCCGCATCACTTACAGGGCCCGGGGCTG-CCGGACCTGCCAACGTGA
              61710     61720     61730     61740      61750     61760

                 80        90       100       110       120       130
3-5         ATCTTATCGCCATGGACCTTACCTTGCACAACCCAAAGTAGCTGCCTTGGGGCAGGGGGT
            ||||||||||||||||||||||||||||||||||||||||||||||||||||||||||||
ac004228    ATCTTATCGCCATGGACCTTACCTTGCACAACCCAAAGTAGCTGCCTTGGGGCAGGGGGT
               61770     61780     61790     61800     61810     61820

                140       150       160       170       180       190
3-5         GGCCAGAGTGCTTAGGGAAATGTGGAGCCCTACCCAGAACAACGGTGGAGGGAAAGGGAA
            ||||||||||||||||||||||||||||||||||||||||||||||||||||||||||||
ac004228    GGCCAGAGTGCTTAGGGAAATGTGGAGCCCTACCCAGAACAACGGTGGAGGGAAAGGGAA
               61830     61840     61850     61860     61870     61880

               200       210       220       230       240       250
3-5         GAAACGCAGAAGTGCCCCAGTTCGGACGTAGGGAAGTCTTCCTCTTCGTGGTTTTTGGAG
            ||||||||||||||||||||||||||||||||||||||||||||||||||||||||||||
ac004228    GAAACGCAGAAGTGCCCCAGTTCGGACGTAGGGAAGTCTTCCTCTTCGTGGTTTTTGGAG
              61890     61900     61910     61920     61930     61940

               260       270       280       290       300       310
3-5         AACCCTAGCTAAGAGAGGAAAGGGACTTATTGAAAGACCCGCAAGAAGGGACGGAAGTCT
            ||||||||||||||||||||||||||||||||||||||||||||||||||||||||||||
ac004228    AACCCTAGCTAAGAGAGGAAAGGGACTTATTGAAAGACCCGCAAGAAGGGACGGAAGTCT
              61950     61960     61970     61980     61990     62000

               320       330       340       350       360       370
3-5         CATAGCCCTGAGAGGATCCCTTTGTGGCCTTCCACATCAACAAGGGCCTTGTGAAGAAGT
            ||||||||||||||
ac004228    CATAGCCCTGAGAGGTGAAGCCAGCTGGAGTTGATGGGTCGAATGGGGACCTAGAGAACT
              62010     62020     62030     62040     62050     62060
```

FIG.22

FastA Match of 5' Sequence of Clone A-10 and ac004228

```
SCORES      Init1:   931 Initn:  1309 Opt:   934
  97.0% identity in 200 bp overlap

            30        40        50        60        70        80        89
A-10        TATAGGGCTCGAGCGGCCGCCCGGGCAGGTGCCCGGAGGCGCCTGATCATACCTGTTGCC
                                          ||||||||||||||||||||||||||||||
ac004228    CGAGCCAAACACCGACTAATTCGGAGGAAAGCCCGGAGGCGCCTGATCATACCTGTTGCC
            60400     60410     60420     60430     60440     60450

            90        100       110       120       130       140       149
A-10        CGGTGATTGGGTGTCCTGCGGATGCGGGATGAAAAGGCGGGAGAGAGGCCTGGAAAAGTG
            |||||||||||||||||||||||||||||||||||||||||||||||||||||| |||||
ac004228    CGGTGATTGGGTGTCCTGCGGATGCGGGATGAAAAGGCGGGAGAGAGGCCTGGAGAAGTG
            60460     60470     60480     60490     60500     60510

            150       160       170       180       190       200       209
A-10        GAGTCTGGGGAGTGGGGATGGAGGCCAACAACACGCACACACAAACAAAGGGTCCCGCCT
            ||||||||||||||||||||||||||||||||||||||||||||||||||||||||||||
ac004228    GAGTCTGGGGAGTGGGGATGGAGGCCAACAACACGCACACACAAACAAAGGGTCCCGCCT
            60520     60530     60540     60550     60560     60570

            210       220       230       240       250       260       269
A-10        CCCTGCCGTGCATTCCATCTGCAGCCCCGAGCCTCAGGATCCCTTTGTGGCCTTCCACAT
            |||||||||||||||||||||||||||||||||||||| || ||   | ||
ac004228    CCCTGCCGTGCATTCCATCTGCAGCCCCGAGCCTCAGG-TCTCTGGGCGGGGACAGAACC
            60580     60590     60600     60610      60620     60630
```

FIG.23

FastA Match of 5' Sequence of Clone A-16 and ac004228

```
SCORES      Init1:   985 Initn:  1488 Opt:   997
  98.1% identity in 209 bp overlap

                   40        50        60        70        80        90
A-16        CGAGCGGCCGCCCGGGCAGGTCTAGAATTCAGCGGCCGCTGAAGCCGCGTCTGGACCTAG
                                           || ||| || | ||||||||||||||||
ac004228    AGGGAGTCACATCCTGTCTCGATGGCTAGGAGAGGCAGC-GCAGCCGCGTCTGGACCTAG
                 60720     60730     60740      60750     60760

                  100       110       120       130       140       150
A-16        GTGCCGGTCTCCACTCGCCAGCAGGAGCGGAGAGGGAGCAGGAAAGGAGCCCATTCTCGA
            ||||||||||||||||||||||||||||||||||||||||||||||||||||||||||||
ac004228    GTGCCGGTCTCCACTCGCCAGCAGGAGCGGAGAGGGAGCAGGAAAGGAGCCCATTCTCGA
        60770     60780     60790     60800     60810     60820

                  160       170       180       190       200       210
A-16        GGATGGGGCTGAAACGGGAAGCTTGGGGAGACCGCTGCCTTGGGGACCCCTGCGTCGTGT
            ||||||||||||||||||||||||||||||||||||||||||||||||||||||||||||
ac004228    GGATGGGGCTGAAACGGGAAGCTTGGGGAGACCGCTGCCTTGGGGACCCCTGCGTCGTGT
        60830     60840     60850     60860     60870     60880

                  220       230       240       250       260       270
A-16        GAAGACTGGAGGACGCGGAAGGGACAGCGCTGGCCGGGGAGGGCAAGCGGCCGCTGGCGA
            |||||||||||||||||||||||||||||||||||||||||||||||||||||||||||
ac004228    GAAGACTGGAGGACGCGGAAGGGACAGCGCTGGCCGGGGAGGGCAAGCGGCCGCTGGCGT
        60890     60900     60910     60920     60930     60940

                  280       290       300       310       320       330
A-16        TCCCTTTGTGGCCTTCCACATCAACAAGGGCCTTGTGAAGAAGTATATGAACTCTCTCCT

ac004228    ACATAAGGGATTGGGAATGGCATACACTTAGCGAGGACCCCCAGAGCTGTTCTCGAATCG
        60950     60960     60970     60980     60990     61000
```

FIG.24

FastA Match of 5' Sequence of Clone A-19 and ac004228

```
SCORES      Initl:  1227 Initn:  1409 Opt:  1532
  94.0% identity in 349 bp overlap

                     60        70        80        90        100       110
A-19           TTATTCCCTTATTTGTCCCTGCCCATGTCCTGCTGATTGGTCCATTTTACCTCTAGCTAG
                                              ||||||||||||||||||||||||||||||
ac004228       ATAGAGCACTGATTGGTCCATTTTACAGGGTGCTGATTGGTCCATTTTACCTCTAGCTAG
            63250     63260     63270     63280     63290     63300

                     120       130       140       150       160       170
A-19           CTAAAGAGCACGGATTGGTGCATTTTGCAAACCTCTGGCTACAGAGGGGTTCTCCAGGTC
               |||||||||||||||||||||||||| ||||||||| ||||||||   |||||||| |||
ac004228       CTAAAGAGCACGGATTGGTGCATTTTACAAACCTCTAGCTACAGAAAAGTTCTCCAAGTC
            63310     63320     63330     63340     63350     63360

                     180       190       200       210       220       230
A-19           TGCACTCGACCCAGGAAGTCCATCTGGCTTCACCTCTCACTTCAACTTGGGTACAGCCTT
               ||||||||||||||||||||||||||||||||||||||||||||||||||||||||||||
ac004228       TGCACTCGACCCAGGAAGTCCATCTGGCTTCACCTCTCACTTCAACTTGGGTACAGCCTT
            63370     63380     63390     63400     63410     63420

                     240       250       260       270       280       290
A-19           CTGGCGGGCAGGAAGATGGCCTTTGGTGCGAACACTGCCGGAGTCCAGGGGGCTGGCTCC
               |||||||||||| |||||||||||||||||||||||||||||||||||||||||||||||
ac004228       CTGGCGGGCAGGAGGATGGCCTTTGGTGCGAACACTGCCGGAGTCCAGGGGGCTGGCTCC
            63430     63440     63450     63460     63470     63480

                     300       310       320       330       340
A-19           CTCACCTTTCATCTTCTCCCGGCACTTGCAGGATCCCTTTGTGGCC
               ||||||||||||||||||||||||||||||||||||||||||||||
ac004228       CTCACCTTTCATCTTCTCCCGGCACTTGCAGGATCCCTTTGTGGCC
            63490     63500     63510     63520     63530
```

FIG. 25

Partial Sequence of ac004228

59751 ACTAGAACCG CTGTTCCTAC CGCGGCGCCC CCTGGGAGCC AACGCCGCGA

59801 TGCCCGCCTG ACGTCAGGAA GTCGAATCCG GCGGCGACGC TTTTAGGGAG

59851 CCCGCGAGGG GGCGCGTGTT GGCAGCCCAG CTGTGAGTTG CCCAAGACCC

59901 ACCGGGGGAC GGGATCTCGC TCCCCGCGCC ACGAGGCTCG GCCAATGGGA Possible start

59951 ACGCGCGCTG CGAGGCCCGC CGGTCTGCCC TGCGGTGCTG AAAACCCGGC

60001 GCGCAGGCGG CTGGCTCTGG GCGCGCGCCA GCAAATCCAC TCCTGGAGCC

60051 CGCGGACCCC GAGCACGCGC CTGACAGCCC CTGCTGGCCC GGCGCGCGGC

60101 GTCGCCAGGC CAGCTATGGC CCCCGACCCG GTGGCCGCCG AGACCGCGGC

60151 TCAGGGACCT ACCCCGCGCT ACTTCACCTG GGACGAGGTG GCCCAGCGCT Clone A-1

60201 CAGGGTGCGA GGAGCGGTGG CTAGTGATCG ACCGTAAGGT GTACAACATC

60251 AGCGAGTTCA CCCGCCGGCA TCCAGGGGGC TCCCGGGTCA TCAGCCACTA

60301 CGCCGGGCAG GATGCCACGG TGAGCGCAGC CAGGCGGGGG CACAGGAGAG

60351 GGCGGGACCG GAGGCTGAGT GCAGGGGAGA CAGAGTTACG CACTCCGAGC

60401 CAAACACCGA CTAATTCGGA GGAAAGCCCG GAGGCGCCTG ATCATACCTG

60451 TTGCCCGGTG ATTGGGTGTC CTGCGGATGC GGGATGAAAA GGCGGGAGAG Clone A-10

60501 AGGCCTGGAG AAGTGGAGTC TGGGGAGTGG GGATGGAGGC CAACAACACG

60551 CACACACAAA CAAAGGGTCC CGCCTCCCTG CCGTGCATTC CATCTGCAGC

60601 CCCGAGCCTC AGGTCTCTGG GCGGGGACAG AACCCCGAGC TGGGTAGGCT

60651 AGGAGGGAGG AGAGCAAGGA TGCAGGCCGC CTGGGGAGGG AGGGGGTCAG

60701 TGGCCAGGGG AGGGAGTCAC ATCCTGTCTC GATGGCTAGG AGAGGCAGCG

60751 CAGCCGCGTC TGGACCTAGG TGCCGGTCTC CACTCGCCAG CAGGAGCGGA Clone B-17

60801 GAGGGAGCAG GAAAGGAGCC CATTCTCGAG GATGGGGCTG AAACGGGAAG

60851 CTTGGGGAGA CCGCTGCCTT GGGGACCCCT GCGTCGTGTG AAGACTGGAG

60901 GACGCGGAAG GGACAGCGCT GGCCGGGGAG GGCAAGCGGC CGCTGGCGTA

FIG.26A

60951 CATAAGGGAT TGGGAATGGC ATACACTTAG CGAGGACCCC CAGAGCTGTT

61001 CTCGAATCGC CGGGGAGGCC ACTGAGCCGC AGGCCAGCGA GGTCTTCAGC

61051 TATTCCGCGG AGCGGACCGC TGTTTACGCT CTGGGGCGGT AGGCCCTTCG

61101 CGGGGTCCTG TCCCTTCTTC CCTTGGTCTC ACTGCGGGGT CGGCGCGCGC

61151 CCCAGCCCCA GGCCTGCTGC TTCCCTTTCT AGACCACAGC CCTCAGAGCT

61201 AAGGCCCCGG CGCCTCTCTG CTGGGTTGGA GTCCTGGGGA CTCAGTCCTA

61251 GGGACTCGAA AGTCGGGGCG TTCCCTTCAC CGCGTTTCCC CCTTGGCGGC

61301 CAGAATGGCG TCCCCTCCCC TTGCATCCCC CTCTGATCCC GTGCCCTGCA

61351 GCGTGATGCC CTCCACTGTC CCTATCCACT ACCCTGGCGT CCCAGAGTGT

61401 GCCGCGGGTC ACCAGGTTCC CATAACGTCG CAGCAGAGCT TAGACGCTGC

61451 GGGGCGAAGA CCCGCCCCAC CCTCTGACGC GACCAGCCTA GTGGGCGAGG

61501 CCAGAGCTTG CGCGGGTCAA CCAGAGTGAC CACTCGGGAG CCCTGACTGC

61551 GGCCAAGGGC GCAGGCGTGT CCCGGCGCAT GCGCAGACGA AACAGGCACC

61601 AACGCTGGAG CTTCCCGCAG TGTGATTTGG GGCCGGGGAT GCCGCGGCGG

61651 GGACGGCGAT TGGTCCGTAT GTGTGGTGCC ACCGGCCGCC GCTCCGCCCC

61701 GGCCCCCGCC CCACACGCCG CATCACTTAC AGGGCCCGGG GCTGCCGGAC

61751 CTGCCAACGT GAATCTTATC GCCATGGACC TTACCTTGCA CAACCCAAAG

61801 TAGCTGCCTT GGGGCAGGGG GTGGCCAGAG TGCTTAGGGA AATGTGGAGC Clone 3-5

61851 CCTACCCAGA ACAACGGTGG AGGGAAAGGG AAGAAACGCA GAAGTGCCCC

61901 AGTTCGGACG TAGGGAAGTC TTCCTCTTCG TGGTTTTTGG AGAACCCTAG

61951 CTAAGAGAGG AAAGGGACTT ATTGAAAGAC CCGCAAGAAG GGACGGAAGT

62001 CTCATAGCCC TGAGAGGTGA AGCCAGCTGG AGTTGATGGG TCGAATGGGG

62051 ACCTAGAGAA CTTTTCTGTA TCTAGAGGTT TGTAAAATGC ACCAATCAGT

62101 GCTCTGTAAA AACGCACCAA TTGGCGCTCT GTAGCTAGCT AGAGGTTTGT

62151 AAAATGAGCC AATCAGCAGG ACGTGGGCAG GGACAACTAA GACAATAAAA

62201 GCTGGCCACC CCAGCCAGCT GCTGCAACCC GCTCCAGTTC CTTACAGGC

FIG.26B

62251 TGTGGAAGCA TTGTTCTTTT GCTCGTCACA CTAAACCTTG CTGCTGCTCA

62301 TTCTTTGGGT CTGCAAAGAG TGTTATTCCT TTAAGAGCTA TAACAGCGGG

62351 AAGGTCCACG GCTCCATTCT TGAAGTCAGT GAGACCATAC CCGCCGGAAG

62401 GAACCAACGC CCGACACAGC CCCACCCATC TCTCCTGTTT CTCACCTATA

62451 CTGAAATTCT TGGGCAAAAG CTGTCTGTGG ACACACCCAG GGGAAAGGCC

62501 AGCCCAGGCA GGTGTTTCTT AGTGGTTCCC CTCAGCCAAT GCTTCCCATT

62551 CCTTGATGCA TCCTTCTAAC TAGAGCAGAT GCTCGGTGAT CTTAAACTGT

62601 GGACACCTGG GAGCACCCTC AAAAGGCAGC TGGGCCTAGG GAGATGGCCT

62651 GTGCTTCTGT GTCAGGAGTT GGTTCCTTCA GGTGGGCTTG TGGTCTCGCT

62701 GACGTCAAGA ATGAAGCCAT GAACCTTCGC GGTGAGTGTT ACAGCTCTTA

62751 CAGGTGGCGT GGACCCAAAG AGTGAGCAGC AGCAAGATTT ATTGTGAAGA

62801 GCAAAGAACA AAGCTTCCAC AGCGTGGAAG GGTACCCGAG CAGGTTGCCG

62851 CTGCTGGACG TTGGGGGGTG TGAGGGGGAG CAGCCTTTTT TTTTCTTTTT

62901 TTTTTGAGAC GGAGTCTCCC TGTCGCCCAG GCTGGAGTGC AGTGGCGCGA

62951 TCTCGGCTCA CTGCAGGCTC CGCCCCCCCC CCGGGGTTCA CGCCATTCTC

63001 CTGCCTCAGC CTCCCGAGTA GCTGGGACTA CAGGCGCCCG CTACCTCGCC

63051 CGGCTAATTT TTTGTATTTT TAGTAGAGAC GGGGTTTCAC TGTGTTAGCC

63101 AGGATGGTCT CGATCTCCTG ACCTCGTGAT CCACCCGCCT TGGCCTCCCA

63151 AAGTGCTGGG ATTACAGGCG TGAGCCACCG CGCCCGGCCG GGAGCAGCTT

63201 TTATTCCCTT ATTTGTCCCT GCCCATGTCC TGCTGATTTG TCCATTTTAT

63251 AGAGCACTGA TTGGTCCATT TTACAGGGTG CTGATTGGTC CATTTTACCT

63301 CTAGCTAGCT AAAGAGCACG GATTGGTGCA TTTTACAAAC CTCTAGCTAC

63351 AGAAAAGTTC TCCAAGTCTG CACTCGACCC AGGAAGTCCA TCTGGCTTCA

63401 CCTCTCACTT CAACTTGGGT ACAGCCTTCT GGCGGGCAGG AGGATGGCCT

63451 TTGGTGCGAA CACTGCCGGA GTCCAGGGGG CTGGCTCCCT CACCTTTCAT Clone B-19

63501 CTTCTCCCGG CACTTGCAGG ATCCCTTTGT GGCCTTCCAC ATCAACAAGG

FIG.26C

63551 GCCTTGTGAA GAAGTATATG AACTCTCTCC TGATTGGAGA ACTGTCTCCA

63601 GAGCAGCCCA GCTTTGAGCC CACCAAGAAT GTAAGACCCT GTGTTTGCTA

63651 TGTCGCAACT ATTGGTTGTT GAGGGGGACA GAGAGGGGGT GGAAGGAGAG

63701 TCTAGATGGA ATCACAGTCA TAGTAATCAC AGTCAGTAGT AGCTCTGGGG

63751 AGTCTTGAGG TCCCTGCTTC TCTTGCATAG TCATGAGGTC ACAGGCCCAA

63801 GGGAGCATGG CTTTGCAACC TATGGCTCCC CCAAGGCTGC CACTACCATG

63851 GCTGCCATCA TTGTTATCAT CATTGTTATC ATATGAGCAC TTACTATGCA

63901 CCAAGCATAA ACTCATAACT CTTACACATT TACAGATGAG ATAACAGGCT

63951 CAGGGAGGTT AAGCAACACA GCCAAGGATC ACACAGTTAG TAAATGGCAG

64001 AGCAAGGACT TAGTCCCCTG AACTCTTAGG CACTATCCCA TGGCACCTCC

64051 TCCTGTCATC CTCATTGTCG TGGTATCTTT GCCTAGGACT GTGGACTTCC

64101 CACAGCTACC TCAGTGGGAG GTCCTTGAGC CTGAGAGGGC CCTTGTCTCC

64151 AGTAGCATTG GGGTGCAGAT GAGAAGAATA ACAGCTCCTC TTCCTCTTCT

64201 GCAGAAAGAG CTGACAGATG AGTTCCGGGA GCTGCGGGCC ACAGTGGAGC

64251 GGATGGGGCT CATGAAGGCC AACCATGTCT TCTTCCTGCT GTACCTGCTG

64301 CACATCTTGC TGCTGGATGG TGCAGCCTGG CTCACCCTTT GGGTCTTTGG

64351 GACGTCCTTT TTGCCCTTCC TCCTCTGTGC GGTGCTGCTC AGTGCAGTTC

64401 AGGTGAGAGC CTTTGGCTTG TCAAGTGCAC AGCAATGCTC AGCATCCCTG

FIG.26D

FastA Match of Human D5-desaturase and
Contig 3381584

SCORES Init1: 4480 Initn: 4480 Opt: 4481
99.9% identity in 898 bp overlap

```
                                               10        20        30
human D5                              ATGGCCCCCGACCCGGTGGCCGCCGAGACC
                                      ||||||||||||||||||||||||||||||
3381584   GGCCCGGCGCGCGGCGTCGCCAGGCCAGCTATGGCCCCCGACCCGGTGGCCGCCGAGACC
              80        90       100       110       120       130

                  40        50        60        70        80        90
human D5  GCGGCTCAGGGACCTACCCCGCGCTACTTCACCTGGGACGAGGTGGCCCAGCGCTCAGGG
          ||||||||||||||||||||||||||||||||||||||||||||||||||||||||||||
3381584   GCGGCTCAGGGACCTACCCCGCGCTACTTCACCTGGGACGAGGTGGCCCAGCGCTCAGGG
             140       150       160       170       180       190

                 100       110       120       130       140       150
human D5  TGCGAGGAGCGGTGGCTAGTGATCGACCGTAAGGTGTACAACATCAGCGAGTTCACCCGC
          ||||||||||||||||||||||||||||||||||||||||||||||||||||||||||||
3381584   TGCGAGGAGCGGTGGCTAGTGATCGACCGTAAGGTGTACAACATCAGCGAGTTCACCCGC
             200       210       220       230       240       250

                 160       170       180       190       200       210
human D5  CGGCATCCAGGGGGCTCCCGGGTCATCAGCCACTACGCCGGGCAGGATGCCACGGATCCC
          ||||||||||||||||||||||||||||||||||||||||||||||||||||||||||||
3381584   CGGCATCCAGGGGGCTCCCGGGTCATCAGCCACTACGCCGGGCAGGATGCCACGGATCCC
             260       270       280       290       300       310

                 220       230       240       250       260       270
human D5  TTTGTGGCCTTCCACATCAACAAGGGCCTTGTGAAGAAGTATATGAACTCTCTCCTGATT
          ||||||||||||||||||||||||||||||||||||||||||||||||||||||||||||
3381584   TTTGTGGCCTTCCACATCAACAAGGGCCTTGTGAAGAAGTATATGAACTCTCTCCTGATT
             320       330       340       350       360       370

                 280       290       300       310       320       330
human D5  GGAGAACTGTCTCCAGAGCAGCCCAGCTTTGAGCCCACCAAGAATAAAGAGCTGACAGAT
          ||||||||||||||||||||||||||||||||||||||||||||||||||||||||||||
3381584   GGAGAACTGTCTCCAGAGCAGCCCAGCTTTGAGCCCACCAAGAATAAAGAGCTGACAGAT
             380       390       400       410       420       430

                 340       350       360       370       380       390
human D5  GAGTTCCGGGAGCTGCGGGCCACAGTGGAGCGGATGGGGCTCATGAAGGCCAACCATGTC
          ||||||||||||||||||||||||||||||||||||||||||||||||||||||||||||
3381584   GAGTTCCGGGAGCTGCGGGCCACAGTGGAGCGGATGGGGCTCATGAAGGCCAACCATGTC
             440       450       460       470       480       490
```

FIG.27A

```
                400       410       420       430       440       450
human D5   TTCTTCCTGCTGTACCTGCTGCACATCTTGCTGCTGGATGGTGCAGCCTGGCTCACCCTT
           ||||||||||||||||||||||||||||||||||||||||||||||||||||||||||||
3381584    TTCTTCCTGCTGTACCTGCTGCACATCTTGCTGCTGGATGGTGCAGCCTGGCTCACCCTT
             500       510       520       530       540       550

                460       470       480       490       500       510
human D5   TGGGTCTTTGGGACGTCCTTTTTGCCCTTCCTCCTCTGTGCGGTGCTGCTCAGTGCAGTT
           ||||||||||||||||||||||||||||||||||||||||||||||||||||||||||||
3381584    TGGGTCTTTGGGACGTCCTTTTTGCCCTTCCTCCTCTGTGCGGTGCTGCTCAGTGCAGTT
             560       570       580       590       600       610

                520       530       540       550       560       570
human D5   CAGGCCCAGGCTGGCTGGCTGCAGCATGACTTTGGGCACCTGTCGGTCTTCAGCACCTCA
           ||||||||||||||||||||||||||||||||||||||||||||||||||||||||||||
3381584    CAGGCCCAGGCTGGCTGGCTGCAGCATGACTTTGGGCACCTGTCGGTCTTCAGCACCTCA
             620       630       640       650       660       670

                580       590       600       610       620       630
human D5   AAGTGGAACCATCTGCTACATCATTTTGTGATTGGCCACCTGAAGGGGGCCCCCGCCAGT
           ||||||||||||||||||||||||||||||||||||||||||||||||||||||||||||
3381584    AAGTGGAACCATCTGCTACATCATTTTGTGATTGGCCACCTGAAGGGGGCCCCCGCCAGT
             680       690       700       710       720       730

                640       650       660       670       680       690
human D5   TGGTGGAACCACATGCACTTCCAGCACCATGCCAAGCCCAACTGCTTCCGCAAAGACCCA
           ||||||||||||||||||||||||||||||||||||||||||||||||||||||||||||
3381584    TGGTGGAACCACATGCACTTCCAGCACCATGCCAAGCCCAACTGCTTCCGCAAAGACCCA
             740       750       760       770       780       790

                700       710       720       730       740       750
human D5   GACATCAACATGCATCCCTTCTTCTTTGCCTTGGGGAAGATCCTCTCTGTGGAGCTTGGG
           ||||||||||||||||||||||||||||||||||||||||||||||||||||||||||||
3381584    GACATCAACATGCATCCCTTCTTCTTTGCCTTGGGGAAGATCCTCTCTGTGGAGCTTGGG
             800       810       820       830       840       850

                760       770       780       790       800       810
human D5   AAACAGAAGAAAAAATATATGCCGTACAACCACCAGCACAAATACTTCTTCCTAATTGGG
           ||||||||||||||||||||||||||||||||||||||||||||||||||||||||||||
3381584    AAACAGAAGAAAAAATATATGCCGTACAACCACCAGCACAAATACTTCTTCCTAATTGGG
             860       870       880       890       900       910

                820       830       840       850       860       870
human D5   CCCCCAGCCTTGCTGCCTCTCTACTTCCAGTGGTATATTTTCTATTTTGTTATCCAGCGA
           ||||||||||||||||||||||||||||||||||||||||||||||||||||||||||||
3381584    CCCCCAGCCTTGCTGCCTCTCTACTTCCAGTGGTATATTTTCTATTTTGTTATCCAGCGA
             920       930       940       950       960       970
```

FIG.27B

```
                    880       890       900       910       920       930
human D5     AAGAAGTGGGTGGACTTGGCCTGGATGATTACCTTCTACGTCCGCTTCTTCCTCACTTAT
             |||||||||||||||||||||||||| |
3381584      AAGAAGTGGGTGGACTTGGCCTGGATCAGCAAACAGGAATACGATGAAGCCGGGCTTCCA
               980       990      1000      1010      1020      1030
```

FIG.27C

FastA Match of Human D5-desaturase and
Contig 2153526

```
SCORES      Init1:  1892 Initn:  1892 Opt:  2161
  98.6% identity in 443 bp overlap

                  870       880       890       900       910       920
human D5   TCCAGCGAAAGAAGTGGGTGGACTTGGCCTGGATGATTACCTTCTACGTCCGCTTCTTCC
                                          | ||::||||||||||||||||||||||||
2153526                                   GAATKMTTACCTTCTACGTCCGCTTCTTCC
                                                  10        20        30

                  930       940       950       960       970       980
human D5   TCACTTATGTGCCACTATTGGGGCTGAAAGCCTTCCTGGGCCTTTTCTTCATAGTCAGGT
           |||||||||||||||||||||||||||||| |||||||||||||||||||||||||||||
2153526    TCACTTATGTGCCACTATTGGGGCTGAAAG-CTTCCTGGGCCTTTTCTTCATAGTCAGGT
                    40        50        60        70        80

                  990      1000      1010      1020      1030      1040
human D5   TCCTGGAAAGCAACTGGTTTGTGTGGGTGACACAGATGAACCATATTCCCATGCACATTG
           ||||||||||||||||||||||||||||||||||||||||||||||||||||||||||||
2153526    TCCTGGAAAGCAACTGGTTTGTGTGGGTGACACAGATGAACCATATTCCCATGCACATTG
           90       100       110       120       130       140

                 1050      1060      1070      1080      1090      1100
human D5   ATCATGACCGGAACATGGACTGGGTTTCCACCCAGCTCCTGGCCACATGCAATGTCCACA
           |||||||||||||||||||||||||||||||||||||||| |||||||||||||||||||
2153526    ATCATGACCGGAACATGGACTGGGTTTCCACCCAGCTCCAGGCCACATGCAATGTCCACA
          150       160       170       180       190       200

                 1110      1120      1130      1140      1150      1160
human D5   AGTCTGCCTTCAATGACTGGTTCAGTGGACACCTCAACTTCCAGATTGAGCACCATCTTT
           ||||||||||||||||||||||||||||||||||||||||||||||||||||||||||||
2153526    AGTCTGCCTTCAATGACTGGTTCAGTGGACACCTCAACTTCCAGATTGAGCACCATCTTT
          210       220       230       240       250       260

                 1170      1180      1190      1200      1210      1220
human D5   TTCCCACGATGCCTCGACACAATTACCACAAAGTGGCTCCCCTGGTGCAGTCCTTGTGTG
           ||||||||||||||||||||||||||||||||||||||||||||||||||||||||||||
2153526    TTCCCACGATGCCTCGACACAATTACCACAAAGTGGCTCCCCTGGTGCAGTCCTTGTGTG
          270       280       290       300       310       320

                 1230      1240      1250      1260      1270      1280
human D5   CCAAGCGTGGCATAGAGTACCAGTCCAAGCCCCTGCTGTCAGCCTTCGCCGACATCATCC
           |||||| |||||||||||||||||||||||||||||||||||||||||||||||||||||
2153526    CCAAGCATGGCATAGAGTACCAGTCCAAGCCCCTGCTGTCAGCCTTCGCCGACATCATCC
          330       340       350       360       370       380
```

FIG.28A

```
              1290      1300      1310      1320      1330
human D5   ACTCACTAAAGGAGTCAGGGCAGCTCTGGCTAGATGCCTATCTTCACCAATAA
           |||||||||||||||||||||||||||||||||||||||||||||||||||||
2153526    ACTCACTAAAGGAGTCAGGGCAGCTCTGGCTAGATGCCTATCTTCACCAATAACAACAGC
          390       400       410       420       430       440
```

FIG.28B

FastA Match of Human D5-desaturase and
Contig 253538a

```
SCORES     Init1:  1479 Initn:  2483 Opt:  2489
Smith-Waterman score: 2489;    81.3% identity in 434 aa overlap

                   10        20        30        40        50        60
human D5   MAPDPVAAETAAQGPTPRYFTWDEVAQRSGCEERWLVIDRKVYNISEFTRRHPGGSRVIS
                       ||||||||||||||||||||||||||||||||||||||||||||||||
253538a                QGPTPRYFTWDEVAQRSGCEERWLVIDRKVYNISEFTRRHPGGSRVIS
                                 10        20        30        40

                   70        80        90       100       110       120
human D5   HYAGQDATDPFVAFHINKGLVKKYMNSLLIGELSPEQPSFEPTKNKELTDEFRELRATVE
           ||||||||||||||||||||||||||||||||||||||||||||||||||||||||||||
253538a    HYAGQDATDPFVAFHINKGLVKKYMNSLLIGELSPEQPSFEPTKNKELTDEFRELRATVE
            50        60        70        80        90       100

                  130       140       150       160       170       180
human D5   RMGLMKANHVFFLLYLLHILLLDGAAWLTLWVFGTSFLPFLLCAVLLSAVQAQAGWLQHD
           ||||||||||||||||||||||||||||||||||||||||||||||||||||||||||||
253538a    RMGLMKANHVFFLLYLLHILLLDGAAWLTLWVFGTSFLPFLLCAVLLSAVQAQAGWLQHD
          110       120       130       140       150       160

                  190       200       210       220       230       239
human D5   FGHLSVFSTSKWNHLLHHFVIGHLKGAPASWWNHMHFQHHAKPNCFRKDPDINM-HPFFF
           :|||||:   |||||:|:||||||||| |:|||| ||||||||| |:||||:|| |   |
253538a    YGHLSVYRKPKWNHLVHKFVIGHLKGASANWWNHRHFQHHAKPNIFHKDPDVNMLH--VF
          170       180       190       200       210       220

          240       250       260       270       280       290      299
human D5   ALGKILSVELGKQKKKYMPYNHQHKYFFLIGPPALLPLYFQWYIFYFVIQRKKWVDLAWM
           :||:   :| ||:| ||:||||||:|||||||| |:|:|||: |:: :| :|:|||||| 
253538a    VLGEWQPIEYGKKKLKYLPYNHQHEYFFLIGPPLLIPMYFQYQIIMTMIVHKNWVDLAWA
             230       240       250       260       270       280

          300       310       320       330       340       350
human D5   ITFYVRFFLTYVPLLG-LKAFLGLFFIVRFLESNWFVWVTQMNHIPMHIDHDRNMDWVST
           :::|:|||:||:|: | | |:| | || |||||:||||||||||| |:||::   || |:
253538a    VSYYIRFFITYIPFYGILGALLFLNFI-RFLESHWFVWVTQMNHIVMEIDQEAYRDWFSS
             290       300       310       320       330       340

           360       370       380       390       400       410
human D5   QLLATCNVHKSAFNDWFSGHLNFQIEHHLFPTMPRHNYHKVAPLVQSLCAKRGIEYQSKP-
           || |||||::| ||||||||||||||||||||||||| ||:||||:|||||:||||| ||
253538a    QLTATCNVEQSFFNDWFSGHLNFQIEHHLFPTMPRHNLHKIAPLVKSLCAKHGIEYQEKP
              350       360       370       380       390       400
```

FIG.29A

```
                    420       430       440
human D5      LLSAFADIIHSLKESGQLWLDAYLHQX
              || |: |||:|||:||:||||||||:|
253538a       LLRALLDIIRSLKKSGKLWLDAYLHKXSHSPRDTVGKGCRWGDGQRNDGLLFXGVSERLV
                  410       420       430       440       450       460
```

FIG.29B

FastA Match of Human D5-desaturase and Contig 38

```
SCORES       Init1:  2024 Initn:  2024 Opt:  2026
Smith-Waterman score: 2026;    99.3% identity in 287 aa overlap

                      10        20        30        40        50        60
human D5     MAPDPVAAETAAQGPTPRYFTWDEVAQRSGCEERWLVIDRKVYNISEFTRRHPGGSRVIS
                         ||||||||||||||||||||||||||||||||||||||||||||||||
38                       QGPTPRYFTWDEVAQRSGCEERWLVIDRKVYNISEFTRRHPGGSRVIS
                                 10        20        30        40

                      70        80        90       100       110       120
human D5     HYAGQDATDPFVAFHINKGLVKKYMNSLLIGELSPEQPSFEPTKNKELTDEFRELRATVE
             ||||||||||||||||||||||||||||||||||||||||||||||||||||||||||||
38           HYAGQDATDPFVAFHINKGLVKKYMNSLLIGELSPEQPSFEPTKNKELTDEFRELRATVE
              50        60        70        80        90       100

                     130       140       150       160       170       180
human D5     RMGLMKANHVFFLLYLLHILLLDGAAWLTLWVFGTSFLPFLLCAVLLSAVQAQAGWLQHD
             ||||||||||||||||||||||||||||||||||||||||||||||||||||||||||||
38           RMGLMKANHVFFLLYLLHILLLDGAAWLTLWVFGTSFLPFLLCAVLLSAVQAQAGWLQHD
            110       120       130       140       150       160

                     190       200       210       220       230       240
human D5     FGHLSVFSTSKWNHLLHHFVIGHLKGAPASWWNHMHFQHHAKPNCFRKDPDINMHPFFFA
             ||||||||||||||||||||||||||||||||||||||||||||||||||||||||||||
38           FGHLSVFSTSKWNHLLHHFVIGHLKGAPASWWNHMHFQHHAKPNCFRKDPDINMHPFFFA
            170       180       190       200       210       220

                     250       260       270       280       290       300
human D5     LGKILSVELGKQKKKYMPYNHQHKYFFLIGPPALLPLYFQWYIFYFVIQRKKWVDLAWMI
             ||||||||||||||||||||||| ||||||||||||||||||||||||||||||||||:
38           LGKILSVELGKQKKKYMPYNHQHXYFFLIGPPALLPLYFQWYIFYFVIQRKKWVDLAWIS
            230       240       250       260       270       280

                     310       320       330       340       350       360
human D5     TFYVRFFLTYVPLLGLKAFLGLFFIVRFLESNWFVWVTQMNHIPMHIDHDRNMDWVSTQL

38           KQEYDEAGLPLSTANASKRDLPRATSPGTRWPSAQGARSGGXXSTVRCTTSASSPAGIQG
            290       300       310       320       330       340
```

FIG.30

FastA Match of D6-Desaturase (Ma524) and
Human D5-Desaturase

```
SCORES      Init1:   280 Initn:   601 Opt:   303
Smith-Waterman score: 697;    30.5% identity in 455 aa overlap

                   10        20            30            40        50
human D5   MAPDPVAAETAAQGPTPRYFTWDEV----AQRSGCCEER----WLVIDRKVYNISEFTRRH
                     | :|: | || ||    |   | ::     ::|| |||:: ||: |
Ma524.pep            MAAAPSVRTFTRAEVLNAEALNEGKKDAEAPFLMIIDNKVYDVREFVPDH
                             10        20        30        40        50

                 60        70        80        90       100       110
human D5   PGGSRVISHYAGQDATDPFVAFHINKGLVKKYMNSLLIGELSPEQPSFEPTKNKELTDEF
           |||| :::| :|:|:|| | :|| : :   : : :: :|:::    | :  || ::: |
Ma524.pep  PGGSVILTH-VGKDGTDVFDTFHPEAAW--ETLANFYVGDIDE---SDRDIKNDDFAAEV
              60        70          80        90           100

              120       130       140       150          160       170
human D5   RELRATVERMGLMKANHVFFLLYLLHILLLDGAAWLTLWVFG-TSFLPFLLCAVLLSAVQ
           |:||:  : :| : :::::: : :   | : | : : :  :| || |   :| |:||:
Ma524.pep  RKLRTLFQSLGYYDSSKAYYAFKVSFNLCIWGLSTVIVAKWGQTSTLANVLSAALLGLFW
             110       120       130       140       150       160

                180       190       200       210       220       230
human D5   AQAGWLQHDFGHLSVFSTSKWNHLLHHFVIGHLKGAPASWWNHMHFQHHAKPNCFRKDPD
            | ||| ||| | :||:     |: |:  |: |  :|  :|||:  |  ||| ||   :|||
Ma524.pep  QQCGWLAHDFLHHQVFQDRFWGDLFGAFLGGVCQGFSSSWWKDKHNTHHAAPNVHGEDPD
             170       180       190       200       210       220

                 240           250       260       270       280
human D5   INMHPFF----FALGKILSV---ELGKQKKKYMPYNHQHKYFFLIGPPALLPLYFQWYIF
           |: ||::      ||   : :|    || :: :::| | |  ::| |   | |    :|  :|
Ma524.pep  IDTHPLLTWSEHALEMFSDVPDEELTRMWSRFMVLN-QTWFYFPILSFARLSWCLQSILF
             230       240       250       260        270       280

                          290       300       310         320      329
human D5   YFV-------------IQRKKWVDLAWMITFYVRFFLTYV--PLLGLKAFLGLFFIVRFL
            :              |:  : ::||   |:|:  :: ::  |:       :|  |:: : :
Ma524.pep  VLPNGQAHKPSGARVPISLVEQLSLAMHWTWYLATMFLFIKDPV----NMLVYFLVSQAV
              290       300       310       320          330

          330       340         350       360       370       380
human D5   ESNWFVWVTQMNHIPMHI---DHDRNMDWVSTQLLATCNVHKSAFNDWFSGHLNFQIEHH
            :| :: | ::||   | :     ::  :||: : |:::  :|| : | :||:| ||:|||||
Ma524.pep  CGNLLAIVFSLNHNGMPVISKEEAVDMDFFTKQIITGRDVHPGLFANWFTGGLNYQIEHH
          340       350       360       370       380       390
```

FIG.31A

```
                390       400       410       420       430       440
human D5     LFPTMPRHNYHKVAPLVQSLCAKRGIEYQSKPLLSAFADIIHSLKESGQLWLDAYLHQX
             |||:|||||: |: | |::|| | :::|::  :: : |:::  |:|
Ma524.pep    LFPSMPRHNFSKIQPAVETLCKKYNVRYHTTGMIEGTAEVFSRLNEVSKAASKMGKAQX
            400       410       420       430       440       450
```

FIG.31B

FastA Match of D5-Desaturase (Ma29) and
Human D5-Desaturase

```
SCORES      Init1:   145 Initn:   236 Opt:   266
Smith-Waterman score: 400;    27.5% identity in 455 aa overlap

                   10        20        30        40        50        60
human D5    MAPDPVAAETAAQGPTPRYFTWDEVAQRSGCEERWLVIDRKVYNISEFTRRHPGGSRVIS
                       || |    |||:|:| ::  ::  |:|  :||::::|  |||||  ::
Ma29.pep           MGTDQGKT---FTWEELAAHNTKDDLLLAIRGRVYDVTKFLSRHPGGVDTLL
                              10        20        30        40

                   70        80        90       100       110
human D5    HYAGQDATDPFVAFHINKGLVKKYMNSLLIGEL-SPEQPSF-EPTKNKELTDEFRELRAT
             ||:|:|  |  :|   | :   |::  :| | | | | | |||  ::      |   |
Ma29.pep    LGAGRDVTPVFEMYHAF-GAADAIMKKYYVGTLVSNELPIFPEPTVFHKTIKTRVEGYFT
           50        60        70        80        90       100

           120       130        140       150       160       170
human D5    VERMGLMKANHVF--FLLYLLHILLLDGAAWLTLWVFGTSFLPFLLCAVLLSAVQAQAGW
             : :   :  :::  : | :  ::    |  :: :|   ::|  :: |:::: : ||:|
Ma29.pep    DRNIDPKNRPEIWGRYALIFGSLIASYYAQLFVPFVVERTWLQVVF-AIIMGFACAQVGL
           110       120       130       140       150        160

              180       190        200       210        220       230
human D5    LQ-HDFGHLSV-FSTSKWNHL--LHHFVIGHLKGAPASWWNHMH-FQHHAKPNCFRKDPD
               || :|:||  : : |: |   | |    ::||   | ::| : ||   |    |||
Ma29.pep    NPLHDASHFSVTHNPTVWKILGATHDF----FNGASYLVWMYQHMLGHHPYTNIAGADPD
            170       180       190           200       210       220

                  240       250       260          270       280
human D5    INM-HPFFFALGKILSVELGKQKKKYMPYNH--QHKYF-FLIGPPALLPLYFQWYIFYFV
            ::  :|          :|:  | ::|::  ||  || :  || |  |:     :  |:|||
Ma29.pep    VSTSEP---------DVRRIKPNQKWF-VNHINQHMFVPFLYGLLAFKVRIQDINILYFV
                         230       240        250       260       270

               290       300         310           320       330
human D5    IQ----RKKWVDLAWMITFY--VRFFLTY---VPL--LGLKAFLGLFFIVRFLESNWFVW
                  | : ::     : |:    ||: |   |||  | |   | || :: :: | |::
Ma29.pep    KTNDAIRVNPISTWHTVMFWGGKAFFVWYRLIVPLQYLPLGKVLLLFTVADMVSSYWLAL
               280       290       300       310       320       330

              340       350         360       370       380
human D5    VTQMNHIPMHID---HDRN----MDWVSTQLLATCN-VHKSAFNDWFSGHLNFQIEHHLF
            : | ||:  :::      |:|     ||:: |: :| : :| | :    ::| ||:|  ||||
Ma29.pep    TFQANHVVEEVQWPLPDENGIIQKDWAAMQVETTQDYAHDSHLWTSITGSLNYQAVHHLF
               340       350       360       370       380       390
```

FIG.32A

```
             390       400       410       420         430       440
human D5     PTMPRHNYHKVAPLVQSLCAKRGIEYQSKPLL-SAFADIIHSLKESGQLWLDAYLHQX
             |:: :|:|  :  :::: |::  : |  |  : :|||: :: |:  |
Ma29.pep     PNVSQHHYPDILAIIKNTCSEYKVPYLVKDTFWQAFASHLEHLRVLGLRPKEEX
                 400       410       420       430       440
```

FIG.32B

| HOST(PLASMID) | 334(pRAE-28-5) | 334(pRAE-26-1) | 334(pRAE-33) | 334(pRAE-35) | 334(pYX242) |
|---|---|---|---|---|---|
| ADDED SUBSTRATE | 25 μM DGLA | 25 μM DGLA | 25 μM DGLA | 25 μM DGLA | 25 μM DGLA |
| | | | 30° C/48hrs | | |
| FATTY ACID | | (g FATTY ACID/100 g FATTY ACID) lipid (μg) | | | |
| C16:0 | 151.580 | 202.175 | 285.291 | 281.298 | 304.229 |
| C16:1 | 406.279 | 185.631 | 552.951 | 569.298 | 608.123 |
| C18:0 | 16.494 | 25.995 | 32.162 | 27.479 | 30.093 |
| C18:1n-9 | 100.031 | 133.349 | 173.772 | 184.740 | 187.780 |
| C18:2n-6 | | 0.180 | | | 0.946 |
| C18:3n-6 | | 0.058 | 0.074 | | 0.074 |
| C20:0 | 3.844 | 4.205 | 7.118 | 7.285 | 6.288 |
| **C20:3n-6** | **96.576** | **118.657** | **134.859** | **139.292** | **125.448** |
| **C20:4n-6** | **(0.127%) 1.204** | **(0.075%) 0.878** | **(0.062%) 0.902** | **(0.063%) 0.927** | **(0.062%) 0.958** |
| C22:0 | | 0.150 | 0.119 | | 0.125 |
| C22:1n-9 | 0.162 | 0.139 | 0.299 | 0.275 | 0.392 |
| TOTAL LIPID | 949.0 | 1169.0 | 1445.5 | 1468.0 | 1538.5 |

FIG.33

| HOST(PLASMID) | 334(pRAE-28-5) | 334(pRAE-26-1) | 334(pYX242) | 334(pRAE-28-5) | 334(pRAE-26-1) | 334(pYX242) | 334(pRAE-28-5) | 334(pRAE-26-1) | 334(pYX242) |
|---|---|---|---|---|---|---|---|---|---|
| ADDED SUBSTRATE | 25 μM DGLA | 25 μM DGLA | 25 μM DGLA | 25 μM OA | 25 μM OA | 25 μM OA | 25 μM AA | 25 μM AA | 25 μM AA |
| | | | 30 °C/48hrs | | | | | | 30 °C/48hrs |
| FATTY ACID | | (g FATTY ACID/100 g FATTY ACID) lipid (μg) | | | | | | | |
| C16:0 | 49.332 | 106.358 | 93.225 | 84.327 | 37.013 | 51.018 | 78.471 | 53.685 | 74.099 |
| C16:1 | 141.178 | 256.622 | 277.028 | 269.009 | 107.066 | 172.485 | 230.45 | 141.526 | 181.298 |
| C18:0 | 9.301 | 14.819 | 12.908 | 11.871 | 8.3 | 9.047 | 11.283 | 9.97 | 10.969 |
| C18:1n-9 | 39.876 | 87.564 | 72.842 | **106.416** | **52.634** | **71.453** | 61.754 | 42.289 | 46.873 |
| C18:2n-6 | | | | **ND** | **ND** | **ND** | | | |
| C18:3n-6 | | | | | | | | | |
| C20:0 | 2.154 | 7.339 | | | 3.729 | | | 2.685 | |
| C20:3n-6 | **45.395** | **56.346** | **55.306** | | | | | | |
| C20:4n-6 | **(0.106%) 0.412** | **(0.060%) 0.396** | **(0.065%) 0.402** | | | | **63.584** | **68.442** | **60.89** |
| C22:5n-3 | | | | | | | **(0.026%) 0.139** | **(0.019%) 0.077** | **(0.027%) 0.126** |
| TOTAL LIPID | 387 | 665 | 620 | 562 | 284 | 363 | 535 | 404 | 466 |

FIG.34A

| HOST(PLASMID) | 334(pRAE-28-5) | 334(pRAE-26-1) | 334(pRAE-33) | 334(pRAE-35) | 334(pRAE-26-1) | 334(pYX242) |
|---|---|---|---|---|---|---|
| ADDED SUBSTRATE | 25 μM LA | 25 μM LA | 25 μM LA | NO SUBSTRATE | NO SUBSTRATE | NO SUBSTRATE |
| | | | 30° C/48hrs | | | |
| FATTY ACID | | (g FATTY ACID/100 g FATTY ACID) lipid (μg) | | | | |
| C16:0 | 56.631 | 45.393 | 74.247 | 174.138 | 25.574 | 33.44 |
| C16:1 | 181.311 | 117.045 | 208.029 | 277.122 | 43.193 | 47.189 |
| C18:0 | 9.549 | 9.251 | 11.45 | 22.547 | 5.119 | 8.432 |
| C18:1n-9 | 48.256 | 46.496 | 51.342 | 134.822 | 21.89 | 32.618 |
| C18:2n-6 | **31.91** | **23.221** | **36.821** | | | |
| C18:3n-6 | **(0.02%) 0.082** | **ND** | **(0.012%) 0.056** | | | |
| C20:0 | | 0.339 | | 0.702 | | |
| C20:3n-6 | | | | | | |
| C20:4n-6 | | | | | | |
| C20:5n-3 | 0.121 | | | | | |
| TOTAL LIPID | 407 | 279 | 460 | 746 | 127 | 168 |

FIG.34B

HUMAN DESATURASE GENE AND USES THEREOF

The subject application is a Continuation-In-Part of pending U.S. patent application Ser. No. 09/227,613 filed on Jan. 8, 1999, which is a Continuation-In-Part of pending International Application PCT/US98/07422 filed on Apr. 10, 1998 (which designates the U.S.) which is a Continuation-In-Part of U.S. patent application Ser. No. 08/833,610 filed on Apr. 11, 1997, now U.S. Pat. No. 5,972,664 all of which are incorporated herein in their entirety by reference.

BACKGROUND OF THE INVENTION

1. Technical Field

The subject invention relates to the identification and isolation of a gene that encodes an enzyme (i.e., human Δ5-desaturase) involved in the synthesis of polyunsaturated fatty acids and to uses thereof. In particular, Δ5-desaturase VQ catalyzes the conversion of, for example, dihomo-γ-linolenic acid (DGLA) to arachidonic acid (AA) and (n-3)-eicosatetraenoic acid (20:4n-3) to eicosapentaenoic acid (20:5n-3). The converted product may then be utilized as a substrate in the production of other polyunsaturated fatty acids (PUFAs). The product or other polyunsaturated fatty acids may be added to pharmaceutical compositions, nutritional composition, animal feeds as well as other products such as cosmetics.

2. Background Information

Desaturases are critical in the production of long-chain polyunsaturated fatty acids which have many important functions. For example, PUFAs are important components of the plasma membrane of a cell, where they are found in the form of phospholipids. They also serve as precursors to mammalian prostacyclins, eicosanoids, leukotrienes and prostaglandins. Additionally, PUFAs are necessary for the proper development of the developing infant brain as well as for tissue formation and repair. In view of the biological significance of PUFAs, attempts are being made to produce them, as well as intermediates leading to their production, in an efficient manner.

A number of enzymes are involved in PUFA biosynthesis including Δ5-desaturase (see FIG. 11). For example, elongase (elo) catalyzes the conversion of γ-linolenic acid (GLA) to dihomo-γ-linolenic acid (DGLA) and of stearidonic acid (18:4n-3) to (n-3)-eicosatetraenoic acid (20:4n-3). Linoleic acid (LA, 18:2-Δ9,12 or 18:2n-6) is produced from oleic acid (18:1-Δ9) by a Δ12-desaturase. GLA (18:3-Δ6,9,12) is produced from linoleic Δ5 acid by a Δ6-desaturase.

It must be noted that animals cannot desaturate beyond the Δ9 position and therefore cannot convert oleic acid into linoleic acid. Likewise, α-linolenic acid (ALA, 18:3-Δ9,12, 15) cannot be synthesized by mammals. However, α-linolenic acid can be converted to stearidonic acid (STA, 18:4-Δ6,9,12,15) by a Δ6-desaturase (see PCT publication WO 96/13591 and *The Faseb Journal,* Abstracts, Part I, Abstract 3093, page A532 (Experimental Biology 98, San Francisco, Calif., Apr. 18–22, 1998) see also U.S. Pat. No. 5,552,306), followed by elongation to (n-3)-eicosatetraenoic acid (20:4-Δ8,11,14,17) in mammals and algae. This polyunsaturated fatty acid (i.e., 20:4-Δ8,11,14,17) can then be converted to eicosapentaenoic acid (EPA, 20:5-Δ5,8,11,14, 17) by a Δ5-desaturase, such as that of the present invention. Other eukaryotes, including fungi and plants, have enzymes which desaturate at carbon 12 (see PCT publication WO 94/11516 and U.S. Pat. No. 5,443,974) and carbon 15 (see PCT publication WO 93/11245). The major polyunsaturated fatty acid of animals therefore are either derived from diet and/or from desaturation and elongation of linoleic acid or α-linolenic acid. In view of these difficulties, it is of significant interest to isolate genes involved in PUFA synthesis from species that naturally produce these fatty acids and to express these genes in a microbial, plant, or animal system which can be altered to provide production of commercial quantities of one or more PUFAs. One of the most important long chain PUFAs, noted above, is arachidonic acid (AA). AA is found in filamentous fungi and can also be purified from mammalian tissues including the liver and adrenal glands. As noted above, AA production from dihomo-γ-linolenic acid is catalyzed by a Δ5-desaturase. EPA is another important long-chain PUFA. EPA is found in fungi and also in marine oils. As noted above, EPA is produced from (n-3)-eicosatetraenoic acid and is catalyzed by a Δ5-desaturase.

In view of the above discussion, there is a definite need for the Δ5-desaturase enzyme, the gene encoding this enzyme, as well as recombinant methods of producing this enzyme. Additionally, a need exists for oils containing levels of PUFAs beyond those naturally present as well as those enriched in novel PUFAs. Such oils can only be made by isolation and expression of the Δ5-desaturase gene.

All U.S. patents and publications referred to herein are hereby incorporated in their entirety by reference.

SUMMARY OF THE INVENTION

The present invention includes an isolated nucleotide sequence corresponding to or complementary to at least about 50% of the nucleotide sequence shown in SEQ ID NO:1 (FIG. 12). The isolated nucleotide sequence may be represented by SEQ ID NO:1. These sequences may encode a functionally active desaturase which utilizes a polyunsaturated fatty acid as a substrate. The sequences may be derived from a mammal such as, for example, a human.

The present invention also includes purified proteins encoded by the nucleotide sequences referred to above. Additionally, the present invention includes a purified polypeptide which desaturates polyunsaturated fatty acids at carbon 5 and has at least about 50% amino acid similarity to the amino acid sequence of the purified proteins referred to directly above.

Furthermore, the present invention also encompasses a method of producing a human Δ5-desaturase. This method comprises the steps of: a) isolating the nucleotide sequence represented by SEQ ID NO:1 (FIG. 12); b) constructing a vector comprising: i) the isolated nucleotide sequence operably linked to ii) a promoter; and c) introducing the vector into a host cell under time and conditions sufficient for expression of the human Δ5-desaturase. The host cell may be, for example, a eukaryotic cell or a prokaryotic cell. In particular, the prokaryotic cell may be, for example, *E. coli,* cyanobacteria or *B. subtilis.* The eukaryotic cell may be, for example, a mammalian cell, an insect cell, a plant cell or a fungal cell (e.g., a yeast cell such as *Saccharomyces cerevisiae, Saccharomyces carlsbergensis,* Candida spp., *Lipomyces starkey, Yarrowia lipolytica,* Kluvveromyces spp., Hansenula Spp., Trichoderma spp. or Pichia spp.).

Additionally, the present invention also encompasses a vector comprising: a) a nucleotide sequence as represented by SEQ ID NO:1 (FIG. 12) operably linked to b) a promoter. The invention also includes a host cell comprising this vector. The host cell may be, for example, a eukaryotic cell or a prokaryotic cell. Suitable eukaryotic cells and prokaryotic cells are as defined above.

Moreover, the present invention also includes a plant cell, plant or plant tissue comprising the above vector, wherein expression of the nucleotide sequence of the vector results in production of a polyunsaturated fatty acid by the plant cell, plant or plant tissue. The polyunsaturated fatty acid may be, for example, selected from the group consisting of AA and EPA. The invention also includes one or more plant oils or acids expressed by the above plant cell, plant or plant tissue.

Additionally, the present invention also encompasses a transgenic plant comprising the above vector, wherein expression of the nucleotide sequence of the vector results in production of a polyunsaturated fatty acid in seeds of the transgenic plant.

Also, the invention includes a mammalian cell comprising the above vector wherein expression of the nucleotide sequence of the vector results in production of altered levels of AA or EPA when the cell is grown in a culture media comprising a fatty acid selected from the group consisting of an essential fatty acid, LA and ALA.

It should also be noted that the present invention encompasses a transgenic, non-human mammal whose genome comprises a DNA sequence encoding a human Δ5-desaturase operably linked to a promoter. The DNA sequence may be represented by SEQ ID NO:1 (FIG. 12). Additionally, the present invention includes a fluid (e.g., milk) produced by the transgenic, non-human mammal wherein the fluid comprises a detectable level of at least human Δ5-desaturase.

Additionally, the present invention includes a method (i.e., "first" method) for producing a polyunsaturated fatty acid comprising the steps of: a) isolating the nucleotide sequence represented by SEQ ID NO:1 (FIG. 12); b) constructing a vector comprising the isolated nucleotide sequence; c) introducing the vector into a host cell under time and conditions sufficient for expression of the human Δ5-desaturase enzyme; and d) exposing the expressed human Δ5-desaturase enzyme to a substrate polyunsaturated fatty acid in order to convert the substrate to a product polyunsaturated fatty acid. The substrate polyunsaturated fatty acid may be, for example, DGLA or 20:4n-3 and the product polyunsaturated fatty acid may be, for example, AA or EPA, respectively. This method may further comprise the step of exposing the product polyunsaturated fatty acid to an elongase in order to convert the product polyunsaturated fatty acid to another polyunsaturated fatty acid (i.e., "second" method). In this method containing the additional step (i.e., "second" method), the product polyunsaturated fatty acid may be, for example, AA or EPA, and the "another" polyunsaturated fatty acid may be adrenic acid or (n-3)-docosapentaenoic acid, respectively. The method containing the additional step may further comprise a step of exposing the another polyunsaturated fatty acid to an additional desaturase in order to convert the another polyunsaturated fatty acid to a final polyunsaturated fatty acid (i.e., "third" method). The final polyunsaturated fatty acid may be, for example, (n-6)-docosapentaenoic acid or docosahexaenoic (DHA) acid.

The present invention also encompasses a nutritional composition comprising at least one polyunsaturated fatty acid selected from the group consisting of the product polyunsaturated fatty acid produced according to the "first" method, another polyunsaturated fatty acid produced according to the "second" method, and the final polyunsaturated fatty acid produced according to the "third" method. The product polyunsaturated fatty acid may be, for example, AA or EPA. The another polyunsaturated fatty acid may be, for example, adrenic acid or (n-3)-docosapentaenoic acid. The final polyunsaturated fatty acid may be, for example, (n-6)-docosapentaenoic acid or DHA. This nutritional composition, may be, for example, an infant formula, a dietary supplement or a dietary substitute and may be administered to a human or to an animal. It may be administered enterally or parenterally. The nutritional composition may further comprise at least one macronutrient selected from the group consisting of coconut oil, soy oil, canola oil, monoglycerides, diglycerides, glucose, edible lactose, electrodialysed whey, electrodialysed skim milk, milk whey, soy protein, and protein hydrolysates. Additionally, the composition may further comprise at least one vitamin selected from the group consisting of Vitamins A, C, D, E, and B complex and at least one mineral selected from the group consisting of calcium magnesium, zinc, manganese, sodium, potassium, phosphorus, copper, chloride, iodine, selenium and iron.

Furthermore, the present invention also includes a a pharmaceutical composition comprising 1) at least one polyunsaturated fatty acid selected from the group consisting of the product polyunsaturated fatty acid produced according to the "first" method, the another polyunsaturated fatty acid produced according to the "second" method, and the final polyunsaturated fatty acid produced according to the "third" method and 2) a pharmaceutically acceptable carrier. Again, the pharmaceutical composition may be administered to a human or to an animal. The composition may further comprise an element selected from the group consisting of a vitamin, a mineral, a carbohydrate, an amino acid, a free fatty acid, a phospholipid, an antioxidant, and a phenolic compound.

Additionally, the present invention includes an animal feed comprising at least one polyunsaturated fatty acid selected from the group consisting of the product polyunsaturated fatty acid produced according to the first method, the another polyunsaturated fatty acid produced according to the second method and the final polyunsaturated fatty acid produced according to the third method. The product polyunsaturated fatty acid may be, for example, AA or EPA. The another polyunsaturated fatty acid may be, for example, adrenic acid or (n-3)-docosapentaenoic acid. The final polyunsaturated fatty acid may be, for example, (n-6)-docosapentaenoic acid or DHA.

Moreover, the present invention also includes a cosmetic comprising a polyunsaturated fatty acid selected from the group consisting of the product polyunsaturated fatty acid produced according to the first method, the another polyunsaturated fatty acid produced according to the second method, and the final polyunsaturated fatty acid produced according to the third method.

Additionally, the present invention encompasses a method of preventing or treating a condition caused by insufficient intake of polyunsaturated fatty acids comprising administering to the patient the nutritional composition of above in an amount sufficient to effect prevention or treatment.

BRIEF DESCRIPTION OF THE DRAWINGS

FIG. 1 outlines the sections of the *M. alpina* Δ5- and Δ6-desaturases, the clone ID's from the LifeSeq database to which those sections had homology, and the keyword associated with the clone ID's.

FIG. 2 represents the contig 2692004 (SEQ ID NO:2).

FIG. 3 represents the contig 2153526 (SEQ ID NO:3).

FIG. 4 represents the contig 3506132 (SEQ ID NO:4).

FIG. 5 represents the contig 3854933 (SEQ ID NO:5).

FIG. 6 represents the contig 2511785 (SEQ ID NO:6).

FIG. 7 represents the contig 2535 (SEQ ID NO:7) generated based on contig 2511785 of FIG. 6 and contig 3506132 of FIG. 4.

FIG. 8 represents the contig 253538a (SEQ ID NO:8) generated based on contig 2535 of FIG. 7 and contig 3854933 of FIG. 5.

FIG. 9 represents the amino acid sequence identity between the *M. alpina* Δ5-desaturase (Ma29) and the contig 253538a (SEQ ID NO:9).

FIG. 10 represents the amino acid sequence identity between the *M. alpina* Δ6-desaturase (Ma524) (SEQ ID NO:10) and the contig 253538a (SEQ ID NO:9).

FIG. 12 represents the complete nucleotide sequence of the human Δ5-desaturase gene (human Δ5) (SEQ ID NO:1).

FIG. 13 represents the amino acid sequence of the human Δ5-desaturase (SEQ ID NO:11) translated from human Δ5 (see FIG. 12).

FIG. 15 represents the complete putative human desaturase gene sequence (SEQ ID NO:12) from clone pRAE-7 and the corresponding, translated amino acid sequence (SEQ ID NO:13).

FIG. 16 illustrates the amino acid sequence identity between the putative human desaturase gene in pRAE-7 (SEQ ID NO:14) and the *M. alpina* Δ5-desaturase (SEQ ID NO:15).

FIG. 17 illustrates the amino acid sequence identity between the putative human desaturase gene in pRAE-7 (SEQ ID NO:16) and the *M. alpina* Δ6-desaturase (SEQ ID NO:18).

FIG. 18 illustrates the amino acid sequence identity between the putative human desaturase gene in pRAE-7 (SEQ ID NO:18) and the contig 2535 (SEQ ID NO:19).

FIG. 19 illustrates the amino acid sequence identity between the putative human desaturase gene in pRAE-7 (SEQ ID NO:20) and the contig 38 (SEQ ID NO:21).

FIG. 20 illustrates the amino acid sequence identity between the N-terminus of clone A-1 (SEQ ID NO:22), a representative of Group 1, and the N-terminus of the cytochrome b5 gene.

FIG. 21 illustrates the nucleotide sequence identity between the nucleotide sequence of a portion of clone A-1 (SEQ ID NO:24) and a portion of the GenBank sequence ac004228 (SEQ ID NO:25).

FIG. 22 represents the nucleotide sequence identity between the nucleotide sequence of a portion of clone 3-5 (SEQ ID NO:26) of Group 2 and a portion of the GenBank sequence acO04228 (SEQ ID NO:27). Clone 3-5 has an ATG within a NcoI site, but translates four stops between the ATG and the BamHI site.

FIG. 23 represents the nucleotide sequence identity between the nucleotide sequence of a portion of clone A-10 (SEQ ID NO:28) of Group 3 and a portion of the GenBank sequence ac004228 (SEQ ID NO:29). Clone A-10 has an ATG 135 bp upstream of the BamHI site, giving an open reading frame of 1267 bp.

FIG. 24 represents the nucleotide sequence identity between the nucleotide sequence of a portion of clone A-16 (SEQ ID NO:30) of Group 4 and a portion of the GenBank sequence ac004228 (SEQ ID NO:31). Clone A-16 does not have an ATG; however, there is an ATG (underlined) upstream of where the sequence aligns with ac004228.

FIG. 25 represents the nucleotide sequence identity between the nucleotide sequence of a portion of clone A-19 (SEQ ID NO:32) of Group 5 and a portion of the GenBank sequence ac004228 (SEQ ID NO:33). Clone A-19 does not have an ATG; however, this clone matches the ac004228 sequence even upstream of the BamHI site.

FIG. 26 represents the partial nucleotide sequence of the GenBank sequence ac004228 and the representative clones from the five Groups (SEQ ID NO:34).

FIG. 27 represents the nucleotide sequence identity between the human Δ5-desaturase (SEQ ID NO:35) and contig 3381584 (SEQ ID NO:36).

FIG. 28 represents the nucleotide sequence identity between the human Δ5-desaturase (SEQ ID NO:37) and contig 2153526 (SEQ ID NO:38).

FIG. 29 represents the amino acid sequence identity between the human Δ5-desaturase (SEQ ID NO:39) and contig 253538a (SEQ ID NO:40).

FIG. 30 represents the amino acid sequence identity between the human Δ5-desaturase (SEQ ID NO:41) and contig 38 (SEQ ID NO:42).

FIG. 31 represents the amino acid sequence identity between the *M. alpina* Δ6-desaturase (Ma524) (SEQ ID NO:44) and the human the Δ5-desaturase (SEQ ID NO:43).

FIG. 32 represents the amino acid sequence identity between the *M. alpina* Δ5-desaturase (Ma29) (SEQ ID NO:46) and the human Δ5-desaturase (SEQ ID NO:45).

FIG. 33 illustrates the human Δ5-desaturase activity of the gene in clone pRAE-28-5, compared to that in pRAE-26-1, pRAE-33, and pRAE-35, when expressed in baker's yeast.

FIG. 34 illustrates the substrate specificity of the human Δ5-desaturase gene in clone pRAE-28-5, converting DGLA (20:3n-6) to AA (20:4n-6), when the gene is expressed in baker's yeast.

DETAILED DESCRIPTION OF THE INVENTION

Figure 11:
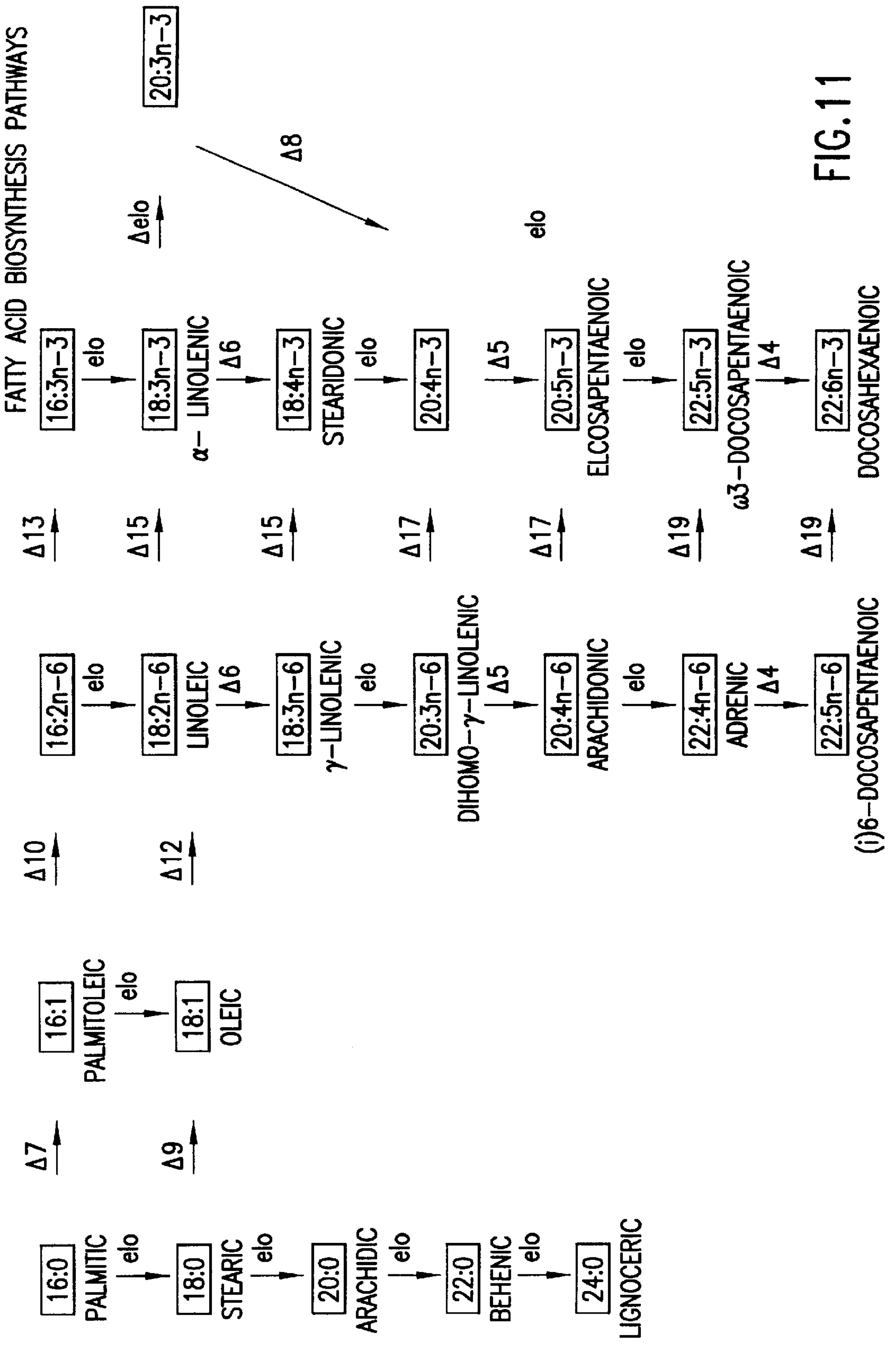
FIG. 11 represents various fatty acid biosynthesis pathways. The role of the Δ5-desaturase enzyme should be noted.

The subject invention relates to the nucleotide and amino acid sequence of the Δ5-desaturase gene derived from humans. Furthermore, the subject invention also includes uses of the gene and of the enzyme encoded by this gene. For example, the gene and corresponding enzyme may be used in the production of polyunsaturated fatty acids such as, for instance, arachidonic acid, eicosapentaenoic acid, and/or adrenic acid which may be added to pharmaceutical compositions, nutritional compositions and to other valuable products.

The Human Δ5-Desaturase Gene and Enzyme Encoded Thereby

As noted above, the enzyme encoded by the human Δ5-desaturase gene is essential in the production of highly unsaturated polyunsaturated fatty acids having a length greater than 20 carbons. The nucleotide sequence of the isolated human Δ5-desaturase gene is shown in FIG. 2, and the amino acid sequence of the corresponding purified protein is shown in FIG. 3.

As an example, the isolated human Δ5-desaturase gene of the present invention converts DGLA to AA or converts 20:4n-3 to EPA. Thus, neither AA nor EPA, for example, can be synthesized without the Δ5-desaturase gene (e.g., human or *M. alpina*) and enzyme encoded thereby.

It should be noted that the present invention also encompasses nucleotide sequences (and the corresponding encoded proteins) having sequences corresponding to or complementary to at least about 50%, preferably at least about 60%, and more preferably at least about 70% of the nucleotides in sequence to SEQ ID NO:1 (i.e., the nucleotide sequence of the human Δ5-desaturase gene described herein (see FIG. 12)). Such sequences may be derived from non-human sources (e.g., *C. elegans* or mouse). Furthermore, the present invention also encompasses fragments and derivatives of the nucleotide sequence of the present invention (i.e., SEQ ID NO:1), as well as of the sequences derived from non-human sources, and having the above-described complementarity or correspondence. Functional equivalents of the above-sequences (i.e., sequences having human Δ5-desaturase activity) are also encompassed by the present invention. The invention also includes a purified polypeptide which desaturates polyunsaturated fatty acids at the carbon 5 position and has at least about 50% amino acid similarity to the amino acid sequence of the above-noted proteins which are, in turn, encoded by the above-described nucleotide sequences.

The present invention also encompasses an isolated nucleotide sequence which encodes PUFA desaturase activity and that is hybridizable, under moderately stringent conditions, to a nucleic acid having a nucleotide sequence corresponding to or complementary to the nucleotide sequence represented by SEQ ID NO:1 and shown in FIG. 12. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

Production of the Human Δ5-Desaturase Enzyme

Once the gene encoding the human Δ5-desaturase enzyme has been isolated, it may then be introduced into either a prokaryotic or eukaryotic host cell through the use of a vector or construct.

The vector, for example, a bacteriophage, cosmid or plasmid, may comprise the nucleotide sequence encoding the human Δ5-desaturase enzyme as well as any promoter which is functional in the host cell and is able to elicit expression of the human Δ5-desaturase encoded by the nucleotide sequence. The promoter is in operable association with or operably linked to the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual,* 2$^{nd}$ ed., Vol. 1–3, ed. Sambrook et al., Cold Spring Harbor Laboratory Press (1989)). The host cell is then cultured under suitable conditions permitting expression of the desired PUFA which is then recovered and purified.

Examples of suitable prokaryotic host cells include, for example, bacteria such as *Escherichia coli, Bacillus subtilis* as well as cyanobacteria such as Spirulina spp. (i.e., blue-green algae). Examples of suitable eukaryotic host cells include, for example, mammalian cells, plant cells, yeast cells such as *Saccharomyces cerevisiae, Saccharomyces carlsbergensis, Lipomyces starkey,* Candida spp. such as *Yarrowia* (Candida) *lipolytica,* Kluyveromyces spp., Pichia spp., Trichoderma Spp. or Hansenula spp., or fungal cells such as filamentous fungal cells, for example, Aspergillus, Neurospora and Penicillium. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme of interest (i.e., the human Δ5-desaturase), and ultimately the PUFA(s) of interest. More specifically, once the above-described construct is created, it may be inserted into the pronucleus of an embryo. The embryo may then be implanted into a recipient female. Alternatively, a nuclear transfer method could also be utilized (Schnieke et al., *Science* 278:2130–2133 (1997)). Gestation and birth are then permitted (see, e.g., U.S. Pat. No. 5,750,176 and U.S. Pat. No. 5;700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the human Δ5-desaturase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of a human Δ5-desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379. Alternatively, the expressed protein can be an enzyme which produces a product which may be incorporated, either directly or upon further modifications, into a fluid fraction from the host plant. Expression of a human Δ5-desaturase gene, or antisense human Δ5-desaturase transcripts, can alter the levels of specific PUFAs, or derivatives thereof, found in plant parts and/or plant tissues. The human Δ5-desaturase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)) or plant tissue may also be utilized as a host or host cell, respectively, for expression of the human Δ5-desaturase enzyme which may, in turn, be utilized in the production of polyunsaturated fatty acids. More specifically, desired PUFAS can be expressed in seed. Methods of isolating seed oils are known in the art. Thus, in addition to providing a source for PUFAs, seed oil components may be manipulated through the expression of the human Δ5-desaturase gene, as well as perhaps other desaturase genes and elongase genes, in order to provide seed oils that can be added to nutritional compositions, pharmaceutical compositions, animal feeds and cosmetics. Once again, a vector which comprises a DNA sequence encoding the human Δ5-desaturase operably linked to a promoter, will be introduced into the plant tissue or plant for a time and under conditions sufficient for expression of the human Δ5-desaturase gene. The vector may also comprise one or more genes that encode other enzymes, for example, Δ4-desaturase, elongase, Δ6-desaturase, Δ12-desaturase, Δ15-desaturase, Δ17-desaturase, and/or Δ19-desaturase. The plant tissue or plant may produce the relevant substrate (e.g., DGLA, GLA, EPA, 20:4n-3, etc.) upon which the enzymes act or a vector encoding enzymes which produce such substrates may be introduced into the plant tissue, plant cell or plant. In addition, substrate may be sprayed on plant tissues expressing the appropriate enzymes. Using these various techniques, one may produce PUFAs (e.g., n-6 unsaturated fatty acids such as AA, or n-3 fatty acids such as EPA or DHA) by use of a plant cell, plant tissue or plant. It should also be noted that the invention also encompasses a transgenic plant comprising the above-described vector, wherein expression of the nucleotide sequence of the vector results in production of a polyunsaturated fatty acid in, for example, the seeds of the transgenic plant.

The substrates which may be produced by the host cell either naturally or transgenically, as well as the enzymes which may be encoded by DNA sequences present in the vector which is subsequently introduced into the host cell, are shown in FIG. 11.

In view of the above, the present invention encompasses a method of producing the human Δ5-desaturase enzyme comprising the steps of: 1) isolating the nucleotide sequence of the gene encoding human Δ5-desaturase enzyme; 2) constructing a vector comprising said nucleotide sequence; and 3) introducing said vector into a host cell under time and conditions sufficient for the production of the desaturase enzyme.

The present invention also encompasses a method of producing polyunsaturated fatty acids comprising exposing an acid to the human Δ5-desaturase enzyme such that the desaturase converts the acid to a polyunsaturated fatty acid. For example, when 20:3n-6 is exposed to human Δ5-desaturase enzyme, it is converted to AA. AA may then be exposed to elongase which elongates the AA to adrenic acid (i.e., 22:4n-6). Alternatively, human Δ5-desaturase may be utilized to convert 20:4n-3 to 20:5n-3 which may be exposed to elongase and converted to (n-3)-docosapentaenoic acid. The (n-3)-docosapentaenoic acid may then be converted to DHA by use of Δ4-desaturase. Thus, human Δ5-desaturase may be used in the production of polyunsaturated fatty acids which may be used, in turn, for particular beneficial purposes.

Uses of the Human Δ5-Desaturase Gene and Enzyme Encoded Thereby

As noted above, the isolated human Δ5-desaturase gene and the desaturase enzyme encoded thereby have many uses. For example, the gene and corresponding enzyme may be used indirectly or directly in the production of polyunsaturated fatty acids, for example, AA, adrenic acid or EPA. ("Directly" is meant to encompass the situation where the enzyme directly converts the acid to another acid, the latter of which is utilized in a composition (e.g., the conversion of DGLA to AA). "Indirectly" is meant to encompass the situation where an acid is converted to another acid (i.e., a pathway intermediate) by the desaturase (e.g., DGLA to AA) and then the latter acid is converted to another acid by use of a non-desaturase enzyme (e.g., AA to adrenic acid by elongase or by use of another desaturase enzyme (e.g., AA to EPA by Δ17-desaturase.)). These polyunsaturated fatty acids (i.e., those produced either directly or indirectly by activity of the desaturase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced directly or indirectly by use of the human Δ5-desaturase gene, in accordance with the present invention, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as AA, EPA and/or docosahexaenoic acid (DHA), produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PUFA composition as GLA (U.S. Pat. No. 5,196,198). Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversion rate of DGLA to AA can be used to produce an AA to DGLA ratio of about 1:19, whereas a conversion rate of about 75% TO 80% can be used to produce an AA to DGLA ratio of about 6:1. Therefore, whether in a cell culture system or in a host animal, regulating the timing, extent and specificity of human Δ5-desaturase expression, as well as the expression of other desaturases and elongases, can be used to modulate PUFA levels and ratios. The PUFAs/acids produced in accordance with the present invention (e.g., AA and EPA) may then be combined with other PUFAs/acids (e.g., GLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the acids and/or resulting oils produced using the human Δ5-desaturase gene, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr.* Vol. 57 (Suppl.)

732S–737S). Altered fatty acid metabolism and composition have been demonstrated in diabetic animals.

Furthermore, the compositions of the present invention, comprising PUFAs produced either directly or indirectly through the use of the human Δ5-desaturase enzyme, may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol.* Vol. 83, p.85–101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal feed supplements, animal feed substitutes, animal vitamins or in animal topical ointments.

The present invention may be illustrated by the use of the following non-limiting examples:

EXAMPLE I

Human Desaturase Gene Sequences

As described in International Application PCT/US98/07422 (herein incorporated in its entirety by reference), the putative human desaturase gene sequences involved in long chain polyunsaturated fatty acid biosynthesis were isolated based on homology between the human cDNA sequences and *Mortierella alpina* desaturase gene sequences. The three conserved "histidine boxes" known to be conserved among membrane-bound desaturases were found. As with other membrane-bound desaturases, the final HXXHH histidine box motif was found to be QXXHH. The amino acid sequence of the putative human desaturases exhibited homology to *M. alpina* Δ5-, Δ6-, Δ9-, and Δ12-desaturases.

The *M. alpina* Δ5-desaturase and Δ6-desaturase cDNA sequences were used to search the LifeSeq database of Incyte Pharmaceuticals, Inc., Palo Alto, Calif. The Δ5-desaturase sequence was divided into fragments: 1) amino acid no. 1–150, 2) amino acid no. 151–300, and 3) amino acid no. 301–446. The Δ6 desaturase sequence was divided into three fragments: 1) amino acid no. 1–150, 2) amino acid no. 151–300, and 3) amino acid no. 301–457. These polypeptide fragments were searched against the database using the "tblastn" algorithm. This algorithm compares a protein query sequence against a nucleotide sequence database dynamically translated in all six reading frames (both strands).

The polypeptide fragments 2 and 3 of *M. alpina* Δ5- and Δ6-desaturases have homologies with the CloneID sequences as outlined in FIG. 1. The CloneID represents an individual sequence from the Incyte LifeSeq database. After the "tblastn" results had been reviewed, Clone Information was searched with the default settings of Stringency of >=50, and Productscore <=100 for different CloneID numbers. The Clone Information Results displayed the information including the ClusterID, CloneID, Library, HitID, and Hit Description. When selected, the ClusterID number displayed the clone information of all the clones that belong in that ClusterID. The Assemble command assembled all of the CloneID which comprise the ClusterID. The following default setting were used for GCG (Genetics Computer Group, University of Wisconsin Biotechnology Center, Madison, Wis.) Assembly:

Word Size: 7; Minimum Overlap: 14; Stringency: 0.8; Minimum Identity: 14; Maximum Gap: 10; Gap Weight: 8; and Length Weight: 2.

GCG Assembly Results displayed the contigs generated on the basis of sequence information within the CloneID. A contig is an alignment of DNA sequences based on areas of homology among these sequences. A new sequence (consensus sequence) was generated based on the aligned DNA sequence within a contig. The contig. containing the CloneID was identified, and the ambiguous sites of the consensus sequence were edited based on the alignment of the CloneIDs (see FIGS. 2–6) to generate the best possible sequence. The procedure was repeated for all six CloneID listed in FIG. 1. This produced five unique contigs. The edited consensus sequences of the 5 contigs were imported into the Sequencher software program (Gene Codes Corporation, Ann Arbor, Mich.). These consensus sequences were assembled. The contig 2511785 overlaps with contig 3506132, and this new contig was called 2535 (FIG. 7). The contigs from the Sequencher program were copied into the Sequence Analysis software package of GCG.

Each contig was translated in all six reading frames into protein sequences. The *M. alpina* Δ5-desaturase (Ma29) and Δ6-desaturase (Ma524) sequences were compared with each of the translated contigs using the FastA search (a Pearson and Lipman search for similarity between a query sequence and a group of sequences of the same type (nucleic acid or protein)). Homology among these sequences suggest the open reading frames of each contig as underlined in FIGS. 3, 5, and 7. The homology among the *M. alpina* Δ5- and Δ6-desaturase sequences to contigs 2535 and 3854933 were utilized to create the final contig called 253538a (see FIG. 8). FIG. 9 is the FastA match of the translated sequences of the final contig 253538a and Ma29, and FIG. 10 is the FastA match of the translated sequences of the final contig 253538a and Ma524.

Although the open reading frame was generated by merging the two contigs, the contig 2535 shows that there is a unique sequence in the beginning of this contig which does not match with the contig 3854933. Therefore, it is possible that these contigs were generated from independent desaturase-like human genes.

The contig 253538a contains an open reading frame encoding 432 amino acid (FIG. 8, underlined). It starts with Gln (CAG) and ends with the stop codon (TGA) (both in bold). The contig 253538a aligns with both *M. alpina* Δ5- and Δ6-desaturase sequences, suggesting that it could be either of the desaturases, as well as other known desaturases which share homology with each other. The individual contigs listed in FIG. 1, as well as the intermediate contig 2535 and the final contig 253538a can be utilized to isolate the complete genes for human desaturases.

Determination of Human Δ5-Desaturase Gene Sequence

Primers RO384 and RO388 were designed based on the 5' and 3' sequences, respectively, of contig 2535. The human monocyte cDNA library (Clontech, Palo Alto, Calif.) was amplified with the vector primer RO329 (5'-CAG ACC AAC TGG TAA TGG TAG-3') SEQ ID NO:49) and RO384 (5'-TCA GGC CCA AGC TGG ATG GCT GCA ACA TG-3'), (SEQ ID NO:50) and also with the vector primer RO328 (5'-CTC CTG GAG CCC GTC AGT ATC-3') (SEQ ID NO:51) and RO388 (5'-ATG GTG GGG AAG AGG TGG TGC TCA ATC TG-3') (SEQ ID NO:52). Polymerase Chain Reaction (PCR) was carried out in a 100 μl volume containing: 1 μl of human monocyte cDNA library, 10 pM each primer, 10 μl of 10×buffer and 1.0 U of Taq Polymerase. Thermocycler conditions in Perkin Elmer 9600 were as follows: 94° C. for 2 mins, then 30 cycles of 94° C. for 1 min., 58° C. for 2 mins. and 72° C. for 3 mins. PCR was followed by an additional extension at 72° C. for 7 minutes.

Figure 14:
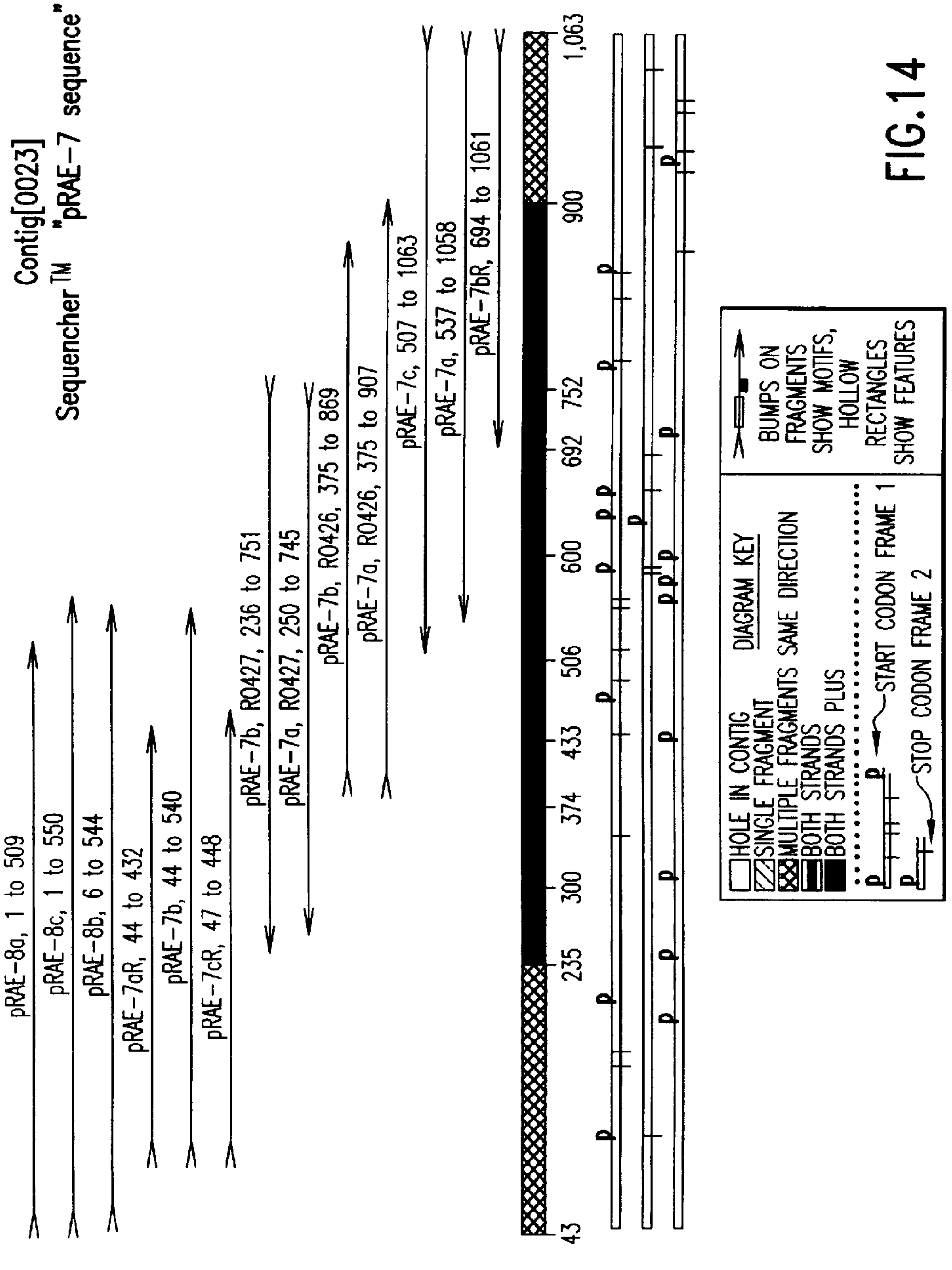
FIG. 14 illustrates the sequence identity between the pRAE-7 and pRAE-8 clones.

The PCR amplified mixture was run on a gel, and the amplified fragments were gel purified. The isolated fragment from PCR amplification with RO329 and RO384 was approximately 900 bp, and that from PCR amplification with RO328 and RO388 was approximately 650 bp. These isolated fragments were filled-in using T4 DNA polymerase, and the filled-in fragments were cloned into the PCR-Blunt vector (Invitrogen Corp., Carlsbad, Calif.). The clone of RO329/RO384 amplified fragment was designated as pRAE-7, and the clone of RO328/RO388 amplified fragment was designated as pRAE-8. Both ends of the clones were sequenced using ABI 373 DNA Sequencer (Applied Biosystems, Foster City, Calif.) and assembled using the Sequencher program (a sequence analysis program, Gene Codes Corporation, Ann Arbor, Mich.). This assembly of the sequences revealed that the two clones contained different sizes of the same gene (FIG. 14). The complete sequence of the pRAE-7 gene was compiled (FIG. 15) and searched against the known sequences in the public database.

The FastA algorithm is a Pearson and Lipman search for similarity between a query sequence and a group of sequences of the same type (nucleic acid or protein). The pRAE-7 gene sequence was translated in six reading frames, and using this method, the Swissprot database (Genetics Computer Group (GCG) (Madison, Wis.) was searched. The gene in pRAE-7 was identified as a putative human desaturase based on its homology to known desaturases. The Swissprot database search produced matches against the omega-3 fatty acid desaturase from mung bean (23.4% identity in 303 AA overlap), linoleoyl-CoA desaturase from Synechocystis sp. (24.3% identity in 280 AA overlap), omega-6 fatty acid desaturase from soybean (19.7% identity in 284 AA overlap), and acyl-CoA desaturase 1 from *Saccharomyces cerevisiae* (21.6% identity in 134 AA overlap). The FastA search against the *M. alpina* desaturases produced matches against the Δ6-(31.9% identity in 285 AA overlap), the Δ5-(28.4% identity in 292 AA overlap), and the Δ12-(23.0% identity in 274 AA overlap) desaturases. The matched sequence alignment of the putative human desaturase gene in pRAE-7 against *M. alpina* Δ5-desaturase (Ma29), *M. alpina* Δ6-desaturase (Ma524) as well as to the contigs 2535 and 38 are displayed in FIGS. 16, 17, 18, and 19 respectively.

The contigs 2535, 38, and 253538a were generated based on assemblies of various sequences as well as their homologies against the known desaturases. However, upon examining FIGS. 18 and 19, it can be concluded that the contigs are merely indications as to what the sequences of the human desaturases might possibly be.

The 5' end of the gene, the ATG (Methionine), is necessary for expressing the human desaturase in yeast. FIGS. 16 and 17 show that pRAE-7 is probably just the last ⅔ of a desaturase gene. Several of the omega-3 and omega-6 fatty acid desaturases, as well as the linoleoyl-CoA desaturase mentioned above, are smaller than the *M. alpina* Δ5- and Δ6-desaturases, ranging in sizes of 359–380 amino acids. It was concluded from all of the sequences evaluated thus far that the isolated gene probably needed anywhere from 180–480 bp (60–160 amino acids) of additional 5' sequence for expressing a complete enzyme.

In order to extend the 5' sequence of the human desaturase gene, the Marathon cDNA Amplification Kit (Clontech, Palo Alto, Calif.) was used to screen the human liver marathon ready cDNA (Clontech). The rapid amplification of cDNA ends (RACE) reactions are efficient for both 5' and 3' long-distance PCR. Following the 5' RACE protocol outlined in the kit, the primers RO430 (5'-GTG GCT GTT GTT ATT GGT GAA GAT AGG CAT C-3') (designed based on the pRAE-7 gene 3' sequence, downstream of the TAA (stop)) and the marathon adaptor primer (AP1) from the kit, were used to generate three PCR amplified products, which were designated A, B, and C. The fragment sizes were approximately 1.5 Kb, 1.4 Kb, 1.2 Kb, respectively. The fragments were filled-in with T4 DNA polymerase, and cloned into the pCR-blunt vector. A total of twenty-two clones were generated and sequenced. Using the FastA algorithm, the sequences were searched against the GenEMBL database of GCG.

Many of the sequences had a great homology to the human DNA sequence with the GenBank accession number of AC004228. This DNA sequence is described as: Sequencing in Progress, *Homo sapiens* Chromosome 11q12pac pDJ519o3; HTGS phase 1,18 unordered pieces. The 18 contigs were recorded in an arbitrary fashion. Using this sequence information and the information from the assembled sequences of the clones, the clones were categorized into five groups.

All of the clones have the same sequence downstream of the BamHI site (see FIG. 12, underlined). But each group represents a different 5' sequence, with a total of 10 clones being too short to be the full length gene. Group 1, represented by clone A-1, is comprised of 5 clones which have homology to cytochrome b5 gene (FIG. 20). A translational start codon, ATG, is not present in clone A-1; however, as can be seen in FIG. 21, there is an ATG (underlined) present in the ac004228 sequence 17 bp upstream of the strong area of homology between A-1 and ac004228. Starting from the strong area of homology, A-1 has an open reading frame of 1318 bp. However, starting from the ATG, the open reading frame is 1335 bp. Group 2, represented by clone 3-5, is comprised of 3 clones which have an ATG within an NcoI site, but four translational stop codons between the ATG and the BamHI site (FIG. 22, the NcoI, BamHI sites are in bold, and the four termination codons are underlined). Group 3 is comprised of one clone, A-10, which has an ATG 135 bp upstream of the BamHI site, giving an open reading frame of 1267 bp (FIG. 23). Group 4 is comprised of 2 clones, represented by clone A-16, which does not have an ATG; however, upstream of where the sequence aligns with ac004228, there is an ATG (FIG. 24, underlined). The open reading frame of this group is 1347 bp. Group 5 is comprised of one clone which does not have an ATG. However, this clone matches the ac004228 sequence even upstream of the BamHI site (FIG. 25).

As illustrated in FIG. 26, many of the clones from the five groups are represented in order with the ac004228 sequence.

There appeared to be a high level of splicing, with the sequence downstream of the BamHI site (in bold) acting as the common anchor for the various 5' exons. All of the potential start sites are also in bold, and the sequences found within the clones have been underlined.

The A-1 sequence was used to search the LifeSeq database of Incyte Pharmaceuticals, Inc., Palo Alto, Calif., to see if its latest version would also have sequences with homology to our desaturase gene sequence. Two contigs were generated in this search, contig 3381584 and contig 2153526. The human desaturase gene sequence was initially compiled based on sequences from Group I clones and ac004228. However, FIG. 12 represents the actual DNA sequence of the isolated gene. The Incyte contigs were used to confirm this sequence (see FIGS. 27 and 28). The human desaturase translated sequence, consisting of 445 amino acids (FIG. 13), was also matched with the original contigs 253538a and 38. These alignments are shown in FIGS. 29 and 30, respectively.

The FastA search of the human desaturase gene against the Swissprot database produced matches against the omega-3 fatty acid desaturase from mung bean (22.4% identity in 381 AA overlap), linoleoyl-CoA desaturase from Synechocystis Sp. (24.5% identity in 335 AA overlap), omega-6 fatty acid desaturase from soybean (20.3% identity in 290 AA overlap), and acyl-CoA desaturase 1 from *Saccharomyces cerevisiae* (21.4% identity in 168 AA overlap). The FastA search against *M. alpina* desaturases produced matches against the Δ6-(30.5% identity in 455 AA overlap), Δ5-(27.5% identity in 455 AA overlap), and Δ12-desaturases (22.5% identity in 382 AA overlap). The FastA match of the human desaturase translated sequence against the ma524 (*M. alpina* Δ6-desaturase) and ma29 (*M. alpina* Δ5-desaturase) sequences are shown in FIGS. 31 and 32, respectively.

EXAMPLE II

Construction of Clones

New clones were generated based on clones from three of the Groups mentioned above, clones A-1, A-10, and A-16. Two primers which were modified with 5' phosphate, RO526 (5'-CAT GGC CCC CGA CCC GGT GG-3') (SEQ ID NO:54) and RO527 (5'-GCG GCC ACC GGG TCG GGG GC-3') (SEQ ID NO:55), were annealed together to form an adaptor. This adaptor which has NcoI and BsaI overhangs, were ligated with the A-1 clone, which had been cut with BsaI/HindIII and gel purified, for 15 min at room temperature. The pYX242(NcoI/HindIII) vector (Novagen, Madison, Wis.) was added to this ligation mixture and allowed to incubate at room temperature for an additional 45 min. This produced a clone designated as pRAE-28-5. (Plasmid pRAE-28-5 was deposited with the American Type Culture Collection, 10801 University Boulevard, Manassas, Va. 20110-2209 on Dec. 22, 1998, under the terms of the Budapest Treaty, and was accorded ATCC number 203557.)

The A-10 clone was PCR amplified with RO512 (5'-GAT TGG GTG CCA TGG GGA TGC GGG ATG AAA AGG C-3') (SEQ ID NO:56) and RO5 (5'-GAA ACA GCT ATG ACC ATG-3') (SEQ ID NO:57), the amplified product was cut with NcoI and HindIII and gel purified, and the purified fragment was cloned into pYX242 (NcoI/HindIII). This new clone was designated as pRAE-26-1.

The A-10 clone was also PCR amplified with RO580 (5'-TCC TS TGC GAA TTC ACC ATG AAA AGG CGG GAG AGA G-3') (SEQ ID NO:58) and RO5, the amplified product was cut with NcoI and HindIII and gel purified, and the purified fragment was cloned into pYX242 (NcoI/HindIII). This new clone was designated as pRAE-33.

Two primers which were modified with 5' phosphate, RO578 (5'-CAT GGC TAG GAG AGG CAG CGC AGC CGC GTC TGG AC-3') (SEQ ID NO:59) and RO579 (5'-CTA GGT CCA GAC GCG GCT GCG CTG CCT CTC CTA GC-3') (SEQ ID NO:60), were annealed together to form an adaptor. This adaptor which has NcoI and BlnI overhangs, were ligated with the A-16 clone, which had been cut with BlnI/HindIII and gel purified, for 15 min at room temperature. The pYX242 (NcoI/HindIII) vector was added to this ligation mixture and allowed to incubate at room temperature for an additional 45 min. This produced a clone designated as pRAE-35.

EXAMPLE III

Expression of Human Δ5-Desaturase

The constructs pRAE-26-1, pRAE-28-5, pRAE-33, and pRAE-35 were transformed into *S. cerevisiae* 334 and screened for desaturase activity. The substrates DGLA (20:3n-6), OA (18:1n-9), AA (20:4n-6), and LA (18:2n-6) were used to determine the activity of the expressed gene from constructs pRAE-26-1 and pRAE-28-5. Only the substrate DGLA was used to determine the activity of the expressed gene from all of the constructs. The negative control strain was *S. cerevisiae* 334 containing the unaltered pYX242 vector. The cultures were grown for 48 hours at 30° C., in selective media (Ausubel et al., *Short Protocols in Molecular Biology,* Ch. 13, P. 3–5 (1992)), in the presence of a particular substrate. Lipid fractions of each culture were extracted for analysis. The desaturase activity results are provided in FIGS. 33 and 34.

All of the values in FIG. 33 are the average of two separate samples per strain, tested in the same run. The substrate, as well as the fatty acid it was converted to, is shown in bold. The expressed gene in the strain 334 (pRAE-28-5) is a Δ5-desaturase. It converted the substrate DGLA to a higher percent of AA than the control strain 334 (pYX242), 0.127% vs. 0.062%, respectively. The percent of AA present in the cultures of strains 334 (pRAE-26-1), 334 (pRAE-33), and 334 (pRAE-35) are comparable to that of the control strain (0.075%, 0.062%, and 0.063%, respectively). Therefore, it can be concluded that the cyt b5 sequence containing gene in the construct pRAE-28-5 expresses an active human Δ5-desaturase; whereas, the other variations of the gene do not.

The activity of the human Δ5-desaturase was further confirmed in the experiment outlined in FIG. 34. Included in this figure are the fatty acid profiles of the strains 334 (pRAE-28-5), 334 (pRAE-26-1), and the control strain 334 (pYX242) when DGLA (20:3n-6), OA (18:1n-9), AA (20:4n-6), or LA (18:2n-6) was used as the substrate, as well as when no substrate was added. Again, the strain 334 (pRAE-28-5) expressed an active human Δ5-desaturase, converting DGLA to AA at a higher percent than the control strain, 0.106% vs. 0.065%, respectively. The strain 334 (pRAE-26-1) had about the same amount of AA (0.06%) as the control. The conversion of the substrate OA to LA was not detected, confirming that the strains do not have a Δ12-desaturase activity. The conversion of the substrate AA to eicosapentaenoic acid (EPA, 20:5n-3) was detected, but at a very low level equal to that of the control strain, confirming that the strains do not have a Δ17-desaturase activity. The conversion of the substrate LA to GLA was detected, but again at a very low level equal to the control strain, confirming that the strains do not have a Δ6-desaturase activity.

The present sequence (FIG. 12) differs from the Genbank sequence g3169158 of the LifeSeq database with respect to two positions. In particular, with respect to the nucleotide sequence of sequence g3169158, position 1082 is an adenosine; however, in the present sequence position 1082 is a thymine (see FIG. 12). Furthermore, position 1229 of sequence g3169158 is an adenine whereas in the present sequence position 1229 is a guanine. In terms of an amino acid sequence comparison, position 361 of the present sequence is a leucine (see FIG. 13), and position 361 of sequence g3169158 is a glutamine. Furthermore, position 410 of the present sequence is an arginine, whereas position 410 of sequence g3169158 is a histidine. Additionally, sequence g3169158 is described, in the database, as a "hypothetical protein" which "exhibits similarity to motifs found in delta 6 desaturase, a hypothetical cytochrome b5 containing fusion protein." However, as demonstrated in the above example, the protein encoded by the sequence in FIG. 12 is a human Δ5-desaturase, not a Δ6-desaturase.

EXAMPLE IV

Expression of Human Δ5-Desaturase in Insect Cells

Insect cells were used as another eukaryotic host for expression of the human Δ5-desaturase. The baculovirus expression system involves the use of insect cells to express a gene, in this case, the human Δ5-desaturase, which has been cloned into a baculovirus expression vector. Insect cells are known to have no endogenous PUFA desaturase activities. Therefore, this system is suitable for expression and characterization of the recombinant desaturases.

The fragment containing the human Δ5-desaturase gene (pRAE-28-5, see EXAMPLE II) was PCR amplified using Expand High Fidelity PCR System (Boehringer Mannheim Corp., Indianapolis, Ind.) and a set of primers containing appropriate restriction sites. The upstream primer designated RO676 (5'-ATA CGT GAA TTC GCC GCC ACC ATG GCC CCC GAC CCG GTG-3') (SEQ ID NO:49) corresponded to the sense strand of Δ5 cDNA and contained an EcoRI site 5' upstream of the ATG. The downstream primer RO677 (5'-TAT CCG CTC GAG TTA TTG GTG AAG ATA GGC ATC TAG-3') (SEQ ID NO:48) corresponded to the antisense strand at the 3' end of the Δ5 cDNA, and included an XhoI site immediately downstream of the translational termination codon. The PRC reaction, in a final volume of 100 μl, was carried out as follows: 5 mins denaturation at 94° C., then 45 seconds at 94° C., 45 seconds at 55° C. and 2 min at 72° C. for 30 cycles, and 7 mins. extension at 72° C. at the end of the amplification. The human Δ5 PCR amplified product was analyzed by agarose-gel electrophoresis, gel purified, digested with EcoRI and XhoI, and then ligated into pFastBac1 baculovirus donor plasmid (Gibco-BRL, Gaithersburg, Md.) which was restricted with the same enzymes. The respective baculovirus clone was designated as pJPBh4 for the human Δ5-desaturase. This pFastBac1 vector contains an expression cassette which has a polyhedrin promoter, a SV40 polyadenylation signal, and a gentamycin resistance marker.

The initial transformation was done in XL1 blue cells (Invitrogen, Carlsbad, Calif.). Positive clones were then transformed into *E. coli* DH10Bac (Gibco-BRL, Gaithersburg, Md.) which contains the baculovirus genome. The positive clones were selected by blue white screening in which white colonies contain the recombinant bacmid. White colonies were then selected for bacmid DNA isolation. DNA was isolated using a Qiagen plasmid isolation kit (Qiagen, Inc., Valencia, Calif.), specific for DNA over 135 kb long. The recombinant bacmid DNA was analyzed on a 0.6% agarose gel to confirm the presence of the high molecular weight DNA. PCR analysis, using pUC/M13 primers (forward 5'-TGT AAA ACG ACG GCC AGT-3' and reverse 5'-GAA ACA GCT ATG ACC ATG-3') was also performed to confirm the correct insert size for the desaturase cDNA within the bacmid.

The Sf9 insect cells (*Spodoptera frugiperda*) were used for the recombinant bacmid DNA transfection. These cells were grown in serum free media (Gibco-BRL, Gaithersburg, Md.). Transfection was carried out according to the CellFECTIN Sf900 protocol (Gibco-BRL, Gaithersburg, Md.). The recombinant virus was recovered by collecting the supernatant at 72 hours post-transfection. A plaque assay was performed on the supernatant to determine the titer of recovered recombinant virion particles. A recombinant viral stock was made for the expression studies. All infections with the recombinant virus were done during the mid-logarithmic growth phase of the Sf9's and infected at 5 MOI (Multiplicity of Infection). To analyze the activity of the expressed human Δ5-desaturase gene, the Sf9m cells were plated at a concentration of $1\times10^6$ cells/well in a 6-well tissue culture plate and infected with 100 μl of the virus stock (approximately 5 MOI). The substrate, dihomo-gamma-linolenic acid (DGLA, C20:3n-6). was supplemented at the time of infection, at a concentration of 100 μM. A mock infected Sf9, as well as cells infected with a recombinant virus containing the GusA reporter gene, were used as negative controls in each experiment. The medium was collected 48 hours post infection and saved. The cells were collected and submitted for lipid analysis.

For fatty acid analysis, cell pellets were vortexed with 6 ml of methanol, followed by the addition of 12 ml of chloroform and tridecanoin (as internal standard). The mixtures were incubated for at least one hour at room temperature or at 4° C. overnight. The chloroform layer was extracted and filtered through a Whatman filter with one gram of anhydrous sodium sulfate to remove particulates and residual water. The organic solvents were evaporated at 40° C. under a stream of nitrogen. The extracted lipids were derivatized to fatty acid methyl esters (FAME) for gas chromatography analysis (GC) by adding 2 ml of 0.5 N potassium hydroxide in methanol to a closed tube. The samples were heated at 95 to 100° C. for 30 minutes and cooled to room temperature. Approximately 2 ml of the 14% boron trifluoride in methanol was added and the heating repeated. After the extracted lipid mixture cooled, 2 ml of water and 1 ml of hexane were added to extract the FAME for GC analysis. The percent conversion was calculated by dividing the product produced by the sum of (the product produced and the substrate) and then multiplying by 100.

The fatty acid synthesis in insect cells infected with recombinant virus containing the human Δ5 cDNA is summarized in Table 1. The conversion of the added substrate, DGLA (C20:3n-6), to arachidonic acid (AA, 20:4n-6) was monitored. The quantity of arachidonic acid (AA, 20:4n-6) produced by the human Δ5-desaturase was 9.67% of the total fatty acid versus the control which did not produce any AA. This resulted in a 29.6% conversion of DGLA to AA.

These data indicate that the human Δ5-desaturase can be expressed in another eukaryotic host (insect cells) in a biologically active form as demonstrated by the production of AA.

TABLE 1

| Fatty Acid | Human Δ5 | Control |
|---|---|---|
| 18:1n-9 | 19.15 | 19.99 |
| 18:3n-6 | 2.43 | 5.18 |
| *20:3n-6 | 22.95 | 30.00 |
| 20:4n-6 (29.6%) | 9.67 | ND |
| 22:1n-9 | 0.11 | 0.25 |

*indicates substrate added
ND indicates None Detected

Nutritional Compositions

The PUFAs described in the Detailed Description may be utilized in various nutritional supplements, infant formulations, nutritional substitutes and other nutritional solutions.

I. Infant Formulations

A. Isomil® Soy Formula with Iron

Usage: As a beverage for infants, children and adults with an allergy or sensitivity to cows milk. A feeding for patients with disorders for which lactose should be avoided: lactase deficiency, lactose intolerance and galactosemia.

Features

Soy protein isolate to avoid symptoms of cowls-milk-protein allergy or sensitivity.

Lactose-free formulation to avoid lactose-associated diarrhea.

Low osmolality (240 mOs/kg water) to reduce risk of osmotic diarrhea.

Dual carbohydrates (corn syrup and sucrose) designed to enhance carbohydrate absorption and reduce the risk of exceeding the absorptive capacity of the damaged gut.

1.8 mg of Iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. Isomil® DF Soy Formula for Diarrhea

Usage: As a short-term feeding for the dietary management of diarrhea in infants and toddlers.

Features

First infant formula to contain added dietary fiber from soy fiber specifically for diarrhea management.

Clinically shown to reduce the duration of loose, watery stools during mild to severe diarrhea in infants.

Nutritionally complete to meet the nutritional needs of the infant.

Soy protein isolate with added L-methionine meets or exceeds an infant's requirement for all essential amino acids.

Lactose-free formulation to avoid lactose-associated diarrhea.

Low osmolality (240 mOsm/kg water) to reduce the risk of osmotic diarrhea.

Dual carbohydrates (corn syrup and sucrose) designed to enhance carbohydrate absorption and reduce the risk of exceeding the absorptive capacity of the damaged gut.

Meets or exceeds the vitamin and mineral levels recommended by the Committee on Nutrition of the American Academy of Pediatrics and required by the Infant Formula Act.

1.8 mg of iron (as ferrous sulfate) per 100 Calories to help prevent iron deficiency.

Vegetable oils to provide recommended levels of essential fatty acids.

Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® SF Sucrose-Free Soy Formula with Iron

Usage: As a beverage for infants, children and adults with an allergy or sensitivity to cow's-milk protein or an intolerance to sucrose. A feeding for patients with disorders for which lactose and sucrose should be avoided.

Features

Soy protein isolate to avoid symptoms of cow's-milk-protein allergy or sensitivity.

Lactose-free formulation to avoid lactose-associated diarrhea (carbohydrate source is Polycose® Glucose Polymers).

Sucrose free for the patient who cannot tolerate sucrose.

Low osmolality (180 mOsm/kg water) to reduce risk of osmotic diarrhea.

1.8 mg of iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. Isomil® 20 Soy Formula with Iron Ready to Feed, 20 Cal/fl oz.

Usage: When a soy feeding is desired.

Ingredients: (Pareve) 85% water, 4.9% corn syrup, 2.6% sugar(sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula

Usage: When an infant formula is needed: if the decision is made to discontinue breastfeeding before age 1 year, if a supplement to breastfeeding is needed or as a routine feeding if breastfeeding is not adopted.

Features

- Protein of appropriate quality and quantity for good growth; heat-denatured, which reduces the risk of milk-associated enteric blood loss.
- Fat from a blend of vegetable oils (doubly homogenized), providing essential linoleic acid that is easily absorbed.
- Carbohydrate as lactose in proportion similar to that of human milk.
- Low renal solute load to minimize stress on developing organs.
- Powder, Concentrated Liquid and Ready To Feed forms.

Ingredients: (-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. Similac® NeoCare Premature Infant Formula with Iron

Usage: For premature infants' special nutritional needs after hospital discharge. Similac NeoCare is a nutritionally complete formula developed to provide premature infants with extra calories, protein, vitamins and minerals needed to promote catch-up growth and support development.

Features

- Reduces the need for caloric and vitamin supplementation. More calories (22 Cal/fl oz) than standard term formulas (20 Cal/fl oz).
- Highly absorbed fat blend, with medium-chain triglycerides (MCT oil) to help meet the special digestive needs of premature infants.
- Higher levels of protein, vitamins and minerals per 100 calories to extend the nutritional support initiated in-hospital.
- More calcium and phosphorus for improved bone mineralization.
- Ingredients: -D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. Similac Natural Care Low-Iron Human Milk Fortifier Ready to Use, 24 Cal/fl oz.

Usage: Designed to be mixed with human milk or to be fed alternatively with human milk to low-birth-weight infants.

Ingredients: -D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae described above and to other infant formulae known to those in the art.

II. Nutritional Formulations

A. ENSURE®

Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.

Patient Conditions

- For patients on modified diets
- For elderly patients at nutrition risk
- For patients with involuntary weight loss
- For patients recovering from illness or surgery
- For patients who need a low-residue diet Ingredients: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. Ensure® Bars

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions

For patients who need extra calories, protein, vitamins and minerals.

Especially useful for people who do not take in enough calories and nutrients.

For people who have the ability to chew and swallow

Not to be used by anyone with a peanut allergy or any type of allergy to nuts.

Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| | |
|---|---|
| Soy protein isolate | 74% |
| Milk proteins | 26% |

Fat: Honey Graham Crunch—The fat source is a blend of partially hydrogenated cottonseed and soybean, canola, high oleic safflower, oils, and soy lecithin.

| | |
|---|---|
| Partially hydrogenated cottonseed and soybean oil | 76% |
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| | |
|---|---|
| High-fructose corn syrup | 24% |
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. Ensure® High Protein

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions

For patients who require additional calories, protein, vitamins, and minerals, such as patients recovering from general surgery or hip fractures, patients at risk for pressure ulcers, and patients on low-cholesterol diets Features Low in saturated fat Contains 6 g of total fat and <5 mg of cholesterol per serving Rich, creamy taste Excellent source of protein, calcium, and other essential vitamins and minerals For low-cholesterol diets Lactose-free, easily digested Ingredients Vanilla Supreme: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Suffate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein

The protein source is a blend of two high-biologic-value proteins: casein and soy.

| | |
|---|---|
| Sodium and calcium caseinates | 85% |
| Soy protein isolate | 15% |

Fat

The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10 of the calories from saturated fatty acids, and <10% of total calories from polyunsaturated fatty acids.

Carbohydrate

ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

Vanilla and Other Nonchocolate Flavors

| | |
|---|---|
| Sucrose | 60% |
| Maltodextrin | 40% |

Chocolate

| | |
|---|---|
| Sucrose | 70% |
| Maltodextrin | 30% |

D. Ensure® Light

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions

For normal-weight or overweight patients who need extra nutrition in a supplement that contains 50% less fat and 20% fewer calories than ENSURE.

For healthy adults who don't eat right and need extra nutrition.

Features

Low in fat and saturated fat

Contains 3 g of total fat per serving and <5 mg cholesterol

Rich, creamy taste

Excellent source of calcium and other essential vitamins and minerals

For low-cholesterol diets

Lactose-free, easily digested

Ingredients

French Vanilla: -D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein

The protein source is calcium caseinate.

| | |
|---|---|
| Calcium caseinate | 100% |

Fat

The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate

ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and Other Nonchocolate Flavors

| | |
|---|---|
| Sucrose | 51% |
| Maltodextrin | 49% |

Chocolate

| | |
|---|---|
| Sucrose | 47.0% |
| Corn Syrup | 26.5% |
| Maltodextrin | 26.5% |

Vitamins and Minerals

An 8-fl-oz serving of ENSURE LIGHT provides at least 25% of the RDIs for 24 key vitamins and minerals.

Caffeine

Chocolate flavor contains 2.1 mg caffeine/8 fl oz.

E. Ensure Plus®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions

For patients who require extra calories and nutrients, but a normal concentration of protein, in a limited volume For patients who need to gain or maintain healthy weight Features Rich, creamy taste Good source of essential vitamins and minerals Ingredients Vanilla: -D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein

The protein source is a blend of two high-biologic-value proteins: casein and soy.

| | |
|---|---|
| Sodium and calcium caseinates | 84% |
| Soy protein isolate | 16% |

Fat

The fat source is corn oil.

| | |
|---|---|
| Corn oil | 100% |

Carbohydrate

ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, Strawberry, Butter Pecan, and Coffee Flavors

| | |
|---|---|
| Corn Syrup | 39% |
| Maltodextrin | 38% |
| Sucrose | 23% |

Chocolate and Eggnog Flavors

| | |
|---|---|
| Corn Syrup | 36% |
| Maltodextrin | 34% |
| Sucrose | 30% |

Vitamins and Minerals

An 8-fl-oz serving of ENSURE PLUS provides at least 15% of the RDIs for 25 key Vitamins and minerals.

Caffeine

Chocolate flavor contains 3.1 mg Caffeine/8 fl oz. Coffee flavor contains a trace amount of caffeine.

F. Ensure Plus® HN

Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions

- For patients with increased calorie and protein needs, such as following surgery or injury.
- For patients with limited volume tolerance and early satiety.

Features

- For supplemental or total nutrition
- For oral or tube feeding
- 1.5 CaVmL,
- High nitrogen
- Calorically dense Ingredients Vanilla: -D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

G. Ensure® Powder

Usage: ENSURE POWDER (reconstituted with water) is a low-residue liquid food designed primarily as an oral nutritional supplement to be used with or between meals. ENSURE POWDER is lactose- and gluten-free, and is suitable for use in modified diets, including low-cholesterol diets.

Patient Conditions

- For patients on modified diets
- For elderly patients at nutrition risk
- For patients recovering from illness/surgery
- For patients who need a low-residue diet Features

- Convenient, easy to mix
- Low in saturated fat
- Contains 9 g of total fat and <5 mg of cholesterol per serving
- High in vitamins and minerals
- For low-cholesterol diets
- Lactose-free, easily digested Ingredients: -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin D3 and Cyanocobalamin.

Protein

The protein source is a blend of two high-biologic-value proteins: casein and soy.

| | |
|---|---|
| Sodium and calcium caseinates | 84% |
| Soy protein isolate | 16% |

Fat

The fat source is corn oil.

| | |
|---|---|
| Corn oil | 100% |

Carbohydrate

ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla

| | |
|---|---|
| Corn Syrup | 35% |
| Maltodextrin | 35% |
| Sucrose | 30% |

H. Ensure® Pudding

Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.

Patient Conditions

For patients on consistency-modified diets (e.g., soft, pureed, or full liquid)

For patients with swallowing impairments

Features

Rich and creamy, good taste

Good source of essential vitamins and minerals

Convenient—needs no refrigeration

Gluten-free

Nutrient Profile per 5 oz: Calories 250, Protein 10.9%, Total Fat 34.9%, Carbohydrate 54.2%.

Ingredients

Vanilla: -D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein

The protein source is nonfat milk.

| | |
|---|---|
| Nonfat milk | 100% |

Fat

The fat source is hydrogenated soybean oil.

| | |
|---|---|
| Hydrogenated soybean oil | 100% |

Carbohydrate

ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and Other Nonchocolate Flavors

| | |
|---|---|
| Sucrose | 56% |
| Lactose | 27% |
| Modified food starch | 17% |

Chocolate

| | |
|---|---|
| Sucrose | 58% |
| Lactose | 26% |
| Modified food starch | 16% |

I. Ensure® with Fiber

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions

For patients who can benefit from increased dietary fiber and nutrients

Features

New advanced formula-low in saturated fat, higher in vitamins and minerals

Contains 6 g of total fat and <5 mg of cholesterol per serving

Rich, creamy taste

Good source of fiber

Excellent source of essential vitamins and minerals

For low-cholesterol diets

Lactose- and gluten-free

Ingredients

Vanilla: -D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein

The protein source is a blend of two high-biologic-value proteins-casein and soy.

| | |
|---|---|
| Sodium and calcium caseinates | 80% |
| Soy protein isolate | 20% |

Fat

The fat source is a blend of three oils: high-oleic safflower, canola, and corn.

| | |
|---|---|
| High-oleic safflower oil | 40% |
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of ≦30% of total calories from fat, <10% of the calories from saturated fatty acids, and ≦10% of total calories from polyunsaturated fatty acids.

Carbohydrate

ENSURE WITH FIBER contains a combination of maltodextrin and sucrose. The mild sweetness and flavor variety (vanilla, chocolate, and butter pecan), plus VARI-FLAVORS® Flavor Pacs in pecan, cherry, strawberry, lemon, and orange, help to prevent flavor fatigue and aid in patient compliance.

Vanilla and Other Nonchocolate Flavors

| | |
|---|---|
| Maltodextrin | 66% |
| Sucrose | 25% |
| Oat Fiber | 7% |
| Soy Fiber | 2% |

Chocolate

| | |
|---|---|
| Maltodextrin | 55% |
| Sucrose | 36% |
| Oat Fiber | 7% |
| Soy Fiber | 2% |

Fiber

The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product

Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution

Caloric density is high at 1.5 Cal/mL (355 Cal/8 fl oz), to minimize the volume required to meet energy needs. The distribution of Calories in Oxepa is shown in Table IV.

TABLE IV

Caloric Distribution of Oxepa

| | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat

- Oxepa contains 22.2 g of fat per 8-fl oz serving (93.7 g/L).
- The fat source is an oil blend of 31.8% canola oil, 25% medium-chain triglycerides (MCTs), 20% borage oil, 20% fish oil, and 3.2% soy lecithin. The typical fatty acid profile of Oxepa is shown in Table V.
- Oxepa provides a balanced amount of polyunsaturated, monounsaturated, and saturated fatty acids, as shown in Table VI.
- Medium-chain trigylcerides (MCTS)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE V

Typical Fatty Acid Profile

| | % Total Fatty Acids | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ-Linolenic | 4.82 | 1.02 | 4.29 |
| Eicosapentaenoic | 5.11 | 1.08 | 4.55 |
| n-3-Docosapent-aenoic | 0.55 | 0.12 | 0.49 |
| Docosahexaenoic | 2.27 | 0.48 | 2.02 |
| Others | 7.55 | 1.52 | 6.72 |

Fatty acids equal approximately 95% of total fat.

TABLE VI

Fat Profile of Oxepa.

| | |
|---|---|
| % of total calories from fat | 55.2 |
| Polyunsaturated fatty acids | 31.44 g/L |
| Monounsaturated fatty acids | 25.53 g/L |
| Saturated fatty acids | 32.38 g/L |
| n-6 to n-3 ratio | 1.75:1 |
| Cholesterol | 9.49 mg/8 fl oz<br>40.1 mg/L |

Carbohydrate

- The carbohydrate content is 25.0 g per 8-fl-oz serving (105.5 g/L).
- The carbohydrate sources are 45% maltodextrin (a complex carbohydrate) and 55% sucrose (a simple sugar), both of which are readily digested and absorbed.
- The high-fat and low-carbohydrate content of Oxepa is designed to minimize carbon dioxide (CO2) production. High CO2 levels can complicate weaning in ventilator-dependent patients. The low level of carbohydrate also may be useful for those patients who have developed stress-induced hyperglycemia.
- Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein

- Oxepa contains 14.8 g of protein per 8-fl-oz serving (62.5 g/L).
- The total calorie/nitrogen ratio (150:1) meets the need of stressed patients.
- Oxepa provides enough protein to promote anabolism and the maintenance of lean body mass without precipitating respiratory problems. High protein intakes are a concern in patients with respiratory insufficiency. Although protein has little effect on CO2 production, a high protein diet will increase ventilatory drive.
- The protein sources of Oxepa are 86.8% sodium caseinate and 13.2% calcium caseinate.
- The amino acid profile of the protein system in Oxepa meets or surpasses the standard for high quality protein set by the National Academy of Sciences.
- Oxepa is gluten-free.

What is claimed is:

1. A method for producing a polyunsaturated fatty acid comprising the steps of:

a) isolating said nucleotide sequence represented by SEQ ID NO:1 (FIG. 12);

b) constructing a vector comprising said isolated nucleotide sequence;

c) introducing said vector into a host cell under time and conditions sufficient for expression of said human Δ5-desaturase enzyme; and d) exposing said expressed human Δ5-desaturase enzyme to a substrate polyunsaturated fatty acid in order to convert said substrate to a product polyunsaturated fatty acid.

2. The method according to claim 1, wherein said substrate polyunsaturated fatty acid is dihomo-γ-linolenic acid (DGLA) or 20:4n-3 and said product polyunsaturated fatty acid is arachidonic acid (AA) or eicosapentaenoic acid (EPA), respectively.

3. The method according to claim 1 further comprising the step of exposing said product polyunsaturated fatty acid to an elongase in order to convert said product polyunsaturated fatty acid to another polyunsaturated fatty acid.

4. The method according to claim 3 wherein said product polyunsaturated fatty acid is AA or EPA and said another polyunsaturated fatty acid is adrenic acid or (n-3)-docosapentaenoic acid, respectively.

5. The method of claim 3 further comprising the steps of exposing said another polyunsaturated fatty acid to an additional desaturase in order to convert said another polyunsaturated fatty acid to a final polyunsaturated fatty acid.

6. The method of claim 5 wherein said final polyunsaturated fatty acid is (n-6)-docosapentaenoic acid or docosahexaenoic (DHA) acid.

* * * * *

SEQUENCE LISTING

<160> NUMBER OF SEQ ID NOS: 60

<210> SEQ ID NO 1
<211> LENGTH: 1335
<212> TYPE: DNA
<213> ORGANISM: Homo sapiens

<400> SEQUENCE: 1
atggcccccg acccggtggc cgccgagacc gcggctcagg gacctacccc gcgctacttc 60
acctgggacg aggtggccca gcgctcaggg tgcgaggagc ggtggctagt gatcgaccgt 120
aaggtgtaca acatcagcga gttcacccgc cggcatccag ggggctcccg ggtcatcagc 180
cactacgccg ggcaggatgc cacggatccc tttgtggcct tccacatcaa caagggcctt 240
gtgaagaagt atatgaactc tctcctgatt ggagaactgt ctccagagca gcccagcttt 300
gagcccacca agaataaaga gctgacagat gagttccggg agctgcgggc cacagtggag 360
cggatggggc tcatgaaggc caaccatgtc ttcttcctgc tgtacctgct gcacatcttg 420
ctgctggatg gtgcagcctg gctcaccctt tgggtctttg ggacgtcctt tttgcccttc 480
ctcctctgtg cggtgctgct cagtgcagtt caggcccagg ctggctggct gcagcatgac 540
tttgggcacc tgtcggtctt cagcacctca aagtggaacc atctgctaca tcattttgtg 600
attggccacc tgaagggggc ccccgccagt tggtggaacc acatgcactt ccagcaccat 660
gccaagccca actgcttccg caaagaccca gacatcaaca tgcatccctt cttctttgcc 720
ttggggaaga tcctctctgt ggagcttggg aaacagaaga aaaaatatat gccgtacaac 780
caccagcaca aatacttctt cctaattggg cccccagcct tgctgcctct ctacttccag 840
tggtatattt tctattttgt tatccagcga aagaagtggg tggacttggc ctggatgatt 900
accttctacg tccgcttctt cctcacttat gtgccactat tggggctgaa agccttcctg 960 ggcctttttct tcatagtcag gttcctggaa agcaactggt ttgtgtgggt gacacagatg 1020
aaccatattc ccatgcacat tgatcatgac cggaacatgg actgggtttc cacccagctc 1080
ctggccacat gcaatgtcca caagtctgcc ttcaatgact ggttcagtgg acacctcaac 1140
ttccagattg agcaccatct ttttcccacg atgcctcgac acaattacca caaagtggct 1200

-continued cccctggtgc agtccttgtg tgccaagcgt ggcatagagt accagtccaa gcccctgctg 1260
tcagccttcg ccgacatcat ccactcacta aaggagtcag ggcagctctg gctagatgcc 1320
tatcttcacc aataa 1335

<210> SEQ ID NO 2
<211> LENGTH: 1219
<212> TYPE: DNA
<213> ORGANISM: Homo sapiens

<400> SEQUENCE: 2
gcacgccgac cggcgccggg agatcctggc aaagtatcca gagataaagt ccttgatgaa 60
acctgatccc aatttgatat ggattataat tatgatggtt ctcacccagt tgggtgcatt 120
ttacatagta aaagacttgg actggaaatg ggtcatattt ggggcctatg cgtttggcag 180
ttgcattaac cactcaatga ctctggctat tcatgagatt gcccacaatg ctgcctttgg 240
caactgcaaa gcaatgtgga atcgctggtt tggaatgttt gctaatcttc ctattgggat 300
tccatattca atttccttta agaggtatca catggatcat catcggtacc ttggagctga 360
tggcgtcgat gtagatattc ctaccgattt tgagggctgg ttcttctgta ccgctttcag 420
aaagtttata tgggttattc ttcagcctct cttttatgcc tttcgacctc tgttcatcaa 480
ccccaaacca attacgtatc tggaagttat caataccgtg gcacaggtca cttttgacat 540
tttaatttat tactttttgg gaattaaatc cttagtctac atgttggcag catctttact 600
tggcctgggt ttgcacccaa tttctggaca ttttatagct gagcattaca tgttcttaaa 660
gggtcatgaa acttactcat attatgggcc tctgaattta cttaccttca atgtgggtta 720
tcataatgaa catcatgatt tccccaacat tcctggaaaa agtcttccac tggtgaggaa 780
aatagcagct gaatactatg acaacctccc tcactacaat tcctggataa aagtactgta 840
tgattttgtg atggatgata caataagtcc ctactcaaga atgaagaggc accaaaaagg 900
agagatggtg ctggagtaaa tatcattagt gccaaaggga ttcttctcca aaactttaga 960
tgataaaatg gaatttttgc attattaaac ttgagaccag tgatgctcag aagctcccct 1020
ggcacaattt cagagtaaga gctcggtgat accaagaagt gaatctggct tttaaacagt 1080
cagcctgact ctgtactgct cagtttcact cacaggaaac ttgtgacttg tgtattatcg 1140
tcattgagga tgtttcactc atgtctgtca ttttataagc atatcattta aaaagcttct 1200
aaaaagctat ttcgccagg 1219

<210> SEQ ID NO 3
<211> LENGTH: 655
<212> TYPE: DNA
<213> ORGANISM: Homo sapiens

<400> SEQUENCE: 3
ttaccttcta cgtccgcttc ttcctcactt atgtgccact attggggctg aaagcttcct 60
gggccttttc ttcatagtca ggttcctgga aagcaactgg tttgtgtggg tgacacagat 120
gaaccatatt cccatgcaca ttgatcatga ccggaacatg gactgggttt ccacccagct 180
ccaggccaca tgcaatgtcc acaagtctgc cttcaatgac tggttcagtg gacacctcaa 240
cttccagatt gagcaccatc tttttcccac gatgcctcga cacaattacc acaaagtggc 300
tcccctggtg cagtccttgt gtgccaagca tggcatagag taccagtcca agcccctgct 360
gtcagccttc gccgacatca tccactcact aaaggagtca gggcagctct ggctagatgc 420

-continued

```
ctatcttcac caataacaac agccaccctg cccagtctgg aagaagagga ggaagactct    480

ggagccaagg cagaggggag cttgagggac aatgccacta tagtttaata ctcagagggg    540

gttgggtttg gggacataaa gcctctgact caaactcctc ccttttatct tctagccaca    600

gttctaagac ccaaagtggg gggtggacac agaagtccct aggagggaag gagct         655


<210> SEQ ID NO 4
<211> LENGTH: 304
<212> TYPE: DNA
<213> ORGANISM: Homo sapiens

<400> SEQUENCE: 4

gtcttttact ttggcaatgg ctggattcct accctcatca cggcctttgt ccttgctacc     60

tctcaggccc aagctggatg gctgcaacat gattatggcc acctgtctgt ctacagaaaa    120

cccaagtgga accaccttgt ccacaaattc gtcattggcc acttaaaggg tgcctctgcc    180

aactggtgga atcatcgcca cttccagcac cacgccaagc ctaacatctt ccacaaggat    240

cccgatgtga acatgctgca cgtgtttgtt ctgggcgaat ggcagcccat cgagtacggc    300

aaga                                                                 304


<210> SEQ ID NO 5
<211> LENGTH: 918
<212> TYPE: DNA
<213> ORGANISM: Homo sapiens
<220> FEATURE:
<221> NAME/KEY: misc_feature
<222> LOCATION: (755)...(755)
<223> OTHER INFORMATION: r = g or a at position 755

<400> SEQUENCE: 5

cagggaccta ccccgcgcta cttcacctgg gacgaggtgg cccagcgctc agggtgcgag     60

gagcggtggc tagtgatcga ccgtaaggtg tacaacatca gcgagttcac ccgccggcat    120

ccagggggct cccgggtcat cagccactac gccgggcagg atgccacgga tccctttgtg    180

gccttccaca tcaacaaggg ccttgtgaag aagtatatga actctctcct gattggagaa    240

ctgtctccag agcagcccag ctttgagccc accaagaata aagagctgac agatgagttc    300

cgggagctgc gggccacagt ggagcggatg gggctcatga aggccaacca tgtcttcttc    360

ctgctgtacc tgctgcacat cttgctgctg gatggtgcag cctggctcac cctttgggtc    420

tttgggacgt cctttttgcc cttcctcctc tgtgcggtgc tgctcagtgc agttcaggcc    480

caggctggct ggctgcagca tgactttggg cacctgtcgg tcttcagcac ctcaaagtgg    540

aaccatctgc tacatcattt tgtgattggc cacctgaagg gggcccccgc cagttggtgg    600

aaccacatgc acttccagca ccatgccaag cccaactgct tccgcaaaga cccagacatc    660

aacatgcatc ccttcttctt tgccttgggg aagatcctct ctgtggagct tgggaaacag    720

aagaaaaaat atatgccgta caaccaccag cacaratact tcttcctaat tgggccccca    780

gccttgctgc ctctctactt ccagtggtat attttctatt ttgttatcca gcgaaagaag    840

tgggtggact tggcctggat cagcaaacag gaatacgatg aagccgggct tccattgtcc    900

accgcaaatg cttctaaa                                                  918


<210> SEQ ID NO 6
<211> LENGTH: 1686
<212> TYPE: DNA
<213> ORGANISM: Homo sapiens

<400> SEQUENCE: 6
```

-continued

```
gccacttaaa gggtgcctct gccaactggt ggaatcatcg ccacttccag caccacgcca     60

agcctaacat cttccacaag gatcccgatg tgaacatgct gcacgtgttt gttctgggcg    120

aatggcagcc catcgagtac ggcaagaaga agctgaaata cctgccctac aatcaccagc    180

acgaatactt cttcctgatt gggccgccgc tgctcatccc catgtatttc cagtaccaga    240

tcatcatgac catgatcgtc cataagaact gggtggacct ggcctgggcc gtcagctact    300

acatccggtt cttcatcacc tacatccctt tctacggcat cctgggagcc ctccttttcc    360

tcaacttcat caggttcctg gagagccact ggtttgtgtg ggtcacacag atgaatcaca    420

tcgtcatgga gattgaccag gaggcctacc gtgactggtt cagtagccag ctgacagcca    480

cctgcaacgt ggagcagtcc ttcttcaacg actggttcag tggacacctt aacttccaga    540

ttgagcacca cctcttcccc accatgcccc ggcacaactt acacaagatc gccccgctgg    600

tgaagtctct atgtgccaag catggcattg aataccagga gaagccgcta ctgagggccc    660

tgctggacat catcaggtcc ctgaagaagt ctgggaagct gtggctggac gcctaccttc    720

acaaatgaag ccacagcccc cgggacaccg tggggaaggg gtgcaggtgg ggtgatggcc    780

agaggaatga tgggcttttg ttctgagggg tgtccgagag gctggtgtat gcactgctca    840

cggaccccat gttggatctt tctccctttc tcctctcctt tttctcttca catctccccc    900

atagcaccct gccctcatgg gacctgccct ccctcagccg tcagccatca gccatggccc    960

tcccagtgcc tcctagcccc ttcttccaag gagcagagag gtggccaccg gggggtggctc  1020

tgtcctacct ccactctctg ccccctaaaga tgggaggaga ccagcggtcc atgggtctgg  1080

cctgtgagtc tccccttgca gcctggtcac taggcatcac ccccgctttg gttcttcaga   1140

tgctcttggg gttcataggg gcaggtccta gtcgggcagg gcccctgacc ctcccggcct   1200

ggcttcactc tccctgacgg ctgccattgg tccacccttt catagagagg cctgctttgt   1260

tacaaagctc gggtctccct cctgcagctc ggttaagtac ccgaggcctc tcttaagatg   1320

tccagggccc caggcccgcg ggcacagcca gcccaaacct tgggccctgg aagagtcctc   1380

caccccatca ctagagtgct ctgaccctgg gctttcacgg gccccattcc accgcctccc   1440

caacttgagc ctgtgacctt gggaccaaag gggggagtccc tcgtctcttg tgactcagca   1500

gaggcagtgg ccacgttcag ggaggggccg gctggcctgg aggctcagcc caccctccag   1560

cttttcctca gggtgtcctg aggtccaaga ttctggagca atctgaccct tctccaaagg   1620

ctctgttatc agctgggcag tgccagccaa tccctggcca tttggcccca ggggacgtgg   1680

gccctg                                                               1686
```

<210> SEQ ID NO 7
<211> LENGTH: 1843
<212> TYPE: DNA
<213> ORGANISM: Homo sapiens

<400> SEQUENCE: 7

```
gtcttttact ttggcaatgg ctggattcct accctcatca cggcctttgt ccttgctacc     60

tctcaggccc aagctggatg gctgcaacat gattatggcc acctgtctgt ctacagaaaa    120

cccaagtgga accaccttgt ccacaaattc gtcattggcc acttaaaggg tgcctctgcc    180

aactggtgga atcatcgcca cttccagcac cacgccaagc ctaacatctt ccacaaggat    240

cccgatgtga acatgctgca cgtgtttgtt ctgggcgaat ggcagcccat cgagtacggc    300

aagaagaagc tgaaatacct gccctacaat caccagcacg aatacttctt cctgattggg    360
```

-continued

```
ccgccgctgc tcatccccat gtatttccag taccagatca tcatgaccat gatcgtccat    420

aagaactggg tggacctggc ctgggccgtc agctactaca tccggttctt catcacctac    480

atccctttct acggcatcct gggagccctc cttttcctca acttcatcag gttcctggag    540

agccactggt ttgtgtgggt cacacagatg aatcacatcg tcatggagat tgaccaggag    600

gcctaccgtg actggttcag tagccagctg acagccacct gcaacgtgga gcagtccttc    660

ttcaacgact ggttcagtgg acaccttaac ttccagattg agcaccacct cttccccacc    720

atgccccggc acaacttaca caagatcgcc ccgctggtga agtctctatg tgccaagcat    780

ggcattgaat accaggagaa gccgctactg agggccctgc tggacatcat caggtccctg    840

aagaagtctg ggaagctgtg gctggacgcc taccttcaca aatgaagcca cagcccccgg    900

gacaccgtgg ggaaggggtg caggtggggt gatggccaga ggaatgatgg gcttttgttc    960

tgaggggtgt ccgagaggct ggtgtatgca ctgctcacgg accccatgtt ggatctttct   1020

ccctttctcc tctccttttt ctcttcacat ctcccccata gcaccctgcc ctcatgggac   1080

ctgccctccc tcagccgtca gccatcagcc atggccctcc cagtgcctcc tagccccttc   1140

ttccaaggag cagagaggtg gccaccgggg gtggctctgt cctacctcca ctctctgccc   1200

ctaaagatgg gaggagacca gcggtccatg ggtctggcct gtgagtctcc ccttgcagcc   1260

tggtcactag gcatcacccc cgctttggtt cttcagatgc tcttggggtt catagggca    1320

ggtcctagtc gggcagggcc cctgaccctc ccggcctggc ttcactctcc ctgacggctg   1380

ccattggtcc accctttcat agagaggcct gctttgttac aaagctcggg tctccctcct   1440

gcagctcggt taagtacccg aggcctctct taagatgtcc agggccccag gcccgcgggc   1500

acagccagcc caaaccttgg gccctggaag agtcctccac cccatcacta gagtgctctg   1560

accctgggct ttcacgggcc ccattccacc gcctccccaa cttgagcctg tgaccttggg   1620

accaaagggg gagtccctcg tctcttgtga ctcagcagag gcagtggcca cgttcaggga   1680

ggggccggct ggcctggagg ctcagcccac cctccagctt ttcctcaggg tgtcctgagg   1740

tccaagattc tggagcaatc tgacccttct ccaaaggctc tgttatcagc tgggcagtgc   1800

cagccaatcc ctggccattt ggccccaggg gacgtgggcc ctg                     1843
```

<210> SEQ ID NO 8
<211> LENGTH: 2257
<212> TYPE: DNA
<213> ORGANISM: Homo sapiens

<400> SEQUENCE: 8

```
cagggaccta ccccgcgcta cttcacctgg gacgaggtgg cccagcgctc agggtgcgag     60

gagcggtggc tagtgatcga ccgtaaggtg tacaacatca gcgagttcac ccgccggcat    120

ccagggggct cccgggtcat cagccactac gccgggcagg atgccacgga tccctttgtg    180

gccttccaca tcaacaaggg ccttgtgaag aagtatatga actctctcct gattggagaa    240

ctgtctccag agcagcccag ctttgagccc accaagaata aagagctgac agatgagttc    300

cgggagctgc gggccacagt ggagcggatg gggctcatga aggccaacca tgtcttcttc    360

ctgctgtacc tgctgcacat cttgctgctg gatggtgcag cctggctcac cctttgggtc    420

tttgggacgt cctttttgcc cttcctcctc tgtgcggtgc tgctcagtgc agttcagcag    480

gcccaagctg gatggctgca acatgattat ggccacctgt ctgtctacag aaaacccaag    540

tggaaccacc ttgtccacaa attcgtcatt ggccacttaa agggtgcctc tgccaactgg    600

tggaatcatc gccacttcca gcaccacgcc aagcctaaca tcttccacaa ggatcccgat    660
```

-continued

```
gtgaacatgc tgcacgtgtt tgttctgggc gaatggcagc ccatcgagta cggcaagaag    720
aagctgaaat acctgcccta caatcaccag cacgaatact tcttcctgat tgggccgccg    780
ctgctcatcc ccatgtattt ccagtaccag atcatcatga ccatgatcgt ccataagaac    840
tgggtggacc tggcctgggc cgtcagctac tacatccggt tcttcatcac ctacatccct    900
ttctacggca tcctgggagc cctccttttc ctcaacttca tcaggttcct ggagagccac    960
tggtttgtgt gggtcacaca gatgaatcac atcgtcatgg agattgacca ggaggcctac   1020
cgtgactggt tcagtagcca gctgacagcc acctgcaacg tggagcagtc cttcttcaac   1080
gactggttca gtggacacct taacttccag attgagcacc acctcttccc caccatgccc   1140
cggcacaact tacacaagat cgccccgctg gtgaagtctc tatgtgccaa gcatggcatt   1200
gaataccagg agaagccgct actgagggcc ctgctggaca tcatcaggtc cctgaagaag   1260
tctgggaagc tgtggctgga cgcctacctt cacaaatgaa gccacagccc ccgggacacc   1320
gtggggaagg ggtgcaggtg gggtgatggc cagaggaatg atgggctttt gttctgaggg   1380
gtgtccgaga ggctggtgta tgcactgctc acggacccca tgttggatct ttctcccttt   1440
ctcctctcct tttctcttc acatctcccc catagcaccc tgccctcatg ggacctgccc   1500
tccctcagcc gtcagccatc agccatggcc ctcccagtgc ctcctagccc cttcttccaa   1560
ggagcagaga ggtggccacc gggggtggct ctgtcctacc tccactctct gcccctaaag   1620
atgggaggag accagcggtc catgggtctg gcctgtgagt ctccccttgc agcctggtca   1680
ctaggcatca cccccgcttt ggttcttcag atgctcttgg ggttcatagg ggcaggtcct   1740
agtcgggcag ggcccctgac cctcccggcc tggcttcact ctccctgacg gctgccattg   1800
gtccaccctt tcatagagag gcctgctttg ttacaaagct cgggtctccc tcctgcagct   1860
cggttaagta cccgaggcct ctcttaagat gtccagggcc ccaggcccgc gggcacagcc   1920
agcccaaacc ttgggccctg gaagagtcct ccaccccatc actagagtgc tctgaccctg   1980
ggctttcacg ggccccattc caccgcctcc ccaacttgag cctgtgacct tgggaccaaa   2040
gggggagtcc ctcgtctctt gtgactcagc agaggcagtg gccacgttca gggaggggcc   2100
ggctggcctg gaggctcagc ccaccctcca gcttttcctc agggtgtcct gaggtccaag   2160
attctggagc aatctgaccc ttctccaaag gctctgttat cagctgggca gtgccagcca   2220
atccctggcc atttggcccc aggggacgtg ggccctg                             2257
```

```
<210> SEQ ID NO 9
<211> LENGTH: 432
<212> TYPE: PRT
<213> ORGANISM: Homo sapiens
<220> FEATURE:
<221> NAME/KEY: VARIANT
<222> LOCATION: (432)...(432)
<223> OTHER INFORMATION: Xaa = Unknown or other at position 432

<400> SEQUENCE: 9

Gln Gly Pro Thr Pro Arg Tyr Phe Thr Trp Asp Glu Val Ala Gln Arg
 1               5                  10                  15

Ser Gly Cys Glu Glu Arg Trp Leu Val Ile Asp Arg Lys Val Tyr Asn
            20                  25                  30

Ile Ser Glu Phe Thr Arg Arg His Pro Gly Gly Ser Arg Val Ile Ser
        35                  40                  45

His Tyr Ala Gly Gln Asp Ala Thr Asp Pro Phe Val Ala Phe His Ile
    50                  55                  60
```

-continued

```
Asn Lys Gly Leu Val Lys Lys Tyr Met Asn Ser Leu Leu Ile Gly Glu
65                  70                  75                  80

Leu Ser Pro Glu Gln Pro Ser Phe Glu Pro Thr Lys Asn Lys Glu Leu
                85                  90                  95

Thr Asp Glu Phe Arg Glu Leu Arg Ala Thr Val Glu Arg Met Gly Leu
            100                 105                 110

Met Lys Ala Asn His Val Phe Phe Leu Leu Tyr Leu Leu His Ile Leu
        115                 120                 125

Leu Leu Asp Gly Ala Ala Trp Leu Thr Leu Trp Val Phe Gly Thr Ser
    130                 135                 140

Phe Leu Pro Phe Leu Leu Cys Ala Val Leu Leu Ser Ala Val Gln Ala
145                 150                 155                 160

Gln Ala Gly Trp Leu Gln His Asp Tyr Gly His Leu Ser Val Tyr Arg
                165                 170                 175

Lys Pro Lys Trp Asn His Leu Val His Lys Phe Val Ile Gly His Leu
            180                 185                 190

Lys Gly Ala Ser Ala Asn Trp Trp Asn His Arg His Phe Gln His His
        195                 200                 205

Ala Lys Pro Asn Ile Phe His Lys Asp Pro Asp Val Asn Met Leu His
    210                 215                 220

Val Phe Val Leu Gly Glu Trp Gln Pro Ile Glu Tyr Gly Lys Lys Lys
225                 230                 235                 240

Leu Lys Tyr Leu Pro Tyr Asn His Gln His Glu Tyr Phe Phe Leu Ile
                245                 250                 255

Gly Pro Pro Leu Leu Ile Pro Met Tyr Phe Gln Tyr Gln Ile Ile Met
            260                 265                 270

Thr Met Ile Val His Lys Asn Trp Val Asp Leu Ala Trp Ala Val Ser
        275                 280                 285

Tyr Tyr Ile Arg Phe Phe Ile Thr Tyr Ile Pro Phe Tyr Gly Ile Leu
    290                 295                 300

Gly Ala Leu Leu Phe Leu Asn Phe Ile Arg Phe Leu Glu Ser His Trp
305                 310                 315                 320

Phe Val Trp Val Thr Gln Met Asn His Ile Val Met Glu Ile Asp Gln
                325                 330                 335

Glu Ala Tyr Arg Asp Trp Phe Ser Ser Gln Leu Thr Ala Thr Cys Asn
            340                 345                 350

Val Glu Gln Ser Phe Phe Asn Asp Trp Phe Ser Gly His Leu Asn Phe
        355                 360                 365

Gln Ile Glu His His Leu Phe Pro Thr Met Pro Arg His Asn Leu His
    370                 375                 380

Lys Ile Ala Pro Leu Val Lys Ser Leu Cys Ala Lys His Gly Ile Glu
385                 390                 395                 400

Tyr Gln Glu Lys Pro Leu Leu Arg Ala Leu Leu Asp Ile Ile Arg Ser
                405                 410                 415

Leu Lys Lys Ser Gly Lys Leu Trp Leu Asp Ala Tyr Leu His Lys Xaa
            420                 425                 430


<210> SEQ ID NO 10
<211> LENGTH: 458
<212> TYPE: PRT
<213> ORGANISM: Homo sapiens
<220> FEATURE:
<221> NAME/KEY: VARIANT
<222> LOCATION: (458)...(458)
<223> OTHER INFORMATION: Xaa = Unknown or other at position 458
```

-continued

<400> SEQUENCE: 10

```
Met Ala Ala Ala Pro Ser Val Arg Thr Phe Thr Arg Ala Glu Val Leu
 1               5                  10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415
```

-continued

```
Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln Xaa
    450                 455


<210> SEQ ID NO 11
<211> LENGTH: 444
<212> TYPE: PRT
<213> ORGANISM: Homo sapiens

<400> SEQUENCE: 11

Met Ala Pro Asp Pro Val Ala Ala Glu Thr Ala Ala Gln Gly Pro Thr
 1               5                  10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140

Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
            180                 185                 190

Asn His Leu Leu His His Phe Val Ile Gly His Leu Lys Gly Ala Pro
        195                 200                 205

Ala Ser Trp Trp Asn His Met His Phe Gln His His Ala Lys Pro Asn
    210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
            260                 265                 270

Ala Leu Leu Pro Leu Tyr Phe Gln Trp Tyr Ile Phe Tyr Phe Val Ile
        275                 280                 285

Gln Arg Lys Lys Trp Val Asp Leu Ala Trp Met Ile Thr Phe Tyr Val
    290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
```

-continued 325 330 335

Val Thr Gln Met Asn His Ile Pro Met His Ile Asp His Asp Arg Asn
340 345 350

Met Asp Trp Val Ser Thr Gln Leu Leu Ala Thr Cys Asn Val His Lys
355 360 365

Ser Ala Phe Asn Asp Trp Phe Ser Gly His Leu Asn Phe Gln Ile Glu
370 375 380

His His Leu Phe Pro Thr Met Pro Arg His Asn Tyr His Lys Val Ala
385 390 395 400

Pro Leu Val Gln Ser Leu Cys Ala Lys Arg Gly Ile Glu Tyr Gln Ser
405 410 415

Lys Pro Leu Leu Ser Ala Phe Ala Asp Ile Ile His Ser Leu Lys Glu
420 425 430

Ser Gly Gln Leu Trp Leu Asp Ala Tyr Leu His Gln
435 440

<210> SEQ ID NO 12
<211> LENGTH: 864
<212> TYPE: DNA
<213> ORGANISM: Homo sapiens

<400> SEQUENCE: 12
ctcctggagc ccgtcagtat cggcggaatt ccggcagttc aggcccaggc tggctggctg 60
cagcatgact ttgggcacct gtcggtcttc agcacctcaa agtggaacca tctgctacat 120
cattttgtga ttggccacct gaagggggcc cccgccagtt ggtggaacca catgcacttc 180
cagcaccatg ccaagcccaa ctgcttccgc aaagacccag acatcaacat gcatcccttc 240
ttctttgcct tggggaagat cctctctgtg gagcttggga aacagaagaa aaaatatatg 300
ccgtacaacc accagcacaa atacttcttc ctaattgggc ccccagcctt gctgcctctc 360
tacttccagt ggtatatttt ctattttgtt atccagcgaa agaagtgggt ggacttggcc 420
tggatgatta ccttctacgt ccgcttcttc ctcacttatg tgccactatt ggggctgaaa 480
gccttcctgg gccttttctt catagtcagg ttcctggaaa gcaactggtt tgtgtgggtg 540
acacagatga accatattcc catgcacatt gatcatgacc ggaacatgga ctgggtttcc 600
acccagctcc aggccacatg caatgtccac aagtctgcct tcaatgactg gttcagtgga 660
cacctcaact tccagattga gcaccatctt tttcccacga tgcctcgaca caattaccac 720
aaagtggctc ccctggtgca gtccttgtgt gccaagcatg gcatagagta ccagtccaag 780
cccctgctgt cagccttcgc cgacatcatc cactcactaa aggagtcagg gcagctctgg 840
ctagatgcct atcttcacca ataa 864

<210> SEQ ID NO 13
<211> LENGTH: 287
<212> TYPE: PRT
<213> ORGANISM: Homo sapiens

<400> SEQUENCE: 13

Leu Leu Glu Pro Val Ser Ile Gly Gly Ile Pro Ala Val Gln Ala Gln
1 5 10 15

Ala Gly Trp Leu Gln His Asp Phe Gly His Leu Ser Val Phe Ser Thr
20 25 30

Ser Lys Trp Asn His Leu Leu His His Phe Val Ile Gly His Leu Lys
35 40 45

Gly Ala Pro Ala Ser Trp Trp Asn His Met His Phe Gln His His Ala

-continued

```
    50                  55                  60

Lys Pro Asn Cys Phe Arg Lys Asp Pro Asp Ile Asn Met His Pro Phe
65                  70                  75                  80

Phe Phe Ala Leu Gly Lys Ile Leu Ser Val Glu Leu Gly Lys Gln Lys
                85                  90                  95

Lys Lys Tyr Met Pro Tyr Asn His Gln His Lys Tyr Phe Phe Leu Ile
            100                 105                 110

Gly Pro Pro Ala Leu Leu Pro Leu Tyr Phe Gln Trp Tyr Ile Phe Tyr
        115                 120                 125

Phe Val Ile Gln Arg Lys Lys Trp Val Asp Leu Ala Trp Met Ile Thr
    130                 135                 140

Phe Tyr Val Arg Phe Phe Leu Thr Tyr Val Pro Leu Leu Gly Leu Lys
145                 150                 155                 160

Ala Phe Leu Gly Leu Phe Phe Ile Val Arg Phe Leu Glu Ser Asn Trp
                165                 170                 175

Phe Val Trp Val Thr Gln Met Asn His Ile Pro Met His Ile Asp His
            180                 185                 190

Asp Arg Asn Met Asp Trp Val Ser Thr Gln Leu Gln Ala Thr Cys Asn
        195                 200                 205

Val His Lys Ser Ala Phe Asn Asp Trp Phe Ser Gly His Leu Asn Phe
    210                 215                 220

Gln Ile Glu His His Leu Phe Pro Thr Met Pro Arg His Asn Tyr His
225                 230                 235                 240

Lys Val Ala Pro Leu Val Gln Ser Leu Cys Ala Lys His Gly Ile Glu
                245                 250                 255

Tyr Gln Ser Lys Pro Leu Leu Ser Ala Phe Ala Asp Ile Ile His Ser
            260                 265                 270

Leu Lys Glu Ser Gly Gln Leu Trp Leu Asp Ala Tyr Leu His Gln
        275                 280                 285


<210> SEQ ID NO 14
<211> LENGTH: 288
<212> TYPE: PRT
<213> ORGANISM: Homo sapiens
<220> FEATURE:
<221> NAME/KEY: VARIANT
<222> LOCATION: (288)...(288)
<223> OTHER INFORMATION: Xaa = Unknown or other at position 288

<400> SEQUENCE: 14

Leu Leu Glu Pro Val Ser Ile Gly Gly Ile Pro Ala Val Gln Ala Gln
 1               5                  10                  15

Ala Gly Trp Leu Gln His Asp Phe Gly His Leu Ser Val Phe Ser Thr
            20                  25                  30

Ser Lys Trp Asn His Leu Leu His His Phe Val Ile Gly His Leu Lys
        35                  40                  45

Gly Ala Pro Ala Ser Trp Trp Asn His Met His Phe Gln His His Ala
    50                  55                  60

Lys Pro Asn Cys Phe Arg Lys Asp Pro Asp Ile Asn Met His Pro Phe
65                  70                  75                  80

Phe Phe Ala Leu Gly Lys Ile Leu Ser Val Glu Leu Gly Lys Gln Lys
                85                  90                  95

Lys Lys Tyr Met Pro Tyr Asn His Gln His Lys Tyr Phe Phe Leu Ile
            100                 105                 110

Gly Pro Pro Ala Leu Leu Pro Leu Tyr Phe Gln Trp Tyr Ile Phe Tyr
        115                 120                 125
```

-continued

```
Phe Val Ile Gln Arg Lys Lys Trp Val Asp Leu Ala Trp Met Ile Thr
    130                 135                 140

Phe Tyr Val Arg Phe Phe Leu Thr Tyr Val Pro Leu Leu Gly Leu Lys
145                 150                 155                 160

Ala Phe Leu Gly Leu Phe Phe Ile Val Arg Phe Leu Glu Ser Asn Trp
                165                 170                 175

Phe Val Trp Val Thr Gln Met Asn His Ile Pro Met His Ile Asp His
            180                 185                 190

Asp Arg Asn Met Asp Trp Val Ser Thr Gln Leu Gln Ala Thr Cys Asn
        195                 200                 205

Val His Lys Ser Ala Phe Asn Asp Trp Phe Ser Gly His Leu Asn Phe
    210                 215                 220

Gln Ile Glu His His Leu Phe Pro Thr Met Pro Arg His Asn Tyr His
225                 230                 235                 240

Lys Val Ala Pro Leu Val Gln Ser Leu Cys Ala Lys His Gly Ile Glu
                245                 250                 255

Tyr Gln Ser Lys Pro Leu Leu Ser Ala Phe Ala Asp Ile Ile His Ser
            260                 265                 270

Leu Lys Glu Ser Gly Gln Leu Trp Leu Asp Ala Tyr Leu His Gln Xaa
        275                 280                 285


<210> SEQ ID NO 15
<211> LENGTH: 315
<212> TYPE: PRT
<213> ORGANISM: Homo sapiens
<220> FEATURE:
<221> NAME/KEY: VARIANT
<222> LOCATION: (315)...(315)
<223> OTHER INFORMATION: Xaa = Unknown or other at position 315

<400> SEQUENCE: 15

Ala Ser Tyr Tyr Ala Gln Leu Phe Val Pro Phe Val Val Glu Arg Thr
 1               5                  10                  15

Trp Leu Gln Val Val Phe Ala Ile Ile Met Gly Phe Ala Cys Ala Gln
            20                  25                  30

Val Gly Leu Asn Pro Leu His Asp Ala Ser His Phe Ser Val Thr His
        35                  40                  45

Asn Pro Thr Val Trp Lys Ile Leu Gly Ala Thr His Asp Phe Phe Asn
    50                  55                  60

Gly Ala Ser Tyr Leu Val Trp Met Tyr Gln His Met Leu Gly His His
65                  70                  75                  80

Pro Tyr Thr Asn Ile Ala Gly Ala Asp Pro Asp Val Ser Thr Ser Glu
                85                  90                  95

Pro Asp Val Arg Arg Ile Lys Pro Asn Gln Lys Trp Phe Val Asn His
            100                 105                 110

Ile Asn Gln His Met Phe Val Pro Phe Leu Tyr Gly Leu Leu Ala Phe
        115                 120                 125

Lys Val Arg Ile Gln Asp Ile Asn Ile Leu Tyr Phe Val Lys Thr Asn
    130                 135                 140

Asp Ala Ile Arg Val Asn Pro Ile Ser Thr Trp His Thr Val Met Phe
145                 150                 155                 160

Trp Gly Gly Lys Ala Phe Phe Val Trp Tyr Arg Leu Ile Val Pro Leu
                165                 170                 175

Gln Tyr Leu Pro Leu Gly Lys Val Leu Leu Leu Phe Thr Val Ala Asp
            180                 185                 190
```

-continued

```
Met Val Ser Ser Tyr Trp Leu Ala Leu Thr Phe Gln Ala Asn His Val
        195                 200                 205

Val Glu Glu Val Gln Trp Pro Leu Pro Asp Glu Asn Gly Ile Ile Gln
    210                 215                 220

Lys Asp Trp Ala Ala Met Gln Val Glu Thr Thr Gln Asp Tyr Ala His
225                 230                 235                 240

Asp Ser His Leu Trp Thr Ser Ile Thr Gly Ser Leu Asn Tyr Gln Ala
                245                 250                 255

Val His His Leu Phe Pro Asn Val Ser Gln His His Tyr Pro Asp Ile
            260                 265                 270

Leu Ala Ile Ile Lys Asn Thr Cys Ser Glu Tyr Lys Val Pro Tyr Leu
        275                 280                 285

Val Lys Asp Thr Phe Trp Gln Ala Phe Ala Ser His Leu Glu His Leu
    290                 295                 300

Arg Val Leu Gly Leu Arg Pro Lys Glu Glu Xaa
305                 310                 315


<210> SEQ ID NO 16
<211> LENGTH: 288
<212> TYPE: PRT
<213> ORGANISM: Homo sapiens
<220> FEATURE:
<221> NAME/KEY: VARIANT
<222> LOCATION: (288)...(288)
<223> OTHER INFORMATION: Xaa = Unknown or other at position 288

<400> SEQUENCE: 16

Leu Leu Glu Pro Val Ser Ile Gly Gly Ile Pro Ala Val Gln Ala Gln
 1               5                  10                  15

Ala Gly Trp Leu Gln His Asp Phe Gly His Leu Ser Val Phe Ser Thr
            20                  25                  30

Ser Lys Trp Asn His Leu Leu His His Phe Val Ile Gly His Leu Lys
        35                  40                  45

Gly Ala Pro Ala Ser Trp Trp Asn His Met His Phe Gln His His Ala
    50                  55                  60

Lys Pro Asn Cys Phe Arg Lys Asp Pro Asp Ile Asn Met His Pro Phe
65                  70                  75                  80

Phe Phe Ala Leu Gly Lys Ile Leu Ser Val Glu Leu Gly Lys Gln Lys
                85                  90                  95

Lys Lys Tyr Met Pro Tyr Asn His Gln His Lys Tyr Phe Phe Leu Ile
            100                 105                 110

Gly Pro Pro Ala Leu Leu Pro Leu Tyr Phe Gln Trp Tyr Ile Phe Tyr
        115                 120                 125

Phe Val Ile Gln Arg Lys Lys Trp Val Asp Leu Ala Trp Met Ile Thr
    130                 135                 140

Phe Tyr Val Arg Phe Phe Leu Thr Tyr Val Pro Leu Leu Gly Leu Lys
145                 150                 155                 160

Ala Phe Leu Gly Leu Phe Phe Ile Val Arg Phe Leu Glu Ser Asn Trp
                165                 170                 175

Phe Val Trp Val Thr Gln Met Asn His Ile Pro Met His Ile Asp His
            180                 185                 190

Asp Arg Asn Met Asp Trp Val Ser Thr Gln Leu Gln Ala Thr Cys Asn
        195                 200                 205

Val His Lys Ser Ala Phe Asn Asp Trp Phe Ser Gly His Leu Asn Phe
    210                 215                 220

Gln Ile Glu His His Leu Phe Pro Thr Met Pro Arg His Asn Tyr His
```

-continued

```
225                 230                 235                 240

Lys Val Ala Pro Leu Val Gln Ser Leu Cys Ala Lys His Gly Ile Glu
                245                 250                 255

Tyr Gln Ser Lys Pro Leu Leu Ser Ala Phe Ala Asp Ile Ile His Ser
            260                 265                 270

Leu Lys Glu Ser Gly Gln Leu Trp Leu Asp Ala Tyr Leu His Gln Xaa
        275                 280                 285


<210> SEQ ID NO 17
<211> LENGTH: 323
<212> TYPE: PRT
<213> ORGANISM: Homo sapiens
<220> FEATURE:
<221> NAME/KEY: VARIANT
<222> LOCATION: (323)...(323)
<223> OTHER INFORMATION: Xaa = Unknown or other at position 323

<400> SEQUENCE: 17

Gly Leu Ser Thr Val Ile Val Ala Lys Trp Gly Gln Thr Ser Thr Leu
 1               5                  10                  15

Ala Asn Val Leu Ser Ala Ala Leu Leu Gly Leu Phe Trp Gln Gln Cys
            20                  25                  30

Gly Trp Leu Ala His Asp Phe Leu His His Gln Val Phe Gln Asp Arg
        35                  40                  45

Phe Trp Gly Asp Leu Phe Gly Ala Phe Leu Gly Gly Val Cys Gln Gly
    50                  55                  60

Phe Ser Ser Ser Trp Trp Lys Asp Lys His Asn Thr His His Ala Ala
65                  70                  75                  80

Pro Asn Val His Gly Glu Asp Pro Asp Ile Asp Thr His Pro Leu Leu
                85                  90                  95

Thr Trp Ser Glu His Ala Leu Glu Met Phe Ser Asp Val Pro Asp Glu
            100                 105                 110

Glu Leu Thr Arg Met Trp Ser Arg Phe Met Val Leu Asn Gln Thr Trp
        115                 120                 125

Phe Tyr Phe Pro Ile Leu Ser Phe Ala Arg Leu Ser Trp Cys Leu Gln
    130                 135                 140

Ser Ile Leu Phe Val Leu Pro Asn Gly Gln Ala His Lys Pro Ser Gly
145                 150                 155                 160

Ala Arg Val Pro Ile Ser Leu Val Glu Gln Leu Ser Leu Ala Met His
                165                 170                 175

Trp Thr Trp Tyr Leu Ala Thr Met Phe Leu Phe Ile Lys Asp Pro Val
            180                 185                 190

Asn Met Leu Val Tyr Phe Leu Val Ser Gln Ala Val Cys Gly Asn Leu
        195                 200                 205

Leu Ala Ile Val Phe Ser Leu Asn His Asn Gly Met Pro Val Ile Ser
    210                 215                 220

Lys Glu Glu Ala Val Asp Met Asp Phe Phe Thr Lys Gln Ile Ile Thr
225                 230                 235                 240

Gly Arg Asp Val His Pro Gly Leu Phe Ala Asn Trp Phe Thr Gly Gly
                245                 250                 255

Leu Asn Tyr Gln Ile Glu His His Leu Phe Pro Ser Met Pro Arg His
            260                 265                 270

Asn Phe Ser Lys Ile Gln Pro Ala Val Glu Thr Leu Cys Lys Lys Tyr
        275                 280                 285

Asn Val Arg Tyr His Thr Thr Gly Met Ile Glu Gly Thr Ala Glu Val
    290                 295                 300
```

-continued

```
Phe Ser Arg Leu Asn Glu Val Ser Lys Ala Ala Ser Lys Met Gly Lys
305                 310                 315                 320

Ala Gln Xaa


<210> SEQ ID NO 18
<211> LENGTH: 288
<212> TYPE: PRT
<213> ORGANISM: Homo sapiens
<220> FEATURE:
<221> NAME/KEY: VARIANT
<222> LOCATION: (288)...(288)
<223> OTHER INFORMATION: Xaa = Unknown or other at position 288

<400> SEQUENCE: 18

Leu Leu Glu Pro Val Ser Ile Gly Gly Ile Pro Ala Val Gln Ala Gln
 1               5                  10                  15

Ala Gly Trp Leu Gln His Asp Phe Gly His Leu Ser Val Phe Ser Thr
            20                  25                  30

Ser Lys Trp Asn His Leu Leu His His Phe Val Ile Gly His Leu Lys
        35                  40                  45

Gly Ala Pro Ala Ser Trp Trp Asn His Met His Phe Gln His His Ala
    50                  55                  60

Lys Pro Asn Cys Phe Arg Lys Asp Pro Asp Ile Asn Met His Pro Phe
65                  70                  75                  80

Phe Phe Ala Leu Gly Lys Ile Leu Ser Val Glu Leu Gly Lys Gln Lys
                85                  90                  95

Lys Lys Tyr Met Pro Tyr Asn His Gln His Lys Tyr Phe Phe Leu Ile
            100                 105                 110

Gly Pro Pro Ala Leu Leu Pro Leu Tyr Phe Gln Trp Tyr Ile Phe Tyr
        115                 120                 125

Phe Val Ile Gln Arg Lys Lys Trp Val Asp Leu Ala Trp Met Ile Thr
    130                 135                 140

Phe Tyr Val Arg Phe Phe Leu Thr Tyr Val Pro Leu Leu Gly Leu Lys
145                 150                 155                 160

Ala Phe Leu Gly Leu Phe Phe Ile Val Arg Phe Leu Glu Ser Asn Trp
                165                 170                 175

Phe Val Trp Val Thr Gln Met Asn His Ile Pro Met His Ile Asp His
            180                 185                 190

Asp Arg Asn Met Asp Trp Val Ser Thr Gln Leu Gln Ala Thr Cys Asn
        195                 200                 205

Val His Lys Ser Ala Phe Asn Asp Trp Phe Ser Gly His Leu Asn Phe
    210                 215                 220

Gln Ile Glu His His Leu Phe Pro Thr Met Pro Arg His Asn Tyr His
225                 230                 235                 240

Lys Val Ala Pro Leu Val Gln Ser Leu Cys Ala Lys His Gly Ile Glu
                245                 250                 255

Tyr Gln Ser Lys Pro Leu Leu Ser Ala Phe Ala Asp Ile Ile His Ser
            260                 265                 270

Leu Lys Glu Ser Gly Gln Leu Trp Leu Asp Ala Tyr Leu His Gln Xaa
        275                 280                 285


<210> SEQ ID NO 19
<211> LENGTH: 356
<212> TYPE: PRT
<213> ORGANISM: Homo sapiens
<220> FEATURE:
<221> NAME/KEY: VARIANT
```

-continued

<222> LOCATION: (294)...(294)
<223> OTHER INFORMATION: Xaa = Unknown or other at position 294
<221> NAME/KEY: VARIANT
<222> LOCATION: (320)...(320)
<223> OTHER INFORMATION: Xaa = Unknown or other at position 320

<400> SEQUENCE: 19

```
Val Phe Tyr Phe Gly Asn Gly Trp Ile Pro Thr Leu Ile Thr Ala Phe
 1               5                  10                  15

Val Leu Ala Thr Ser Gln Ala Gln Ala Gly Trp Leu Gln His Asp Tyr
            20                  25                  30

Gly His Leu Ser Val Tyr Arg Lys Pro Lys Trp Asn His Leu Val His
        35                  40                  45

Lys Phe Val Ile Gly His Leu Lys Gly Ala Ser Ala Asn Trp Trp Asn
    50                  55                  60

His Arg His Phe Gln His His Ala Lys Pro Asn Ile Phe His Lys Asp
65                  70                  75                  80

Pro Asp Val Asn Met Leu His Val Phe Val Leu Gly Glu Trp Gln Pro
                85                  90                  95

Ile Glu Tyr Gly Lys Lys Lys Leu Lys Tyr Leu Pro Tyr Asn His Gln
            100                 105                 110

His Glu Tyr Phe Phe Leu Ile Gly Pro Pro Leu Leu Ile Pro Met Tyr
        115                 120                 125

Phe Gln Tyr Gln Ile Ile Met Thr Met Ile Val His Lys Asn Trp Val
    130                 135                 140

Asp Leu Ala Trp Ala Val Ser Tyr Tyr Ile Arg Phe Phe Ile Thr Ile
145                 150                 155                 160

Pro Phe Tyr Gly Ile Leu Gly Ala Leu Leu Phe Leu Asn Phe Ile Arg
                165                 170                 175

Phe Leu Glu Ser His Trp Phe Val Trp Val Thr Gln Met Asn His Ile
            180                 185                 190

Val Met Glu Ile Asp Gln Glu Ala Tyr Arg Asp Trp Phe Ser Ser Gln
        195                 200                 205

Leu Thr Ala Thr Cys Asn Val Glu Gln Ser Phe Phe Asn Asp Trp Phe
    210                 215                 220

Ser Gly His Leu Asn Phe Gln Ile Glu His His Leu Phe Pro Thr Met
225                 230                 235                 240

Pro Arg His Asn Leu His Lys Ile Ala Pro Leu Val Lys Ser Leu Cys
                245                 250                 255

Ala Lys His Gly Ile Glu Tyr Gln Glu Lys Pro Leu Leu Arg Ala Leu
            260                 265                 270

Leu Asp Ile Ile Arg Ser Leu Lys Lys Ser Gly Lys Leu Trp Leu Asp
        275                 280                 285

Ala Tyr Leu His Lys Xaa Ser His Ser Pro Arg Asp Thr Val Gly Lys
    290                 295                 300

Gly Cys Arg Trp Gly Asp Gly Gln Arg Asn Asp Gly Leu Leu Phe Xaa
305                 310                 315                 320

Gly Val Ser Glu Arg Leu Val Tyr Ala Leu Leu Thr Asp Pro Met Leu
                325                 330                 335

Asp Leu Ser Pro Phe Leu Leu Ser Phe Phe Ser Ser His Leu Pro His
            340                 345                 350

Ser Thr Leu Pro
        355
```

<210> SEQ ID NO 20

-continued

<211> LENGTH: 219
<212> TYPE: PRT
<213> ORGANISM: Homo sapiens

<400> SEQUENCE: 20

```
Leu Leu Glu Pro Val Ser Ile Gly Gly Ile Pro Ala Val Gln Ala Gln
 1               5                  10                  15

Ala Gly Trp Leu Gln His Asp Phe Gly His Leu Ser Val Phe Ser Thr
            20                  25                  30

Ser Lys Trp Asn His Leu Leu His His Phe Val Ile Gly His Leu Lys
        35                  40                  45

Gly Ala Pro Ala Ser Trp Trp Asn His Met His Phe Gln His His Ala
    50                  55                  60

Lys Pro Asn Cys Phe Arg Lys Asp Pro Asp Ile Asn Met His Pro Phe
65                  70                  75                  80

Phe Phe Ala Leu Gly Lys Ile Leu Ser Val Glu Leu Gly Lys Gln Lys
                85                  90                  95

Lys Lys Tyr Met Pro Tyr Asn His Gln His Lys Tyr Phe Phe Leu Ile
            100                 105                 110

Gly Pro Pro Ala Leu Leu Pro Leu Tyr Phe Gln Trp Tyr Ile Phe Tyr
        115                 120                 125

Phe Val Ile Gln Arg Lys Lys Trp Val Asp Leu Ala Trp Met Ile Thr
    130                 135                 140

Phe Tyr Val Arg Phe Phe Leu Thr Tyr Val Pro Leu Leu Gly Leu Lys
145                 150                 155                 160

Ala Phe Leu Gly Leu Phe Phe Ile Val Arg Phe Leu Glu Ser Asn Trp
                165                 170                 175

Phe Val Trp Val Thr Gln Met Asn His Ile Pro Met His Ile Asp His
            180                 185                 190

Asp Arg Asn Met Asp Trp Val Ser Thr Gln Leu Gln Ala Thr Cys Asn
        195                 200                 205

Val His Lys Ser Ala Phe Asn Asp Trp Phe Ser
    210                 215
```

<210> SEQ ID NO 21
<211> LENGTH: 182
<212> TYPE: PRT
<213> ORGANISM: Homo sapiens
<220> FEATURE:
<221> NAME/KEY: VARIANT
<222> LOCATION: (128)...(128)
<223> OTHER INFORMATION: Xaa = Unknown or other at position 128

<400> SEQUENCE: 21

```
Leu His Ile Leu Leu Leu Asp Gly Ala Ala Trp Leu Thr Leu Trp Val
 1               5                  10                  15

Phe Gly Thr Ser Phe Leu Pro Phe Leu Leu Cys Ala Val Leu Leu Ser
            20                  25                  30

Ala Val Gln Ala Gln Ala Gly Trp Leu Gln His Asp Phe Gly His Leu
        35                  40                  45

Ser Val Phe Ser Thr Ser Lys Trp Asn His Leu Leu His His Phe Val
    50                  55                  60

Ile Gly His Leu Lys Gly Ala Pro Ala Ser Trp Trp Asn His Met His
65                  70                  75                  80

Phe Gln His His Ala Lys Pro Asn Cys Phe Arg Lys Asp Pro Asp Ile
                85                  90                  95

Asn Met His Pro Phe Phe Phe Ala Leu Gly Lys Ile Leu Ser Val Glu
```

-continued

```
            100                 105                 110

Leu Gly Lys Gln Lys Lys Lys Tyr Met Pro Tyr Asn His Gln His Xaa
        115                 120                 125

Tyr Phe Phe Leu Ile Gly Pro Pro Ala Leu Leu Pro Leu Tyr Phe Gln
    130                 135                 140

Trp Tyr Ile Phe Tyr Phe Val Ile Gln Arg Lys Lys Trp Val Asp Leu
145                 150                 155                 160

Ala Trp Ile Ser Lys Gln Glu Tyr Asp Glu Ala Gly Leu Pro Leu Ser
                165                 170                 175

Thr Ala Asn Ala Ser Lys
            180


<210> SEQ ID NO 22
<211> LENGTH: 179
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Xaa = Unknown or other at position 1
<221> NAME/KEY: VARIANT
<222> LOCATION: (11)...(11)
<223> OTHER INFORMATION: Xaa = Unknown or other at position 11
<221> NAME/KEY: VARIANT
<222> LOCATION: (19)...(19)
<223> OTHER INFORMATION: Xaa = Unknown or other at position 19
<221> NAME/KEY: VARIANT
<222> LOCATION: (139)...(139)
<223> OTHER INFORMATION: Xaa = Unknown or other at position 139
<221> NAME/KEY: VARIANT
<222> LOCATION: (163)...(163)
<223> OTHER INFORMATION: Xaa = Unknown or other at position 163
<221> NAME/KEY: VARIANT
<222> LOCATION: (172)...(172)
<223> OTHER INFORMATION: Xaa = Unknown or other at position 172

<400> SEQUENCE: 22

Xaa Leu Asp Leu Pro Thr Asn Met Met Glu Xaa Arg Lys Ala Ala Ala
 1               5                  10                  15

Glu Leu Xaa Ala Ala Glu Thr Ala Ala Gln Gly Pro Thr Pro Arg Tyr
            20                  25                  30

Phe Thr Trp Asp Glu Val Ala Gln Arg Ser Gly Cys Glu Glu Arg Trp
        35                  40                  45

Leu Val Ile Asp Arg Lys Val Tyr Asn Ile Ser Glu Phe Thr Arg Arg
    50                  55                  60

His Pro Gly Gly Ser Arg Val Ile Ser His Tyr Ala Gly Gln Asp Ala
65                  70                  75                  80

Thr Asp Pro Phe Val Ala Phe His Ile Asn Lys Gly Leu Val Lys Lys
                85                  90                  95

Tyr Met Asn Ser Leu Leu Ile Gly Glu Leu Ser Pro Glu Gln Pro Ser
            100                 105                 110

Phe Glu Pro Thr Lys Asn Lys Glu Leu Thr Asp Glu Phe Arg Glu Leu
        115                 120                 125

Arg Ala Thr Val Glu Gln Arg Phe Pro Val Xaa Phe Leu Thr Cys Thr
    130                 135                 140

Gly Ala His Gly Phe Phe Ser Leu Glu Val Pro Gly Leu Pro Asp Ser
145                 150                 155                 160

Asn Lys Xaa Phe Ser Trp Thr Ser Arg Pro Ile Xaa Trp Asn Lys Gly
                165                 170                 175

Lys Arg Pro
```

-continued

<210> SEQ ID NO 23
<211> LENGTH: 133
<212> TYPE: PRT
<213> ORGANISM: Homo sapiens

<400> SEQUENCE: 23

```
Ala Glu Gln Ser Asp Glu Ala Val Lys Tyr Tyr Thr Leu Glu Glu Ile
 1               5                  10                  15

Gln Lys His Asn His Ser Lys Ser Thr Trp Leu Ile Leu His His Lys
            20                  25                  30

Val Tyr Asp Leu Thr Lys Phe Leu Glu Glu His Pro Gly Gly Glu Glu
        35                  40                  45

Val Leu Arg Glu Gln Ala Gly Gly Asp Ala Thr Glu Asn Phe Glu Asp
    50                  55                  60

Val Gly His Ser Thr Asp Ala Arg Glu Met Ser Lys Thr Phe Ile Ile
65                  70                  75                  80

Gly Glu Leu His Pro Asp Asp Arg Pro Lys Leu Asn Lys Pro Pro Glu
                85                  90                  95

Thr Leu Ile Thr Thr Ile Asp Ser Ser Ser Ser Trp Trp Thr Asn Trp
            100                 105                 110

Val Ile Pro Ala Ile Ser Ala Val Ala Val Ala Leu Met Tyr Arg Leu
        115                 120                 125

Tyr Met Ala Glu Asp
    130
```

<210> SEQ ID NO 24
<211> LENGTH: 300
<212> TYPE: DNA
<213> ORGANISM: Homo sapiens

<400> SEQUENCE: 24

```
cccgaccaat atgatggaat aaaggaaagc ggccgctgaa ttataggccg ccgagaccgc     60

ggctcaggga cctaccccgc gttacttcac atgggacgag gtggcccagc gctcagggtg    120

cgaggagcgg tggcttgtga tcgaccgtaa ggtgtacaac atcagcgagt tcacccgccg    180

gcatccaggg ggctcccggg tcatcagcca ctacgccggg caggatgcca cggatccctt    240

cgtggccttc cacatcaaca agggccttgt gaagaagtat atgaactctc tcctgattgg    300
```

<210> SEQ ID NO 25
<211> LENGTH: 300
<212> TYPE: DNA
<213> ORGANISM: Homo sapiens

<400> SEQUENCE: 25

```
cccggcgcgc ggcgtcgcca ggccagctat ggcccccgac ccggtggccg ccgagaccgc     60

ggctcaggga cctaccccgc gctacttcac ctgggacgag gtggcccagc gctcagggtg    120

cgaggagcgg tggctagtga tcgaccgtaa ggtgtacaac atcagcgagt tcacccgccg    180

gcatccaggg ggctcccggg tcatcagcca ctacgccggg caggatgcca cggtgagcgc    240

agccaggcgg gggcacagga gagggcggga ccggaggctg agtgcagggg agacagagtt    300
```

<210> SEQ ID NO 26
<211> LENGTH: 360
<212> TYPE: DNA
<213> ORGANISM: Homo sapiens

<400> SEQUENCE: 26

-continued aatacgactc actatagggc tcgagcggcc gcccgggcag gtccggacct gccaacgtga 60
atcttatcgc catggacctt accttgcaca acccaaagta gctgccttgg ggcagggggt 120
ggccagagtg cttagggaaa tgtggagccc tacccagaac aacggtggag ggaaagggaa 180
gaaacgcaga agtgccccag ttcggacgta gggaagtctt cctcttcgtg gtttttggag 240
aaccctagct aagagaggaa agggacttat tgaaagaccc gcaagaaggg acggaagtct 300
catagccctg agaggatccc tttgtggcct tccacatcaa caagggcctt gtgaagaagt 360

<210> SEQ ID NO 27
<211> LENGTH: 419
<212> TYPE: DNA
<213> ORGANISM: Homo sapiens

<400> SEQUENCE: 27
ccccgcccca cacgccgcat cacttacagg gcccggggct gccggacctg ccaacgtgaa 60
tcttatcgcc atggacctta ccttgcacaa cccaaagtag ctgccttggg gcaggggtg 120 gccagagtgc ttagggaaat gtggagccct acccagaaca acggtggagg gaaagggaag 180
aaacgcagaa gtgccccagt tcggacgtag ggaagtcttc ctcttcgtgg tttttggaga 240
accctagcta agagaggaaa gggacttatt gaaagacccg caagaaggga cggaagtcta 300
accctagcta agagaggaaa gggacttatt gaaagacccg caagaaggga cggaagtctc 360
atagccctga gaggtgaagc cagctggagt tgatgggtcg aatggggacc tagagaact 419

<210> SEQ ID NO 28
<211> LENGTH: 240
<212> TYPE: DNA
<213> ORGANISM: Homo sapiens

<400> SEQUENCE: 28
tatagggctc gagcggccgc ccgggcaggt gcccggaggc gcctgatcat acctgttgcc 60
cggtgattgg gtgtcctgcg gatgcgggat gaaaaggcgg gagagaggcc tggaaaagtg 120
gagtctgggg agtggggatg gaggccaaca acacgcacac acaaacaaag ggtcccgcct 180
ccctgccgtg cattccatct gcagccccga gcctcaggat ccctttgtgg ccttccacat 240

<210> SEQ ID NO 29
<211> LENGTH: 239
<212> TYPE: DNA
<213> ORGANISM: Homo sapiens

<400> SEQUENCE: 29
cgagccaaac accgactaat tcggaggaaa gcccggaggc gcctgatcat acctgttgcc 60
cggtgattgg gtgtcctgcg gatgcgggat gaaaaggcgg gagagaggcc tggagaagtg 120
gagtctgggg agtggggatg gaggccaaca acacgcacac acaaacaaag ggtcccgcct 180
ccctgccgtg cattccatct gcagccccga gcctcaggtc tctgggcggg gacagaacc 239

<210> SEQ ID NO 30
<211> LENGTH: 300
<212> TYPE: DNA
<213> ORGANISM: Homo sapiens

<400> SEQUENCE: 30
cgagcggccg cccgggcagg tctagaattc agcggccgct gaagccgcgt ctggacctag 60
gtgccggtct ccactcgcca gcaggagcgg agagggagca ggaaaggagc ccattctcga 120
ggatggggct gaaacgggaa gcttggggag accgctgcct tggggacccc tgcgtcgtgt 180

-continued gaagactgga ggacgcggaa gggacagcgc tggccgggga gggcaagcgg ccgctggcga 240
tccctttgtg gccttccaca tcaacaaggg ccttgtgaag aagtatatga actctctcct 300

<210> SEQ ID NO 31
<211> LENGTH: 299
<212> TYPE: DNA
<213> ORGANISM: Homo sapiens

<400> SEQUENCE: 31
agggagtcac atcctgtctc gatggctagg agaggcagcg cagccgcgtc tggacctagg 60
tgccggtctc cactcgccag caggagcgga gagggagcag gaaaggagcc cattctcgag 120
gatggggctg aaacgggaag cttggggaga ccgctgcctt ggggacccct gcgtcgtgtg 180
aagactggag gacgcggaag ggacagcgct ggccggggag ggcaagcggc cgctggcgta 240
cataagggat tgggaatggc atacacttag cgaggacccc cagagctgtt ctcgaatcg 299

<210> SEQ ID NO 32
<211> LENGTH: 286
<212> TYPE: DNA
<213> ORGANISM: Homo sapiens

<400> SEQUENCE: 32
ttattccctt atttgtccct gcccatgtcc tgctgattgg tccattttac ctctagctag 60
ctaaagagca cggattggtg cattttgcaa acctctggct acagaggggt tctccaggtc 120
tgcactcgac ccaggaagtc catctggctt cacctctcac ttcaacttgg gtacagcctt 180
ctggcgggca ggaagatggc ctttggtgcg aacactgccg gagtccaggg ggctggctcc 240
ctcacctttc atcttctccc ggcacttgca ggatcccttt gtggcc 286

<210> SEQ ID NO 33
<211> LENGTH: 286
<212> TYPE: DNA
<213> ORGANISM: Homo sapiens

<400> SEQUENCE: 33
atagagcact gattggtcca ttttacaggg tgctgattgg tccattttac ctctagctag 60
ctaaagagca cggattggtg cattttacaa acctctagct acagaaaagt tctccaagtc 120
tgcactcgac ccaggaagtc catctggctt cacctctcac ttcaacttgg gtacagcctt 180
ctggcgggca ggaggatggc ctttggtgcg aacactgccg gagtccaggg ggctggctcc 240
ctcacctttc atcttctccc ggcacttgca ggatcccttt gtggcc 286

<210> SEQ ID NO 34
<211> LENGTH: 4698
<212> TYPE: DNA
<213> ORGANISM: Homo sapiens

<400> SEQUENCE: 34
actagaaccg ctgttcctac cgcggcgccc cctgggagcc aacgccgcga tgcccgcctg 60
acgtcaggaa gtcgaatccg gcggcgacgc ttttagggag cccgcgaggg ggcgcgtgtt 120
ggcagcccag ctgtgagttg cccaagaccc accgggggac gggatctcgc tccccgcgcc 180
acgaggctcg gccaatggga acgcgcgctg cgaggcccgc cggtctgccc tgcggtgctg 240
aaaacccggc gcgcaggcgg ctggctctgg gcgcgcgcca gcaaatccac tcctggagcc 300
cgcggacccc gagcacgcgc ctgacagccc ctgctggccc ggcgcgcggc gtcgccaggc 360

-continued

```
cagctatggc ccccgacccg gtggccgccg agaccgcggc tcagggacct accccgcgct    420
acttcacctg ggacgaggtg gcccagcgct cagggtgcga ggagcggtgg ctagtgatcg    480
accgtaaggt gtacaacatc agcgagttca cccgccggca tccagggggc tcccgggtca    540
tcagccacta cgccgggcag gatgccacgg tgagcgcagc caggcggggg cacaggagag    600
ggcgggaccg gaggctgagt gcaggggaga cagagttacg cactccgagc caaacaccga    660
ctaattcgga ggaaagcccg gaggcgcctg atcatacctg ttgcccggtg attgggtgtc    720
ctgcggatgc gggatgaaaa ggcgggagag aggcctggag aagtggagtc tggggagtgg    780
ggatggaggc caacaacacg cacacacaaa caaagggtcc cgcctccctg ccgtgcattc    840
catctgcagc cccgagcctc aggtctctgg gcggggacag aaccccgagc tgggtaggct    900
aggagggagg agagcaagga tgcaggccgc ctggggaggg agggggtcag tggccagggg    960
agggagtcac atcctgtctc gatggctagg agaggcagcg cagccgcgtc tggacctagg   1020
tgccggtctc cactcgccag caggagcgga gagggagcag gaaaggagcc cattctcgag   1080
gatggggctg aaacgggaag cttggggaga ccgctgcctt ggggacccct gcgtcgtgtg   1140
aagactggag gacgcggaag ggacagcgct ggccggggag ggcaagcggc cgctggcgta   1200
cataagggat tgggaatggc atacacttag cgaggacccc cagagctgtt ctcgaatcgc   1260
ggggaggccc tgagccgcag gccagcgagg tcttcagcta ttccgcggag cggaccgctg   1320
tttacgctct ggggcggtag gcccttcgcg gggtcctgtc ccttcttccc ttggtctcac   1380
tgcggggtcg gcgcgcgccc cagccccagg cctgctgctt ccctttctag accacagccc   1440
tcagagctaa ggccccggcg cctctctgct gggttggagt cctggggact cagtcctagg   1500
gactcgaaag tcggggcgtt cccttcaccg cgtttccccc ttggcggcca gaatggcgtc   1560
ccctcccctt gcatccccct ctgatcccgt gccctgcagc gtgatgccct ccactgtccc   1620
tatccactac cctggcgtcc cagagtgtgc cgcgggtcac caggttccca taacgtcgca   1680
gcagagctta gacgctgcgg ggcgaagacc cgccccaccc tctgacgcga ccagcctagt   1740
gggcgaggcc agagcttgcg cgggtcaacc agagtgacca ctcgggagcc ctgactgcgg   1800
ccaagggcgc aggcgtgtcc cggcgcatgc gcagacgaaa caggcaccaa cgctggagct   1860
tcccgcagtg tgatttgggg ccggggatgc cgcggcgggg acggcgattg gtccgtatgt   1920
gtggtgccac cggccgccgc tccgccccgg cccccgcccc acacgccgca tcacttacag   1980
ggcccggggc tgccggacct gccaacgtga atcttatcgc catggacctt accttgcaca   2040
acccaaagta gctgccttgg ggcagggggt ggccagagtg cttagggaaa tgtggagccc   2100
tacccagaac aacggtggag ggaaagggaa gaaacgcaga agtgccccag ttcggacgta   2160
gggaagtctt cctcttcgtg gtttttggag aaccctagct aagagaggaa agggacttat   2220
tgaaagaccc gcaagaaggg acggaagtct catagccctg agaggtgaag ccagctggag   2280
ttgatgggtc gaatggggac ctagagaact tttctgtatc tagaggtttg taaaatgcac   2340
caatcagtgc tctgtaaaaa cgcaccaatt ggcgctctgt agctagctag aggtttgtaa   2400
aatgagccaa tcagcaggac gtgggcaggg acaactaaga caataaaagc tggccacccc   2460
agccagctgc tgcaacccgc tccagttccc ttacaggctg tggaagcatt gttcttttgc   2520
tcgtcacact aaaccttgct gctgctcatt ctttgggtct gcaaagagtg ttattccttt   2580
aagagctata acagcgggaa ggtccacggc tccattcttg aagtcagtga gaccataccc   2640
gccggaagga accaacgccc gacacagccc cacccatctc tcctgtttct cacctatact   2700
gaaattcttg ggcaaaagct gtctgtggac acacccaggg gaaaggccag cccaggcagg   2760
```

-continued

```
tgtttcttag tggttcccct cagccaatgc ttcccattcc ttgatgcatc cttctaacta   2820

gagcagatgc tcggtgatct taaactgtgg acacctggga gcaccctcaa aaggcagctg   2880

ggcctaggga gatggcctgt gcttctgtgt caggagttgg ttccttcagg tgggcttgtg   2940

gtctcgctga cgtcaagaat gaagccatga accttcgcgg tgagtgttac agctcttaca   3000

ggtggcgtgg acccaaagag tgagcagcag caagatttat tgtgaagagc aaagaacaaa   3060

gcttccacag cgtggaaggg tacccgagca ggttgccgct gctggacgtt gggggtgtg    3120

agggggagca gccttttttt ttcttttttt tttgagacgg agtctccctg tcgcccaggc   3180

tggagtgcag tggcgcgatc tcggctcact gcaggctccg cccccccccc ggggttcacg   3240

ccattctcct gcctcagcct cccgagtagc tgggactaca ggcgcccgct acctcgcccg   3300

gctaattttt tgtattttta gtagagacgg ggtttcactg tgttagccag gatggtctcg   3360

atctcctgac ctcgtgatcc acccgccttg gcctcccaaa gtgctgggat tacaggcgtg   3420

agccaccgcg cccggccggg agcagctttt attcccttat ttgtccctgc ccatgtcctg   3480

ctgatttgtc cattttatag agcactgatt ggtccatttt acagggtgct gattggtcca   3540

ttttacctct agctagctaa agagcacgga ttggtgcatt ttacaaacct ctagctacag   3600

aaaagttctc caagtctgca ctcgacccag gaagtccatc tggcttcacc tctcacttca   3660

acttgggtac agccttctgg cgggcaggag gatggccttt ggtgcgaaca ctgccggagt   3720

ccagggggct ggctccctca cctttcatct tctcccggca cttgcaggat ccctttgtgg   3780

ccttccacat caacaagggc cttgtgaaga agtatatgaa ctctctcctg attggagaac   3840

tgtctccaga gcagcccagc tttgagccca ccaagaatgt aagaccctgt gtttgctatg   3900

tcgcaactat tggttgttga gggggacaga gagggggtgg aaggagagtc tagatggaat   3960

cacagtcata gtaatcacag tcagtagtag ctctggggag tcttgaggtc cctgcttctc   4020

ttgcatagtc atgaggtcac aggcccaagg gagcatggct ttgcaaccta tggctccccc   4080

aaggctgcca ctaccatggc tgccatcatt gttatcatca ttgttatcat atgagcactt   4140

actatgcacc aagcataaac tcataactct tacacattta cagatgagat aacaggctca   4200

gggaggttaa gcaacacagc caaggatcac acagttagta aatggcagag caaggactta   4260

gtcccctgaa ctcttaggca ctatcccatg gcacctcctc ctgtcatcct cattgtcgtg   4320

gtatctttgc ctaggactgt ggacttccca cagctacctc agtgggaggt ccttgagcct   4380

gagagggccc ttgtctccag tagcattggg gtgcagatga gaagaataac agctcctctt   4440

cctcttctgc agaaagagct gacagatgag ttccgggagc tgcgggccac agtggagcgg   4500

atggggctca tgaaggccaa ccatgtcttc ttcctgctgt acctgctgca catcttgctg   4560

ctggatggtg cagcctggct caccctttgg gtctttggga cgtccttttt gcccttcctc   4620

ctctgtgcgg tgctgctcag tgcagttcag gtgagagcct ttggcttgtc aagtgcacag   4680

caatgctcag catccctg                                                 4698
```

<210> SEQ ID NO 35
<211> LENGTH: 990
<212> TYPE: DNA
<213> ORGANISM: Homo sapiens

<400> SEQUENCE: 35

```
atggccccog acccggtggc cgccgagacc gcggctcagg gacctacccc gcgctacttc     60

acctgggacg aggtggccca gcgctcaggg tgcgaggagc ggtggctagt gatcgaccgt    120
```

-continued

```
aaggtgtaca acatcagcga gttcacccgc cggcatccag ggggctcccg ggtcatcagc    180

cactacgccg ggcaggatgc cacggatccc tttgtggcct tccacatcaa caagggcctt    240

gtgaagaagt atatgaactc tctcctgatt ggagaactgt ctccagagca gcccagcttt    300

gagcccacca agaataaaga gctgacagat gagttccggg agctgcgggc cacagtggag    360

cggatggggc tcatgaaggc caaccatgtc ttcttcctgc tgtacctgct gcacatcttg    420

ctgctggatg gtgcagcctg gctcaccctt tgggtctttg ggacgtcctt tttgcccttc    480

ctcctctgtg cggtgctgct cagtgcagtt caggcccagg ctggctggct gcagcatgac    540

tttgggcacc tgtcggtctt cagcacctca aagtggaacc atctgctaca tcattttgtg    600

attggccacc tgaagggggc ccccgccagt tggtggaacc acatgcactt ccagcaccat    660

gccaagccca actgcttccg caaagaccca gacatcaaca tgcatccctt cttctttgcc    720

ttggggaaga tcctctctgt ggagcttggg aaacagaaga aaaaatatat gccgtacaac    780

caccagcaca aatacttctt cctaattggg cccccagcct tgctgcctct ctacttccag    840

tggtatattt tctattttgt tatccagcga cccccagcct tgctgcctct ctacttccag    900

tggtatattt tctattttgt tatccagcga aagaagtggg tggacttggc ctggatgatt    960

accttctacg tccgcttctt cctcacttat                                     990
```

<210> SEQ ID NO 36
<211> LENGTH: 960
<212> TYPE: DNA
<213> ORGANISM: Homo sapiens

<400> SEQUENCE: 36

```
ggcccggcgc gcggcgtcgc caggccagct atggcccccg acccggtggc cgccgagacc     60

gcggctcagg gacctacccc gcgctacttc acctgggacg aggtggccca gcgctcaggg    120

tgcgaggagc ggtggctagt gatcgaccgt aaggtgtaca acatcagcga gttcacccgc    180

cggcatccag ggggctcccg ggtcatcagc cactacgccg ggcaggatgc cacggatccc    240

tttgtggcct tccacatcaa caagggcctt gtgaagaagt atatgaactc tctcctgatt    300

ggagaactgt ctccagagca gcccagcttt gagcccacca agaataaaga gctgacagat    360

gagttccggg agctgcgggc cacagtggag cggatggggc tcatgaaggc caaccatgtc    420

ttcttcctgc tgtacctgct gcacatcttg ctgctggatg gtgcagcctg gctcaccctt    480

tgggtctttg ggacgtcctt tttgcccttc ctcctctgtg cggtgctgct cagtgcagtt    540

caggcccagg ctggctggct gcagcatgac tttgggcacc tgtcggtctt cagcacctca    600

aagtggaacc atctgctaca tcattttgtg attggccacc tgaagggggc ccccgccagt    660

tggtggaacc acatgcactt ccagcaccat gccaagccca actgcttccg caaagaccca    720

gacatcaaca tgcatccctt cttctttgcc ttggggaaga tcctctctgt ggagcttggg    780

aaacagaaga aaaaatatat gccgtacaac caccagcaca aatacttctt cctaattggg    840

cccccagcct tgctgcctct ctacttccag tggtatattt tctattttgt tatccagcga    900

aagaagtggg tggacttggc ctggatcagc aaacaggaat acgatgaagc cgggcttcca    960
```

<210> SEQ ID NO 37
<211> LENGTH: 473
<212> TYPE: DNA
<213> ORGANISM: Homo sapiens

<400> SEQUENCE: 37

```
tccagcgaaa gaagtgggtg gacttggcct ggatgattac cttctacgtc cgcttcttcc     60
```

-continued

```
tcacttatgt gccactattg gggctgaaag ccttcctggg ccttttcttc atagtcaggt    120

tcctggaaag caactggttt gtgtgggtga cacagatgaa ccatattccc atgcacattg    180

atcatgaccg gaacatggac tgggtttcca cccagctcct ggccacatgc aatgtccaca    240

agtctgcctt caatgactgg ttcagtggac acctcaactt ccagattgag caccatcttt    300

ttcccacgat gcctcgacac aattaccaca aagtggctcc cctggtgcag tccttgtgtg    360

ccaagcgtgg catagagtac cagtccaagc ccctgctgtc agccttcgcc gacatcatcc    420

actcactaaa ggagtcaggg cagctctggc tagatgccta tcttcaccaa taa           473


<210> SEQ ID NO 38
<211> LENGTH: 449
<212> TYPE: DNA
<213> ORGANISM: Homo sapiens
<220> FEATURE:
<221> NAME/KEY: misc_feature
<222> LOCATION: (5)...(5)
<223> OTHER INFORMATION: k = g or t/u at position 5
<221> NAME/KEY: misc_feature
<222> LOCATION: (6)...(6)
<223> OTHER INFORMATION: m = a or c at position 6

<400> SEQUENCE: 38

gaatkmttac cttctacgtc cgcttcttcc tcacttatgt gccactattg gggctgaaag     60

cttcctgggc cttttcttca tagtcaggtt cctggaaagc aactggtttg tgtgggtgac    120

acagatgaac catattccca tgcacattga tcatgaccgg aacatggact gggtttccac    180

ccagctccag gccacatgca atgtccacaa gtctgccttc aatgactggt tcagtggaca    240

cctcaacttc cagattgagc accatctttt tcccacgatg cctcgacaca attaccacaa    300

agtggctccc ctggtgcagt ccttgtgtgc caagcatggc atagagtacc agtccaagcc    360

cctgctgtca gccttcgccg acatcatcca ctcactaaag gagtcagggc agctctggct    420

agatgcctat cttcaccaat aacaacagc                                      449


<210> SEQ ID NO 39
<211> LENGTH: 445
<212> TYPE: PRT
<213> ORGANISM: Homo sapiens
<220> FEATURE:
<221> NAME/KEY: VARIANT
<222> LOCATION: (445)...(445)
<223> OTHER INFORMATION: Xaa = Unknown or other at position 445

<400> SEQUENCE: 39

Met Ala Pro Asp Pro Val Ala Ala Glu Thr Ala Ala Gln Gly Pro Thr
 1               5                  10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110
```

-continued

```
Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140

Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
            180                 185                 190

Asn His Leu Leu His His Phe Val Ile Gly His Leu Lys Gly Ala Pro
        195                 200                 205

Ala Ser Trp Trp Asn His Met His Phe Gln His His Ala Lys Pro Asn
    210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
            260                 265                 270

Ala Leu Leu Pro Leu Tyr Phe Gln Trp Tyr Ile Phe Tyr Phe Val Ile
        275                 280                 285

Gln Arg Lys Lys Trp Val Asp Leu Ala Trp Met Ile Thr Phe Tyr Val
    290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
                325                 330                 335

Val Thr Gln Met Asn His Ile Pro Met His Ile Asp His Asp Arg Asn
            340                 345                 350

Met Asp Trp Val Ser Thr Gln Leu Leu Ala Thr Cys Asn Val His Lys
        355                 360                 365

Ser Ala Phe Asn Asp Trp Phe Ser Gly His Leu Asn Phe Gln Ile Glu
    370                 375                 380

His His Leu Phe Pro Thr Met Pro Arg His Asn Tyr His Lys Val Ala
385                 390                 395                 400

Pro Leu Val Gln Ser Leu Cys Ala Lys Arg Gly Ile Glu Tyr Gln Ser
                405                 410                 415

Lys Pro Leu Leu Ser Ala Phe Ala Asp Ile Ile His Ser Leu Lys Glu
            420                 425                 430

Ser Gly Gln Leu Trp Leu Asp Ala Tyr Leu His Gln Xaa
        435                 440                 445


<210> SEQ ID NO 40
<211> LENGTH: 465
<212> TYPE: PRT
<213> ORGANISM: Homo sapiens
<220> FEATURE:
<221> NAME/KEY: VARIANT
<222> LOCATION: (432)...(432)
<223> OTHER INFORMATION: Xaa = Unknown or other at position 432
<221> NAME/KEY: VARIANT
<222> LOCATION: (458)...(458)
<223> OTHER INFORMATION: Xaa = Unknown or other at position 458

<400> SEQUENCE: 40

Gln Gly Pro Thr Pro Arg Tyr Phe Thr Trp Asp Glu Val Ala Gln Arg
```

-continued

```
 1               5                   10                  15

Ser Gly Cys Glu Glu Arg Trp Leu Val Ile Asp Arg Lys Val Tyr Asn
            20                  25                  30

Ile Ser Glu Phe Thr Arg Arg His Pro Gly Gly Ser Arg Val Ile Ser
        35                  40                  45

His Tyr Ala Gly Gln Asp Ala Thr Asp Pro Phe Val Ala Phe His Ile
    50                  55                  60

Asn Lys Gly Leu Val Lys Lys Tyr Met Asn Ser Leu Leu Ile Gly Glu
65                  70                  75                  80

Leu Ser Pro Glu Gln Pro Ser Phe Glu Pro Thr Lys Asn Lys Glu Leu
                85                  90                  95

Thr Asp Glu Phe Arg Glu Leu Arg Ala Thr Val Glu Arg Met Gly Leu
            100                 105                 110

Met Lys Ala Asn His Val Phe Phe Leu Leu Tyr Leu Leu His Ile Leu
        115                 120                 125

Leu Leu Asp Gly Ala Ala Trp Leu Thr Leu Trp Val Phe Gly Thr Ser
    130                 135                 140

Phe Leu Pro Phe Leu Leu Cys Ala Val Leu Leu Ser Ala Val Gln Ala
145                 150                 155                 160

Gln Ala Gly Trp Leu Gln His Asp Tyr Gly His Leu Ser Val Tyr Arg
                165                 170                 175

Lys Pro Lys Trp Asn His Leu Val His Lys Phe Val Ile Gly His Leu
            180                 185                 190

Lys Gly Ala Ser Ala Asn Trp Trp Asn His Arg His Phe Gln His His
        195                 200                 205

Ala Lys Pro Asn Ile Phe His Lys Asp Pro Asp Val Asn Met Leu His
    210                 215                 220

Val Phe Val Leu Gly Glu Trp Gln Pro Ile Glu Tyr Gly Lys Lys Lys
225                 230                 235                 240

Leu Lys Tyr Leu Pro Tyr Asn His Gln His Glu Tyr Phe Phe Leu Ile
                245                 250                 255

Gly Pro Pro Leu Leu Ile Pro Met Tyr Phe Gln Tyr Gln Ile Ile Met
            260                 265                 270

Thr Met Ile Val His Lys Asn Trp Val Asp Leu Ala Trp Ala Val Ser
        275                 280                 285

Tyr Tyr Ile Arg Phe Phe Ile Thr Tyr Ile Pro Phe Tyr Gly Ile Leu
    290                 295                 300

Gly Ala Leu Leu Phe Leu Asn Phe Ile Arg Phe Leu Glu Ser His Trp
305                 310                 315                 320

Phe Val Trp Val Thr Gln Met Asn His Ile Val Met Glu Ile Asp Gln
                325                 330                 335

Glu Ala Tyr Arg Asp Trp Phe Ser Ser Gln Leu Thr Ala Thr Cys Asn
            340                 345                 350

Val Glu Gln Ser Phe Phe Asn Asp Trp Phe Ser Gly His Leu Asn Phe
        355                 360                 365

Gln Ile Glu His His Leu Phe Pro Thr Met Pro Arg His Asn Leu His
    370                 375                 380

Lys Ile Ala Pro Leu Val Lys Ser Leu Cys Ala Lys His Gly Ile Glu
385                 390                 395                 400

Tyr Gln Glu Lys Pro Leu Leu Arg Ala Leu Leu Asp Ile Ile Arg Ser
                405                 410                 415

Leu Lys Lys Ser Gly Lys Leu Trp Leu Asp Ala Tyr Leu His Lys Xaa
            420                 425                 430
```

-continued

```
Ser His Ser Pro Arg Asp Thr Val Gly Lys Gly Cys Arg Trp Gly Asp
        435                 440                 445

Gly Gln Arg Asn Asp Gly Leu Leu Phe Xaa Gly Val Ser Glu Arg Leu
    450                 455                 460

Val
465


<210> SEQ ID NO 41
<211> LENGTH: 360
<212> TYPE: PRT
<213> ORGANISM: Homo sapiens

<400> SEQUENCE: 41

Met Ala Pro Asp Pro Val Ala Ala Glu Thr Ala Ala Gln Gly Pro Thr
 1               5                  10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140

Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
            180                 185                 190

Asn His Leu Leu His His Phe Val Ile Gly His Leu Lys Gly Ala Pro
        195                 200                 205

Ala Ser Trp Trp Asn His Met His Phe Gln His His Ala Lys Pro Asn
    210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
            260                 265                 270

Ala Leu Leu Pro Leu Tyr Phe Gln Trp Tyr Ile Phe Tyr Phe Val Ile
        275                 280                 285

Gln Arg Lys Lys Trp Val Asp Leu Ala Trp Met Ile Thr Phe Tyr Val
    290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
```

-continued

```
                325                 330                 335

Val Thr Gln Met Asn His Ile Pro Met His Ile Asp His Asp Arg Asn
            340                 345                 350

Met Asp Trp Val Ser Thr Gln Leu
        355                 360


<210> SEQ ID NO 42
<211> LENGTH: 347
<212> TYPE: PRT
<213> ORGANISM: Homo sapiens
<220> FEATURE:
<221> NAME/KEY: VARIANT
<222> LOCATION: (251)...(251)
<223> OTHER INFORMATION: Xaa = Unknown or other at position 251
<221> NAME/KEY: VARIANT
<222> LOCATION: (329)...(330)
<223> OTHER INFORMATION: Xaa = Unknown or other at these positions

<400> SEQUENCE: 42

Gln Gly Pro Thr Pro Arg Tyr Phe Thr Trp Asp Glu Val Ala Gln Arg
 1               5                  10                  15

Ser Gly Cys Glu Glu Arg Trp Leu Val Ile Asp Arg Lys Val Tyr Asn
            20                  25                  30

Ile Ser Glu Phe Thr Arg Arg His Pro Gly Gly Ser Arg Val Ile Ser
        35                  40                  45

His Tyr Ala Gly Gln Asp Ala Thr Asp Pro Phe Val Ala Phe His Ile
    50                  55                  60

Asn Lys Gly Leu Val Lys Lys Tyr Met Asn Ser Leu Leu Ile Gly Glu
65                  70                  75                  80

Leu Ser Pro Glu Gln Pro Ser Phe Glu Pro Thr Lys Asn Lys Glu Leu
                85                  90                  95

Thr Asp Glu Phe Arg Glu Leu Arg Ala Thr Val Glu Arg Met Gly Leu
            100                 105                 110

Met Lys Ala Asn His Val Phe Phe Leu Leu Tyr Leu Leu His Ile Leu
        115                 120                 125

Leu Leu Asp Gly Ala Ala Trp Leu Thr Leu Trp Val Phe Gly Thr Ser
    130                 135                 140

Phe Leu Pro Phe Leu Leu Cys Ala Val Leu Leu Ser Ala Val Gln Ala
145                 150                 155                 160

Gln Ala Gly Trp Leu Gln His Asp Gly His Leu Ser Val Phe Ser Thr
                165                 170                 175

Ser Lys Trp Asn His Leu Leu His His Phe Val Ile Gly His Leu Lys
            180                 185                 190

Gly Ala Pro Ala Ser Trp Trp Asn His Met His Phe Gln His His Ala
        195                 200                 205

Lys Pro Asn Cys Phe Arg Lys Asp Pro Asp Ile Asn Met His Pro Phe
    210                 215                 220

Phe Phe Ala Leu Gly Lys Ile Leu Ser Val Glu Leu Gly Lys Gln Lys
225                 230                 235                 240

Lys Lys Tyr Met Pro Tyr Asn His Gln His Xaa Tyr Phe Phe Leu Ile
                245                 250                 255

Gly Pro Pro Ala Leu Leu Pro Leu Tyr Phe Gln Trp Tyr Ile Phe Tyr
            260                 265                 270

Phe Val Ile Gln Arg Lys Lys Trp Val Asp Leu Ala Trp Ile Ser Lys
        275                 280                 285

Gln Glu Tyr Asp Glu Ala Gly Leu Pro Leu Ser Thr Ala Asn Ala Ser
    290                 295                 300
```

-continued

```
Lys Arg Asp Leu Pro Arg Ala Thr Ser Pro Gly Thr Arg Trp Pro Ser
305                 310                 315                 320

Ala Gln Gly Ala Arg Ser Gly Gly Xaa Xaa Ser Thr Val Arg Cys Thr
                325                 330                 335

Thr Ser Ala Ser Ser Pro Ala Gly Ile Gln Gly
            340                 345


<210> SEQ ID NO 43
<211> LENGTH: 444
<212> TYPE: PRT
<213> ORGANISM: Homo sapiens
<220> FEATURE:
<221> NAME/KEY: VARIANT
<222> LOCATION: (444)...(444)
<223> OTHER INFORMATION: Xaa = Unknown or other at position 444

<400> SEQUENCE: 43

Met Ala Pro Asp Pro Val Ala Ala Glu Thr Ala Ala Gln Gly Pro Thr
 1               5                  10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Glu Leu Arg Ala Thr Val Glu Arg Met Gly Leu Met Lys Ala Asn His
        115                 120                 125

Val Phe Phe Leu Leu Tyr Leu Leu His Ile Leu Leu Leu Asp Gly Ala
    130                 135                 140

Ala Trp Leu Thr Leu Trp Val Phe Gly Thr Ser Phe Leu Pro Phe Leu
145                 150                 155                 160

Leu Cys Ala Val Leu Leu Ser Ala Val Gln Ala Gln Ala Gly Trp Leu
                165                 170                 175

Gln His Asp Phe Gly His Leu Ser Val Phe Ser Thr Ser Lys Trp Asn
            180                 185                 190

His Leu Leu His His Phe Val Ile Gly His Leu Lys Gly Ala Pro Ala
        195                 200                 205

Ser Trp Trp Asn His Met His Phe Gln His His Ala Lys Pro Asn Cys
    210                 215                 220

Phe Arg Lys Asp Pro Asp Ile Asn Met His Pro Phe Phe Phe Ala Leu
225                 230                 235                 240

Gly Lys Ile Leu Ser Val Glu Leu Gly Lys Gln Lys Lys Lys Tyr Met
                245                 250                 255

Pro Tyr Asn His Gln His Lys Tyr Phe Phe Leu Ile Gly Pro Pro Ala
            260                 265                 270

Leu Leu Pro Leu Tyr Phe Gln Trp Tyr Ile Phe Tyr Phe Val Ile Gln
        275                 280                 285

Arg Lys Lys Trp Val Asp Leu Ala Trp Met Ile Thr Phe Tyr Val Arg
    290                 295                 300
```

-continued

```
Phe Phe Leu Thr Tyr Val Pro Leu Leu Gly Leu Lys Ala Phe Leu Gly
305                 310                 315                 320

Leu Phe Phe Ile Val Arg Phe Leu Glu Ser Asn Trp Phe Val Trp Val
                325                 330                 335

Thr Gln Met Asn His Ile Pro Met His Ile Asp His Asp Arg Asn Met
            340                 345                 350

Asp Trp Val Ser Thr Gln Leu Leu Ala Thr Cys Asn Val His Lys Ser
        355                 360                 365

Ala Phe Asn Asp Trp Phe Ser Gly His Leu Asn Phe Gln Ile Glu His
    370                 375                 380

His Leu Phe Pro Thr Met Pro Arg His Asn Tyr His Lys Val Ala Pro
385                 390                 395                 400

Leu Val Gln Ser Leu Cys Ala Lys Arg Gly Ile Glu Tyr Gln Ser Lys
                405                 410                 415

Pro Leu Leu Ser Ala Phe Ala Asp Ile Ile His Ser Leu Lys Glu Ser
            420                 425                 430

Gly Gln Leu Trp Leu Asp Ala Tyr Leu His Gln Xaa
        435                 440


<210> SEQ ID NO 44
<211> LENGTH: 458
<212> TYPE: PRT
<213> ORGANISM: Homo sapiens
<220> FEATURE:
<221> NAME/KEY: VARIANT
<222> LOCATION: (458)...(458)
<223> OTHER INFORMATION: Xaa = Unknown or other at position 458

<400> SEQUENCE: 44

Met Ala Ala Ala Pro Ser Val Arg Thr Phe Thr Arg Ala Glu Val Leu
 1               5                  10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
```

-continued

```
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln Xaa
    450                 455


<210> SEQ ID NO 45
<211> LENGTH: 445
<212> TYPE: PRT
<213> ORGANISM: Homo sapiens
<220> FEATURE:
<221> NAME/KEY: VARIANT
<222> LOCATION: (445)...(445)
<223> OTHER INFORMATION: Xaa = Unknown or other at position 445

<400> SEQUENCE: 45

Met Ala Pro Asp Pro Val Ala Ala Glu Thr Ala Ala Gln Gly Pro Thr
 1               5                  10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110
```

-continued

Arg Glu Leu Arg Ala Thr Val Glu Arg Met Gly Leu Met Lys Ala Asn
115 120 125

His Val Phe Phe Leu Leu Tyr Leu Leu His Ile Leu Leu Leu Asp Gly
130 135 140

Ala Ala Trp Leu Thr Leu Trp Val Phe Gly Thr Ser Phe Leu Pro Phe
145 150 155 160

Leu Leu Cys Ala Val Leu Leu Ser Ala Val Gln Ala Gln Ala Gly Trp
165 170 175

Leu Gln His Asp Phe Gly His Leu Ser Val Phe Ser Thr Ser Lys Trp
180 185 190

Asn His Leu Leu His His Phe Val Ile Gly His Leu Lys Gly Ala Pro
195 200 205

Ala Ser Trp Trp Asn His Met His Phe Gln His His Ala Lys Pro Asn
210 215 220

Cys Phe Arg Lys Asp Pro Asp Ile Asn Met His Pro Phe Phe Phe Ala
225 230 235 240

Leu Gly Lys Ile Leu Ser Val Glu Leu Gly Lys Gln Lys Lys Lys Tyr
245 250 255

Met Pro Tyr Asn His Gln His Lys Tyr Phe Phe Leu Ile Gly Pro Pro
260 265 270

Ala Leu Leu Pro Leu Tyr Phe Gln Trp Tyr Ile Phe Tyr Phe Val Ile
275 280 285

Gln Arg Lys Lys Trp Val Asp Leu Ala Trp Met Ile Thr Phe Tyr Val
290 295 300

Arg Phe Phe Leu Thr Tyr Val Pro Leu Leu Gly Leu Lys Ala Phe Leu
305 310 315 320

Gly Leu Phe Phe Ile Val Arg Phe Leu Glu Ser Asn Trp Phe Val Trp
325 330 335

Val Thr Gln Met Asn His Ile Pro Met His Ile Asp His Asp Arg Asn
340 345 350

Met Asp Trp Val Ser Thr Gln Leu Leu Ala Thr Cys Asn Val His Lys
355 360 365

Ser Ala Phe Asn Asp Trp Phe Ser Gly His Leu Asn Phe Gln Ile Glu
370 375 380

His His Leu Phe Pro Thr Met Pro Arg His Asn Tyr His Lys Val Ala
385 390 395 400

Pro Leu Val Gln Ser Leu Cys Ala Lys Arg Gly Ile Glu Tyr Gln Ser
405 410 415

Lys Pro Leu Leu Ser Ala Phe Ala Asp Ile Ile His Ser Leu Lys Glu
420 425 430

Ser Gly Gln Leu Trp Leu Asp Ala Tyr Leu His Gln Xaa
435 440 445

<210> SEQ ID NO 46
<211> LENGTH: 447
<212> TYPE: PRT
<213> ORGANISM: Homo sapiens
<220> FEATURE:
<221> NAME/KEY: VARIANT
<222> LOCATION: (447)...(447)
<223> OTHER INFORMATION: Xaa = Unknown or other at position 447

<400> SEQUENCE: 46

Met Gly Thr Asp Gln Gly Lys Thr Phe Thr Trp Glu Glu Leu Ala Ala
1 5 10 15

-continued

```
His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu Xaa
```

-continued 435 440 445

<210> SEQ ID NO 47
<211> LENGTH: 39
<212> TYPE: DNA
<213> ORGANISM: Artificial Sequence
<220> FEATURE:
<223> OTHER INFORMATION: Upstream Primer RO676

<400> SEQUENCE: 47
atacgtgaat tcgccgccac catggccccc gacccggtg 39

<210> SEQ ID NO 48
<211> LENGTH: 36
<212> TYPE: DNA
<213> ORGANISM: Artificial Sequence
<220> FEATURE:
<223> OTHER INFORMATION: Downstream Primer RO677

<400> SEQUENCE: 48
tatccgctcg agttattggt gaagataggc atctag 36

<210> SEQ ID NO 49
<211> LENGTH: 21
<212> TYPE: DNA
<213> ORGANISM: Artificial Sequence
<220> FEATURE:
<223> OTHER INFORMATION: Vector Primer RO329

<400> SEQUENCE: 49
cagaccaact ggtaatggta g 21

<210> SEQ ID NO 50
<211> LENGTH: 29
<212> TYPE: DNA
<213> ORGANISM: Artificial Sequence
<220> FEATURE:
<223> OTHER INFORMATION: Vector Primer RO384

<400> SEQUENCE: 50
tcaggcccaa gctggatggc tgcaacatg 29

<210> SEQ ID NO 51
<211> LENGTH: 21
<212> TYPE: DNA
<213> ORGANISM: Artificial Sequence
<220> FEATURE:
<223> OTHER INFORMATION: Vector Primer RO328

<400> SEQUENCE: 51
ctcctggagc ccgtcagtat c 21

<210> SEQ ID NO 52
<211> LENGTH: 29
<212> TYPE: DNA
<213> ORGANISM: Artificial Sequence
<220> FEATURE:
<223> OTHER INFORMATION: Vector Primer RO388

<400> SEQUENCE: 52
atggtgggga agaggtggtg ctcaatctg 29

<210> SEQ ID NO 53
<211> LENGTH: 31
<212> TYPE: DNA
<213> ORGANISM: Artificial Sequence -continued
<220> FEATURE:
<223> OTHER INFORMATION: Primer RO430

<400> SEQUENCE: 53
gtggctgttg ttattggtga agataggcat c 31

<210> SEQ ID NO 54
<211> LENGTH: 20
<212> TYPE: DNA
<213> ORGANISM: Artificial Sequence
<220> FEATURE:
<223> OTHER INFORMATION: Primer RO526

<400> SEQUENCE: 54
catggccccc gacccggtgg 20

<210> SEQ ID NO 55
<211> LENGTH: 20
<212> TYPE: DNA
<213> ORGANISM: Artificial Sequence
<220> FEATURE:
<223> OTHER INFORMATION: Primer RO527

<400> SEQUENCE: 55
gcggccaccg ggtcgggggc 20

<210> SEQ ID NO 56
<211> LENGTH: 34
<212> TYPE: DNA
<213> ORGANISM: Artificial Sequence
<220> FEATURE:
<223> OTHER INFORMATION: Primer RO512

<400> SEQUENCE: 56
gattgggtgc catggggatg cgggatgaaa aggc 34

<210> SEQ ID NO 57
<211> LENGTH: 18
<212> TYPE: DNA
<213> ORGANISM: Artificial Sequence
<220> FEATURE:
<223> OTHER INFORMATION: Primer RO5

<400> SEQUENCE: 57
gaaacagcta tgaccatg 18

<210> SEQ ID NO 58
<211> LENGTH: 34
<212> TYPE: DNA
<213> ORGANISM: Artificial Sequence
<220> FEATURE:
<223> OTHER INFORMATION: Primer RO580

<400> SEQUENCE: 58
tcctgcgaat tcaccatgaa aaggcgggag agag 34

<210> SEQ ID NO 59
<211> LENGTH: 35
<212> TYPE: DNA
<213> ORGANISM: Artificial Sequence
<220> FEATURE:
<223> OTHER INFORMATION: Primer RO578

<400> SEQUENCE: 59
catggctagg agaggcagcg cagccgcgtc tggac 35

-continued

```
<210> SEQ ID NO 60
<211> LENGTH: 35
<212> TYPE: DNA
<213> ORGANISM: Artificial Sequence
<220> FEATURE:
<223> OTHER INFORMATION: Primer RO579

<400> SEQUENCE: 60

ctaggtccag acgcggctgc gctgcctctc ctagc                             35
```